US007560588B2

(12) United States Patent
Breitenkamp et al.

(10) Patent No.: US 7,560,588 B2
(45) Date of Patent: Jul. 14, 2009

(54) POLY(ETHYLENE GLYCOL) CONTAINING CHEMICALLY DISPARATE ENDGROUPS

(75) Inventors: Kurt Breitenkamp, Tampa, FL (US); Kevin N. Sill, Tampa, FL (US); Habib Skaff, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 187 days.

(21) Appl. No.: 11/796,385

(22) Filed: Apr. 27, 2007

(65) Prior Publication Data
US 2008/0207913 A1 Aug. 28, 2008

Related U.S. Application Data

(60) Provisional application No. 60/795,412, filed on Apr. 27, 2006.

(51) Int. Cl.
C07C 261/00 (2006.01)
(52) U.S. Cl. .................................................... 560/160
(58) Field of Classification Search ................ 560/160
See application file for complete search history.

(56) References Cited

U.S. PATENT DOCUMENTS

| | | | |
|---|---|---|---|
| 2,832,795 A | 4/1958 | Hempel et al. | |
| 3,352,838 A | 11/1967 | Toepfl et al. | |
| 4,847,325 A | 7/1989 | Shadle et al. | |
| 5,455,027 A | 10/1995 | Zalipsky et al. | |
| 5,686,110 A | 11/1997 | Greenwald et al. | |
| 5,756,593 A | 5/1998 | Martinez et al. | |
| 5,808,096 A | 9/1998 | Zalipsky | |
| 5,824,701 A | 10/1998 | Greenwald et al. | |
| 6,127,355 A | 10/2000 | Greenwald et al. | |
| 6,180,095 B1 | 1/2001 | Greenwald et al. | |
| 6,251,382 B1 | 6/2001 | Greenwald et al. | |
| 6,448,369 B1 | 9/2002 | Bentley et al. | |
| 6,608,076 B1 | 8/2003 | Greenwald et al. | |
| 6,649,778 B1 | 11/2003 | Zhao et al. | |
| 6,703,446 B2 | 3/2004 | Schwindeman et al. | |
| 6,720,391 B2 | 4/2004 | Schwindeman et al. | |
| 6,737,505 B2 | 5/2004 | Bentley et al. | |
| 6,777,387 B2 | 8/2004 | Greenwald et al. | |
| 6,894,025 B2 | 5/2005 | Harris | |
| 6,899,867 B2 | 5/2005 | Bentley et al. | |
| 7,026,440 B2 | 4/2006 | Bentley et al. | |
| 7,033,583 B2 | 4/2006 | Choe et al. | |
| 2004/0116649 A1 | 6/2004 | Kozlowski | |
| 2005/0031576 A1 | 2/2005 | McManus et al. | |
| 2005/0036978 A1 | 2/2005 | Kozlowski | |
| 2005/0054816 A1 | 3/2005 | McManus et al. | |
| 2005/0119193 A1 | 6/2005 | Motoyama | |
| 2005/0214250 A1 | 9/2005 | Harris et al. | |
| 2006/0142506 A1 | 6/2006 | Breitenkamp et al. | |
| 2006/0172914 A1 | 8/2006 | Breitenkamp et al. | |
| 2006/0240092 A1 | 10/2006 | Breitenkamp et al. | |
| 2008/0035243 A1 | 2/2008 | Breitenkamp et al. | |
| 2008/0188638 A1 | 8/2008 | Breitenkamp et al. | |
| 2008/0207913 A1 | 8/2008 | Breitenkamp et al. | |
| 2008/0274173 A1 | 11/2008 | Sill et al. | |
| 2008/0274965 A1 | 11/2008 | Skaff et al. | |
| 2008/0280998 A1 | 11/2008 | Bonora et al. | |

FOREIGN PATENT DOCUMENTS

| | | |
|---|---|---|
| WO | WO 2005/033181 | 4/2005 |
| WO | WO 2006/086325 | 8/2006 |
| WO | WO 2008134734 | 11/2008 |
| WO | WO 2008134761 | 11/2008 |

OTHER PUBLICATIONS

Akiyama, et al., "Selective Synthesis Of Heterobifunctional Poly(ethylene glycol) Derivatives Containing Both Mercapto And Acetal Terminals.", *Bioconjugate Chem.* 11: 947-950, 2000.

Akiyama, et al., "Synthesis Of Heterotelechelic Poly(ethylene glycol) Derivatives Having α-Benzaldehyde And ω-Pyridyl Disulfide Groups By Ring Opening Polymerization Of Ethylene Oxide Using 4-(Diethoxymethyl)benzyl Alkoxide As A Novel Initiator.", *Bioconjugate Chem.* 15: 424-427, 2004.

Akiyama, et al., "Synthesis Of Poly(ethylene glycol)- Block-Poly(ethylenimine) Possessing An Acetal Group At The PEG End.", *Macromolecules* 33: 5841-5845, 2000.

Bettinger, et al., "Convenient Polymer-Supported Synthetic Route To Heterobifunctional Polyethylene Glycols.", *Bioconjugate Chem.* 9: 842-846, 1998.

Cammas, et al., "Heterobifunctional Poly(ethylene Oxide): Synthesis Of α-Hydroxy- ω- Amino PEOs With The Same Molecular Weights.", *Bioconjugate Chem.* 6: 226-230, 1995.

Dombi, et al., "Oligonucleotide Arrays From Aldehyde-Bearing Glass With Coated Background.", *Synthesis* 6: 816-824, 2002.

Glaied, et al., "Oxazoline-Terminated Macromonomers By The Alkylation Of 2-Methyl-2-Oxazoline.", *Journal of Polymer Science: Part A: Polymer Chem.* 43: 2440-2447, 2005.

Heroguez, et al., "Synthesis Of α-Norbornenylpoly(ethylene oxide) Macromonomers And Their Ring-Opening Metathesis Polymerization.", *Macromeolecules* 29(13): 4459-4464, 1996.

Huang, et al., "The Kinetics Of The Attachment Of Polymer Chains To Reactive Latex Particles And The Resulting Latex Stabilization," *J. of Polymer Sci.*, 23: 795-799, 1985.

Kazanskii, et al., "Strictly Monofunctional Methyl Ethers Of Poly(ethylene glycol) And The Related Methacrylate Macromonomers.", *Polymer Science Ser. A.* 42(6): 585-595, 2000.

Kim, et al., "Heterobifunctional Poly(ethylene oxide)," *Polymer Bulletin*, 33: 1-6, 1994.

Li and Kao, "Synthesis Of Polyethylene Glycol (PEG) Derivatives And PEGylated- Peptide Biopolymer Conjugates.", *Biomacromolecules* 4: 1055-1067, 2003.

Mongondry, et al., "Mild Synthesis Of Amino-Poly(ethylene glycol)s. Application To Steric Stabilization Of Clays.", *Macromol. Rapid Commun.* 24: 681-685, 2003.

(Continued)

Primary Examiner—Rei-tsang Shiao
(74) Attorney, Agent, or Firm—Andrea L. C. Robidoux, Esq.; Choate, Hall & Stewart, LLC

(57) ABSTRACT

The present invention provides bifunctional polymers, methods of preparing the same, and intermediates thereto. These compounds are useful in a variety of applications including the PEGylation of biologically active molecules. The invention also provides methods of using said compounds and compositions thereof.

22 Claims, No Drawings

OTHER PUBLICATIONS

Nagasaki, et al., "Primary Amino-Terminal Heterobifunctional Poly(ethylene Oxide). Facile Synthesis of Poly(ethylene Oxide) With A Primary Amino Group At One End And A Hydroxyl Group At The Other End.", *Bioconjugate Chem.* 6: 702-704, 1995.

Nagasaki, et al., "Synthesis Of Heterotelechelic Poly(ethylene glycol) Macromonomers. Preparation Of Poly(ethylene glycol) Possessing A Methacryloyl Group At One End And A Formyl Group At The Other End.", *Macromolecules* 30: 6489-6493, 1997.

Nakamura, et al., "Synthesis of Heterobifunctional Poly(ethylene glycol) With A Reducing Monosaccharide Residue At One End.", *Bioconjugate Chem.* 9: 300-303, 1998.

Parrish, et al., "Bio-Tailored Amphiphilic Graft Copolymers.", *Polymer Preprints* 46(1): 126, 2005.

Parrish, et al., "PEG- And Peptide-Grafted Aliphatic Polyesters By Click Chemistry.", *J. Am. Chem. Soc.* 127(20): 7404-7410, 2005.

Parrish, et al., "PEG- And Peptide-Tailored Aliphatic Polyesters Synthesized By 'Click' Cycloaddition Chemistry.", *Polymer Preprints* 46(1): 292-293, 2005.

Reed and Janda, "A One-Step Synthesis Of Monoprotected Polyethylene Glycol Ethers," *J. Org. Chem.*, 65: 5843-5845, 2000.

Ryoo, et al., "Efficient Methods Of Converting Hydroxyl Groups Into Amino Groups In Poly(ethylene glycol)-Grafted Polystyrene Resin.", *Journal of Combinatorial Chem.* 4(3): 187-190, 2002.

Senyo, et al., "Syntheses of Poly(ethylene oxide) Macromonomers Carrying Tertiary Amine And Quaternary Ammonium End Groups.", *Polymer Journal* 35(6): 513-518, 2003.

Shen, et al., "One-Step Synthesis of $\alpha$- $\rho$- Vinylphenylalkyl- $\omega$- Hydroxy Poly(ethylene Oxide) Macromonomers By Anionic Polymerization Initiated From $\rho$- Vinylphenylalkanols.", *Polymer* 44: 3221-3228, 2003.

Zhang, et al., "Synthesis Of Heterobifunctional Poly(ethylene glycol) With A Primary Amino Group At One End And A Carboxylate Group At The Other End.", *Reactive & Functional Polymers* 56: 17-25, 2003.

Iliki, et al., "A Facile Synthesis of Azido-Terminated Heterobifunctional Poly(ethyleneglycol)s for "Click" Conjugation.", *Bioconjugate Chem.* 18: 2191-2196, 2007.

POLY(ETHYLENE GLYCOL) CONTAINING CHEMICALLY DISPARATE ENDGROUPS

CROSS-REFERENCE TO RELATED APPLICATIONS

This application claims priority to U.S. provisional patent application Ser. No. 60/795,412, filed Apr. 27, 2006, the entirety of which is hereby incorporated herein by reference.

FIELD OF THE INVENTION

The present invention relates to the field of polymer chemistry and more particularly to functionalized polymers, uses thereof, and intermediates thereto.

BACKGROUND OF THE INVENTION

Poly(ethylene glycol), also known as PEG, is useful in a variety of technological areas and is generally known by the formula HO—$CH_2CH_2$O—($CH_2CH_2$O)$_n$—$CH_2CH_2$—OH, wherein n typically ranges from about 3 to about 4000. In particular, there is great interest in utilizing PEG, and derivatives thereof, in the pharmaceutical and biomedical fields. This interest stems from the fact that PEG is nontoxic, biocompatible, non-immunogenic, soluble in water and other solvents, and is amenable to a variety of therapeutic applications including pharmaceutical formulations and drug delivery systems, among others.

One such area of interest relates to "PEGylation" or "conjugation" which refers to the modification of other molecules, especially biomolecules, using PEG and derivatives thereof. PEGylation is often utilized in order to impart the desirable characteristics of PEG to a particular molecule or biological scaffold. Such molecules or scaffolds targeted for PEGylation include proteins, dyes, peptides, hydrogels, cells, viruses, and drugs, to name but a few. In the case of drugs, the formation of PEG-drug conjugates is also of interest to improve aqueous solubility of hydrophobic drugs and improve biodistribution profiles. In addition, PEG has been utilized with a variety of natural and synthetic substrates including biological implants, medical devices, and the like. Accordingly, it would be advantageous to provide heterobifunctionalized PEG's having a variety of terminal functional groups.

DETAILED DESCRIPTION OF CERTAIN EMBODIMENTS OF THE INVENTION

1. General Description of the Invention

In certain embodiments, the present invention provides a compound of formula I:

I or a salt thereof, wherein:

n is 10-2500;

$R^1$ and $R^2$ are each independently hydrogen, halogen, $NO_2$, CN, $N_3$, —N=C=O, —C(R)=NN(R)$_2$, —P(O)(OR)$_2$, —P(O)(X)$_2$, a 9-30 membered crown ether, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each X is independently halogen;

each R is independently hydrogen or an optionally substituted selected from aliphatic or a 3-8 membered, saturated, partially unsaturated, or aryl ring having 0-4 heteroatoms independently selected from nitrogen, oxygen, or sulfur; and $L^1$ and $L^2$ are each independently a valence bond or a bivalent, saturated or unsaturated, straight or branched $C_{1-12}$ hydrocarbon chain, wherein 0-6 methylene units of $L^1$ and $L^2$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a living polymer chain-end by reacting the living polymer chain-end with a polymerization terminator. Alternatively, the term "termination" may refer to the attachment of a terminal group to a hydroxyl end, or derivative thereof, of the polymer chain.

As used herein, the term "polymerization terminator" is used interchangeably with the term "polymerization terminating agent" and refers to compounds that react with a living polymer chain-end to afford a polymer with a terminal group. Alternatively, the term "polymerization terminator" may refer to a compound that may react with a hydroxyl end, or derivative thereof, of the polymer chain to afford a polymer with a terminal group.

As used herein, the term "polymerization initiator" refers to a compound, or anion thereof, which reacts with ethylene oxide in a manner which results in polymerization thereof. In certain embodiments, the polymerization initiator is the anion of a functional group which initiates the polymerization of ethylene oxide.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^\dagger$)— as in N-substituted pyrrolidinyl.

The term "unsaturated", as used herein, means that a moiety has one or more units of unsaturation.

As used herein, the term "bivalent, saturated or unsaturated, straight or branched $C_{1-12}$ hydrocarbon chain", refers to bivalent alkylene, alkenylene, and alkynylene chains that are straight or branched as defined herein.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}$C(O)OR$^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —C(S)$R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}C(O)R^\circ$; —OC(O)$(CH_2)_{0-4}SR$—, SC(S)S$R^\circ$; —$(CH_2)_{0-4}SC(O)R^\circ$; —$(CH_2)_{0-4}C(O)NR^\circ_2$; —C(S)N$R^\circ_2$; —C(S)S$R^\circ$; —SC(S)S$R^\circ$, —$(CH_2)_{0-4}OC(O)NR^\circ_2$; —C(O)N(OR$^\circ)R^\circ$; —C(O)C(O)$R^\circ$; —C(O)$CH_2$C(O)$R^\circ$; —C(NOR$^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}S(O)_2R^\circ$; —S(O)$_2NR^\circ_2$; —$(CH_2)_{0-4}S(O)R^\circ$; —N($R^\circ$)S(O)$_2NR^\circ_2$; —N($R^\circ$)S(O)$_2R^\circ$; —N(OR$^\circ)R^\circ$; —C(NH)N$R^\circ_2$; —P(O)$_2R^\circ$; —P(O)$R^\circ_2$; —OP(O)$R^\circ_2$; —OP(O)(OR$^\circ)_2$; SiR$^\circ_3$; —($C_{1-4}$ straight or branched alkylene)O—N($R^\circ)_2$; or —($C_{1-4}$ straight or branched alkylene)C(O)O—N($R^\circ)_2$, wherein each $R^\circ$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, —(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —SiR$^\bullet_3$, —OSiR$^\bullet_3$, —C(O)S$R^\bullet$, —($C_{1-4}$ straight or branched alkylene)C(O)OR$^\bullet$, or —SSR$^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2R^*$, =NR*, =NOR*, —O(C($R^*_2$))$_{2-3}$O—, or —S(C($R^*_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

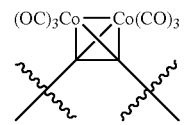

when depicted with the methylenes which bear it.

Suitable substituents on the aliphatic group of R* include halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently $C_{1-4}$ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently $C_{1-4}$ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxycarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

A "crown ether moiety" is the radical of a crown ether. A crown ether is a monocyclic polyether comprised of repeating units of —CH₂CH₂O—. Examples of crown ethers include 12-crown-4, 15-crown-5, and 18-crown-6.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. Such compounds are useful, for example, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}P$, $^{33}P$, $^{35}S$, or $^{14}C$), mass-tags, and fluorescent labels, and are signal-generating reporter groups which can be detected without further modifications.

Other primary labels include those useful for positron emission tomography including molecules containing radioisotopes (e.g. $^{18}F$) or ligands with bound radioactive metals (e.g. $^{62}Cu$). In other embodiments, primary labels are contrast agents for magnetic resonance imaging such as gadolinium, gadolinium chelates, or iron oxide (e.g $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The term "mass-tag" as used herein refers to any compound that is capable of being uniquely detected by virtue of its mass using mass spectrometry (MS) detection techniques. Examples of mass-tags include electrophore release tags such as N-[3-[4'-[(p-methoxytetrafluorobenzyl)oxy]phenyl]-3-methylglyceronyl]-isonipecotic acid, 4'-[2,3,5,6-tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, anthracene, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), carbazole, Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, and Texas Red-X.

The term "substrate", as used herein refers to any material or macromolecular complex to which a functionalized end-group of a PEG can be attached. Examples of commonly used substrates include, but are not limited to, glass surfaces, silica surfaces, plastic surfaces, metal surfaces, surfaces containing a metallic or chemical coating, membranes (e.g., nylon, polysulfone, silica), micro-beads (e.g., latex, polystyrene, or other polymer), porous polymer matrices (e.g., polyacrylamide gel, polysaccharide, polymethacrylate), and macromolecular complexes (e.g., protein, polysaccharide).

The term "targeting group", as used herein refers to any molecule, macromolecule, or biomacromolecule which selectively binds to receptors that are over-expressed on specific cell types. Such molecules can be attached to the functionalized end-group of a PEG for cell specific delivery of proteins, viruses, DNA plasmids, oligonucleotides (e.g. siRNA, miRNA, antisense therapeutics, aptamers, etc.), drugs, dyes, and primary or secondary labels which are bound to the opposite PEG end-group. Such targeting groups include, but or not limited to monoclonal and polyclonal antibodies (e.g. IgG, IgA, IgM, IgD, IgE antibodies), sugars (e.g. mannose, mannose-6-phosphate, galactose), proteins (e.g. transferrin), oligopeptides (e.g. cyclic and acylic RGD-containing oligopeptides), oligonucleotides (e.g. aptamers), and vitamins (e.g. folate).

The term "permeation enhancer", as used herein, refers to any molecule, macromolecule, or biomacromolecule which aids in or promotes the permeation of cellular membranes and/or the membranes of intracellular compartments (e.g. endosome, lysosome, etc.) Such molecules can be attached to the functionalized end-group of a PEG to aid in the intracellular and/or cytoplasmic delivery of proteins, viruses, DNA plasmids, oligonucleotides (e.g. siRNA, miRNA, antisense therapeutics, aptamers, etc.), drugs, dyes, and primary or secondary labels which are bound to the opposite PEG end-group. Such permeation enhancers include, but are not limited to, oligopeptides containing protein transduction domains such as the HIV-1Tat peptide sequence (GRKKRRQRRR), oligoarginine (RRRRRRRRR), or penetratin (RQIKIWFQNRRMKWKK). Oligopeptides which undergo conformational changes in varying pH environments such oligohistidine (HHHHH) also promote cell entry and endosomal escape.

3. Description of Exemplary Embodiments

As defined generally above, the n group of formula I is 10-2500. In certain embodiments, the present invention provides compounds of formula I, as described above, wherein n is about 225. In other embodiments, n is about 10 to about 40. In other embodiments, n is about 40 to about 60. In other embodiments, n is about 60 to about 90. In still other embodiments, n is about 90 to about 150. In other embodiments, n is about 150 to about 200. In still other embodiments, n is about 200 to about 250. In other embodiments, n is about 300 to about 375. In other embodiments, n is about 400 to about 500. In still other embodiments, n is about 650 to about 750. In certain embodiments, n is selected from 50±10. In other embodiments, n is selected from 80±10, 115±10, 180±10, or 225±10.

According to another embodiment, the present invention provides a compound of formula I, as described above, wherein said compound has a polydispersity index ("PDI") of about 1.0 to about 1.2. According to another embodiment, the present invention provides a compound of formula I, as described above, wherein said compound has a polydispersity index ("PDI") of about 1.02 to about 1.05. According to yet another embodiment, the present invention provides a compound of formula I, as described above, wherein said compound has a polydispersity index ("PDI") of about 1.05 to about 1.10. In other embodiments, said compound has a PDI of about 1.01 to about 1.03. In other embodiments, said compound has a PDI of about 1.10 to about 1.15. In still other embodiments, said compound has a PDI of about 1.15 to about 1.20.

In certain embodiments, the present invention provides a compound of formula I, as described above, wherein the $R^1$ and $R^2$ groups of formula I are different from each other.

In other embodiments, the present invention provides a compound of formula I, as described above, wherein only one of -$L^1$-$R^1$ and -$L^2$-$R^2$ is a hydroxyl group.

In still other embodiments, the present invention provides a compound of formula I, as described above, wherein neither of -$L^1$-$R^1$ and -$L^2$-$R^2$ is a hydroxyl group.

As defined generally above, $R^1$ is hydrogen, halogen, $NO_2$, CN, $N_3$, —N=C=O, —C(R)=NN(R)$_2$, —P(O)(OR)$_2$, —P(O)(X)$_2$, a 9-30-membered crown ether, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; wherein each R is independently hydrogen or an optionally substituted aliphatic group.

In certain embodiments, $R^1$ is optionally substituted aliphatic. In other embodiments, $R^1$ is an unsubstituted aliphatic. In some embodiments, said $R^1$ moiety is an optionally substituted alkyl group. In other embodiments, said $R^1$ moiety is an optionally substituted alkynyl or alkenyl group. Such groups include t-butyl, 5-norbornene-2-yl, octane-5-yl, —C≡CH, —CH$_2$C≡CH, —CH$_2$CH$_2$C≡CH, and —CH$_2$CH$_2$CH$_2$C≡CH. When said $R^1$ moiety is a substituted aliphatic group, suitable substituents on $R^1$ include any of CN, $N_3$, $NO_2$, —CO$_2$H, —SH, —NH$_2$, —C(O)H, —NHC(O)R°, —NHC(S)R°, —NHC(O)NR°$_2$, —NHC(S)NR°$_2$, —NHC(O)OR°, —NHNHC(O)R°, —NHNHC(O)NR°$_2$, —NHNHC(O)OR°, —C(O)R°, —C(S)R°, —C(O)OR°, —C(O)SR°, —C(O)OSiR°$_3$, —OC(O)R°, SC(S)SR°, —SC(O)R°, —C(O)N(R°)$_2$, —C(S)N(R°)$_2$, —C(S)SR°, —SC(S)SR°, —OC(O)N(R°)$_2$, —C(O)NHN(R°)$_2$, —C(O)N(OR°)R°, —C(O)C(O)R°, —C(O)CH$_2$C(O)R°, —C(NOR°)R°, —SSR°, —S(O)$_2$R°, —S(O)$_2$OR°, —OS(O)$_2$R°, —S(O)$_2$N(R°)$_2$, —S(O)R°, —N(R°)S(O)$_2$N(R°)$_2$, —N(R°)S(O)$_2$R°, —N(OR°)R°, —C(NH)N(R°)$_2$, —P(O)$_2$R°, —P(O)(R°)$_2$, —OP(O)(R°)$_2$, or —OP(O)(OR°)$_2$, wherein each R° is as defined herein.

In other embodiments, $R^1$ is an aliphatic group optionally substituted with any of Cl, Br, I, F, —NH2, —OH, —SH, —CO$_2$H, —C(O)H, —C(O)(C$_{1-6}$ aliphatic), —NHC(O)(C$_{1-6}$ aliphatic), —NHC(O)NH$_2$, —NHC(O)NH(C$_{1-6}$ aliphatic), —NHC(S)NH—, —NHC(S)N(C$_{1-6}$ aliphatic)$_2$, —NHC(O)O(C$_{1-6}$ aliphatic), —NHNH$_2$, —NHNHC(O)(C$_{1-6}$ aliphatic), —NHNHC(O)NH$_2$, —NHNHC(O)NH(C$_{1-6}$ aliphatic), —NHNHC(O)O(C$_{1-6}$ aliphatic), —C(O)NH$_2$, —C(O)NH(C$_{1-6}$ aliphatic)$_2$, —C(O)NHNH$_2$, —C(S)N(C$_{1-6}$ aliphatic)$_2$, —OC(O)NH(C$_{1-6}$ aliphatic), —C(O)C(O)(C$_{1-6}$ aliphatic), —C(O)CH$_2$C(O)(C$_{1-6}$ aliphatic), —S(O)$_2$(C$_{1-6}$ aliphatic), —S(O)$_2$O(C$_{1-6}$ aliphatic), —OS(O)$_2$(C$_{1-6}$ aliphatic), —S(O)$_2$NH(C$_{1-6}$ aliphatic), —S(O)(C$_{1-6}$ aliphatic), —NHS(O)$_2$NH(C$_{1-6}$ aliphatic), —NHS(O)$_2$(C$_{1-6}$ aliphatic), —P(O)$_2$(C$_{1-6}$ aliphatic), —P(O)(C$_{1-6}$ aliphatic)$_2$, —OP(O)(C$_{1-6}$ aliphatic)$_2$, or —OP(O)(OC$_{1-6}$ aliphatic)$_2$. In other embodiments, the $R^1$ group of formula I is an optionally substituted aliphatic group having substituents as depicted in the Appendix.

In certain embodiments, the $R^1$ group of formula I is a group suitable for Click chemistry. Click reactions tend to involve high-energy ("spring-loaded") reagents with well-defined reaction coordinates, that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition is one such reaction. Click chemistry is known in the art and one of ordinary skill in the art would recognize that certain $R^1$ moieties of the present invention are suitable for Click chemistry.

According to one embodiment, the $R^1$ group of formula I is an azide-containing group. According to another embodiment, the $R^1$ group of formula I is an alkyne-containing group. In certain embodiments, the $R^1$ group of formula I has a terminal alkyne moiety. According to another embodiment, the $R^1$ group of formula I is an aldehyde-containing group. In certain embodiments, the $R^1$ group of formula I has a terminal hydrazine moiety. In other embodiments, the $R^1$ group of formula I has a terminal oxyamine moiety. In still other embodiments, the $R^1$ group of formula I is a epoxide-containing group. In certain other embodiments, the $R^1$ group of formula I has a terminal maleimide moiety.

In other embodiments, $R^1$ is an optionally substituted 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur. In certain embodiments, $R^1$ is an optionally substituted 5-7 membered saturated or partially unsaturated ring having 0-4 heteroatoms independently selected from nitrogen, oxygen, or sulfur. In other embodiments, $R^1$ is an optionally substituted phenyl ring or a 5-6 membered heteroaryl ring having 1-4 heteroatoms independently selected from nitrogen, oxygen, or sulfur.

In certain embodiments, the $R^1$ group of formula I is an optionally substituted aryl group. Examples include optionally substituted phenyl, optionally substituted pyridyl, optionally substituted naphthyl, optionally substituted pyrenyl, optionally substituted triazole, optionally substituted imidazole, optionally substituted phthalimide, optionally substituted tetrazole, optionally substituted furan, and optionally substituted pyran. When said $R^1$ moiety is a substituted aryl group, suitable substituents on $R^1$ include any of R°, CN, $N_3$, $NO_2$, —CH$_3$, —CH$_2$N$_3$, t-butyl, 5-norbornene-2-yl, octane-5-yl, —CH=CH$_2$, —C≡CH, —CH$_2$C≡CH, —CH$_2$CH$_2$C≡CH, —CH$_2$CH$_2$CH$_2$C≡CH, Cl, Br, I, F, —NH₂, —OH, —SH, —CO₂H, —C(O)H, —CH₂NH₂, —CH₂OH, —CH₂SH, —CH₂CO₂H, —CH₂C(O)H, —C(O)(C₁₋₆ aliphatic), —NHC(O)(C₁₋₆ aliphatic), —NHC(O)NH—, —NHC(O)NH(C₁₋₆ aliphatic), —NHC(S)NH₂, —NHC(S)N(C₁₋₆ aliphatic)₂, —NHC(O)O(C₁₋₆ aliphatic), —NHNH₂, —NHNHC(O)(C₁₋₆ aliphatic), —NHNHC(O)NH₂, —NHNHC(O)NH(C₁₋₆ aliphatic), —NHNHC(O)O(C₁₋₆ aliphatic), —C(O)NH₂, —C(O)NH(C₁₋₆ aliphatic)₂, —C(O)NHNH₂, —C(S)N(C₁₋₆ aliphatic)₂, —OC(O)NH(C₁₋₆ aliphatic), —C(O)C(O)(C₁₋₆ aliphatic), —C(O)CH₂C(O)(C₁₋₆ aliphatic), —S(O)₂(C₁₋₆ aliphatic), —S(O)₂O(C₁₋₆ aliphatic), —OS(O)₂(C₁₋₆ aliphatic), —S(O)₂NH(C₁₋₆ aliphatic), —S(O)(C₁₋₆ aliphatic), —NHS(O)₂NH(C₁₋₆ aliphatic), —NHS(O)₂(C₁₋₆ aliphatic), —P(O)₂(C₁₋₆ aliphatic), —P(O)(C₁₋₆ aliphatic)₂, —OP(O)(C₁₋₆ aliphatic)₂, or —OP(O)(OC₁₋₆ aliphatic)₂.

Suitable substitutents on R¹ further include bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, R¹ is hydrogen.

In certain embodiments, R¹ is N₃.

In other embodiments, R¹ is an epoxide ring.

According to certain embodiments, R¹ is methyl.

According to other embodiments, R¹ is —NH₂.

In certain embodiments, the R¹ group of formula I is a crown ether. Examples of such crown ethers include 12-crown-4, 15-crown-5, and 18-crown-6.

In still other embodiments, R¹ is a detectable moiety. Detectable moieties are known in the art and include those described herein. According to one aspect of the invention, the R¹ group of formula I is a fluorescent moiety. Such fluorescent moieties are well known in the art and include coumarins, quinolones, benzoisoquinolones, hostasol, and Rhodamine dyes, to name but a few. Exemplary fluorescent moieties of R¹ include anthracen-9-yl, pyren-4-yl, 9-H-carbazol-9-yl, the carboxylate of rhodamine B, and the carboxylate of coumarin 343. In certain embodiments, R¹ is a detectable moiety selected from:

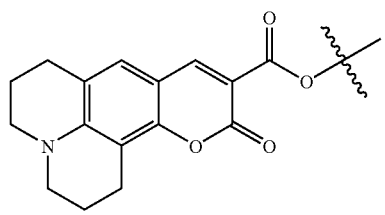

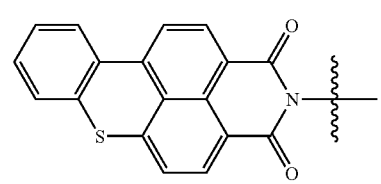

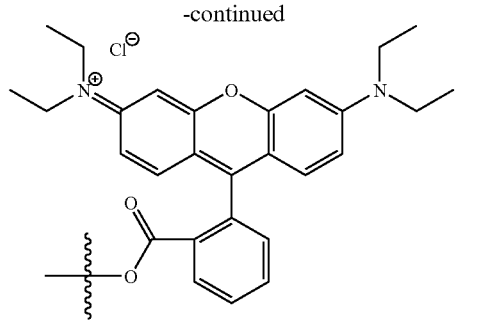

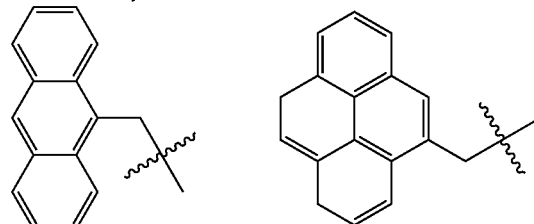

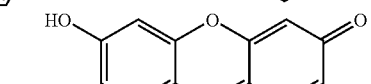

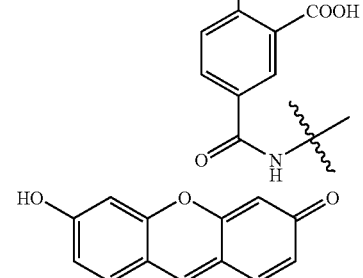

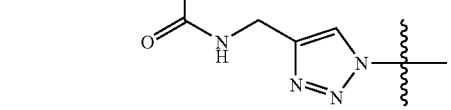

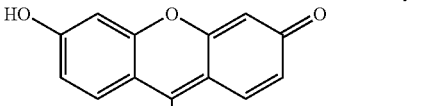

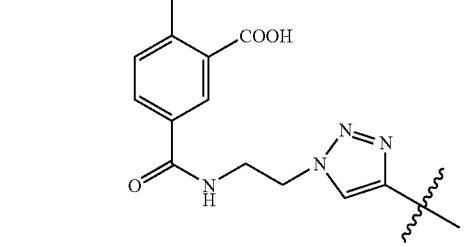

wherein each wavy line indicates the point of attachment to the rest of the molecule.

In certain embodiments, R¹ is —P(O)(OR)₂, or —P(O)(halogen)₂. According to one aspect, the present invention provides a compound of formula I, wherein R¹ is —P(O)

(OH)$_2$. According to another aspect, the present invention provides a compound of formula I, wherein R$^1$ is —P(O)(Cl)$_2$.

According to one embodiment, the R$^1$ group of formula I is selected from any of those depicted in Tables 1 through 25.

As defined generally above, the L$^1$ group of formula I is a valence bond or a bivalent, saturated or unsaturated, straight or branched C$_{1-12}$ hydrocarbon chain, wherein 0-6 methylene units of L$^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, L$^1$ is a valence bond. In other embodiments, L$^1$ is a bivalent, saturated C$_{1-12}$ hydrocarbon chain, wherein 0-6 methylene units of L$^1$ are independently replaced by -Cy-, —O—, —NH—, —S—, —OC(O)—, —C(O)O—, —C(O)—, —C(O)NH—, or —NHC(O)—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In still other embodiments, L$^1$ is a bivalent, saturated C$_{1-6}$ alkylene chain, wherein 0-3 methylene units of L$^1$ are independently replaced by -Cy-, —O—, —NH—, —S—, —OC(O)—, —C(O)O—, —C(O)—, —C(O)NH—, or —NHC(O)—.

In certain embodiments, L$^1$ is a C$_{1-6}$ alkylene chain wherein one methylene unit of L$^1$ is replaced by -Cy-. In other embodiments, L$^1$ is -Cy- (i.e. a C$_1$ alkylene chain wherein the methylene unit is replaced by -Cy-), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the L$^1$ group of formula I is —O—, —S—, —NH—, or —C(O)O—. In other embodiments, the L$^1$ group of formula I is -Cy-, —C(O)—, —C(O)NH—, —NHC(O)—, —NH—O—, or —O-Cy-CH$_2$NH—O—. In still other embodiments, the L$^1$ group of formula I is any of —OCH$_2$—, —OCH$_2$C(O)—, —OCH$_2$CH$_2$C(O)—, —OCH$_2$CH$_2$O—, —OCH$_2$CH$_2$S—, —OCH$_2$CH$_2$C(O)O—, —OCH$_2$CH$_2$NH—, —OCH$_2$CH$_2$NHC(O)—, —OCH$_2$CH$_2$C(O)NH—, and —NHC(O)CH$_2$CH$_2$C(O)O—. According to another aspect, the L$^1$ group of formula I is any of —OCH$_2$CH$_2$NHC(O)CH$_2$CH$_2$C(O)O—, —OCH$_2$CH$_2$NHC(O)CH$_2$OCH$_2$C(O)O—, —OCH$_2$CH$_2$NHC(O)CH$_2$OCH$_2$C(O)NH—, —CH$_2$C(O)NH—, —CH$_2$C(O)NHNH—, or —OCH$_2$CH$_2$NHNH—. In certain embodiments, L$^1$ is a C$_{1-6}$ alkylene chain wherein one methylene unit of L$^1$ is replaced by —O—. In other embodiments, L$^1$ is —O—. Exemplary L$^1$ groups of formula I include any of those depicted in any of Tables 1 through 25.

According to another aspect of the present invention, a functional group formed by the -L$^1$-R$^1$ moiety of formula I is optionally protected. Thus, in certain embodiments, the -L$^1$-R$^1$ moiety of formula I optionally comprises a mono-protected amine, a di-protected amine, a protected aldehyde, a protected hydroxyl, a protected carboxylic acid, or a protected thiol group.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

As defined generally above, the $R^2$ group of formula I is hydrogen, halogen, $NO_2$, CN, $N_3$, —N═C═O, —C(R)═NN(R)$_2$, —P(O)(OR)$_2$, —P(O)(X)$_2$, a 9-30-membered crown ether, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, wherein each R is independently hydrogen or an optionally substituted aliphatic group.

In certain embodiments, $R^2$ is optionally substituted aliphatic. In other embodiments, $R^2$ is an unsubstituted aliphatic. In some embodiments, said $R^2$ moiety is an optionally substituted alkyl group. In other embodiments, said $R^2$ moiety is an optionally substituted alkynyl or alkenyl group. Such groups include t-butyl, 5-norbornene-2-yl, octane-5-yl, —C≡CH, —CH$_2$C≡CH, —CH$_2$CH$_2$C≡CH, and —CH$_2$CH$_2$CH$_2$C≡CH. When said $R^2$ moiety is a substituted aliphatic group, suitable substituents on $R^2$ include any of CN, $N_3$, $NO_2$, —CO$_2$H, —SH, —NH$_2$, —C(O)H, —NHC(O)R°, —NHC(S)R°, —NHC(O)N(R°)$_2$, —NHC(S)N(R°)$_2$, —NHC(O)OR°, —NHNHC(O)R°, —NHNHC(O)N(R°)$_2$, —NHNHC(O)OR°, —C(O)R°, —C(S)R°, —C(O)OR°, —C(O)SR°, —C(O)OSi(R°)$_3$, —OC(O)R°, SC(S)SR°, —SC(O)R°, —C(O)NR°$_2$, —C(S)NR°$_2$, —C(S)SR°; —SC(S)SR°, —OC(O)N(R°)$_2$; —C(O)NHN(R°)$_2$, —C(O)N(OR°)R°, —C(O)C(O)R°, —C(O)CH$_2$C(O)R°, —C(NOR°)R°, —SSR°, —S(O)$_2$R°, —S(O)$_2$OR°, —OS(O)$_2$R°, —S(O)$_2$N(R°)$_2$, —S(O)R°, —N(R°)S(O)$_2$N(R°)$_2$, —N(R°)S(O)$_2$R°, —N(OR°)R°, —C(NH)N(R°)$_2$, —P(O)$_2$R°, —P(O)(R°)$_2$, —OP(O)(R°)$_2$, or —OP(O)(OR°)$_2$, wherein each R° is as defined herein.

In other embodiments, $R^2$ is an aliphatic group optionally substituted with any of Cl, Br, I, F, —NH$_2$, —OH, —SH, —CO$_2$H, —C(O)H, —C(O)(C$_{1-6}$ aliphatic), —NHC(O)(C$_{1-6}$ aliphatic), —NHC(O)NH—, —NHC(O)NH(C$_{1-6}$ aliphatic), —NHC(S)NH$_2$, —NHC(S)N(C$_{1-6}$ aliphatic)$_2$, —NHC(O)O(C$_{1-6}$ aliphatic), —NHNH$_2$, —NHNHC(O)(C$_{1-6}$ aliphatic), —NHNHC(O)NH$_2$, —NHNHC(O)NH(C$_{1-6}$ aliphatic), —NHNHC(O)O(C$_{1-6}$ aliphatic), —C(O)NH$_2$, —C(O)NH(C$_{1-6}$ aliphatic), —C(O)NHNH$_2$, —C(S)N(C$_{1-6}$ aliphatic)$_2$, —OC(O)NH(C$_{1-6}$ aliphatic), —C(O)C(O)(C$_{1-6}$ aliphatic), —C(O)CH$_2$C(O)(C$_{1-6}$ aliphatic), —S(O)$_2$(C$_{1-6}$ aliphatic), —S(O)$_2$O(C$_{1-6}$ aliphatic), —OS(O)$_2$(C$_{1-6}$ aliphatic), —S(O)$_2$NH(C$_{1-6}$ aliphatic), —S(O)(C$_{1-6}$ aliphatic), —NHS(O)$_2$NH(C$_{1-6}$ aliphatic), —NHS(O)$_2$(C$_{1-6}$ aliphatic), —P(O)$_2$(C$_{1-6}$ aliphatic), —P(O)(C$_{1-6}$ aliphatic)$_2$, —OP(O)(C$_{1-6}$ aliphatic)$_2$, or —OP(O)(OC$_{1-6}$ aliphatic)$_2$. In other embodiments, the $R^2$ group of formula I is an optionally substituted aliphatic group having substituents as depicted in any of Tables 1 through 25.

In certain embodiments, the $R^2$ group of formula I is a group suitable for Click chemistry. Click reactions tend to involve high-energy ("spring-loaded") reagents with well-defined reaction coordinates, that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition is one such reaction. Click chemistry is known in the art and one of ordinary skill in the art would recognize that certain $R^2$ moieties of the present invention are suitable for Click chemistry.

According to one embodiment, the $R^2$ group of formula I is an azide-containing group. According to another embodiment, the $R^2$ group of formula I is an alkyne-containing group. In certain embodiments, the $R^2$ group of formula I has a terminal alkyne moiety. According to another embodiment, the $R^2$ group of formula I is an aldehyde-containing group. In certain embodiments, the $R^2$ group of formula I has a terminal hydrazine moiety. In other embodiments, the $R^2$ group of formula I has a terminal oxyamine moiety. In still other embodiments, the $R^2$ group of formula I is a epoxide-containing group. In certain other embodiments, the $R^2$ group of formula I has a terminal maleimide moiety.

In other embodiments, $R^2$ is an optionally substituted 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur. In certain embodiments, $R^2$ is an optionally substituted 3-7 membered saturated or partially unsaturated ring having 0-4 heteroatoms independently selected from nitrogen, oxygen, or sulfur. In other embodiments, $R^2$ is an optionally substituted phenyl ring or a 5-6 membered heteroaryl ring having 1-4 heteroatoms independently selected from nitrogen, oxygen, or sulfur.

In certain embodiments, the $R^2$ group of formula I is an optionally substituted aryl group. Examples include optionally substituted phenyl, optionally substituted pyridyl, optionally substituted naphthyl, optionally substituted pyrenyl, optionally substituted triazole, optionally substituted imidazole, optionally substituted phthalimide, optionally substituted tetrazole, optionally substituted furan, and optionally substituted pyran. When said $R^2$ moiety is a substituted aryl group, suitable substituents on $R^2$ include R°, CN, $N_3$, $NO_2$, —CH$_3$, —CH$_2$N$_3$, t-butyl, 5-norbornene-2-yl, octane-5-yl, —CH═CH$_2$, —C≡CH, —CH$_2$C≡CH, —CH$_2$CH$_2$C≡CH, —CH$_2$CH$_2$CH$_2$C≡CH, Cl, Br, I, F, —NH$_2$, —OH, —SH, —CO$_2$H, —C(O)H, —CH$_2$NH$_2$, —CH$_2$OH, —CH$_2$SH, —CH$_2$CO$_2$H, —CH$_2$C(O)H, —C(O)(C$_{1-6}$ aliphatic), —NHC(O)(C$_{1-6}$ aliphatic), —NHC(O)NH—, —NHC(O)NH(C$_{1-6}$ aliphatic), —NHC(S)NH—, —NHC(S)N(C$_{1-6}$ aliphatic)$_2$, —NHC(O)O(C$_{1-6}$ aliphatic), —NHNH$_2$, —NHNHC(O)(C$_{1-6}$ aliphatic), —NHNHC(O)NH$_2$, —NHNHC(O)NH(C$_{1-6}$ aliphatic), —NHNHC(O)O(C$_{1-6}$ aliphatic), —C(O)NH$_2$, —C(O)NH(C$_{1-6}$ aliphatic)$_2$, —C(O)NHNH$_2$, —C(S)N(C$_{1-6}$ aliphatic)$_2$, —OC(O)NH ($C_{1-6}$ aliphatic), —C(O)C(O)($C_{1-6}$ aliphatic), —C(O)CH$_2$C(O)($C_{1-6}$ aliphatic), —S(O)$_2$($C_{1-6}$ aliphatic), —S(O)$_2$O($C_{1-6}$ aliphatic), —OS(O)$_2$($C_{1-6}$ aliphatic), —S(O)$_2$NH($C_{1-6}$ aliphatic), —S(O)($C_{1-6}$ aliphatic), —NHS(O)$_2$NH($C_{1-6}$ aliphatic), —NHS(O)$_2$($C_{1-6}$ aliphatic), —P(O)$_2$($C_{1-6}$ aliphatic), —P(O)($C_{1-6}$ aliphatic)$_2$, —OP(O)($C_{1-6}$ aliphatic)$_2$, or —OP(O)(O$C_{1-6}$ aliphatic)$_2$.

Suitable substitutents on $R^2$ further include bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, $R^2$ is hydrogen.

In certain embodiments, $R^2$ is $N_3$.

In other embodiments, $R^2$ is an epoxide ring.

In certain embodiments, $R^2$ is Me. In other embodiments, $R^2$ is —NH$_2$.

In certain embodiments, the $R^2$ group of formula I is a crown ether. Examples of such crown ethers include 12-crown-4, 15-crown-5, and 18-crown-6.

In still other embodiments, $R^2$ is a detectable moiety. Detectable moieties are known in the art and include those described herein. According to one aspect of the invention, the $R^2$ group of formula I is a fluorescent moiety. Such fluorescent moieties are well known in the art and include coumarins, quinolones, benzoisoquinolones, hostasol, and Rhodamine dyes, to name but a few. Exemplary fluorescent moieties of $R^2$ include anthracen-9-yl, pyren-4-yl, 9-H-carbazol-9-yl, the carboxylate of rhodamine B, and the carboxylate of coumarin 343. In certain embodiments, $R^2$ is a detectable moiety selected from:

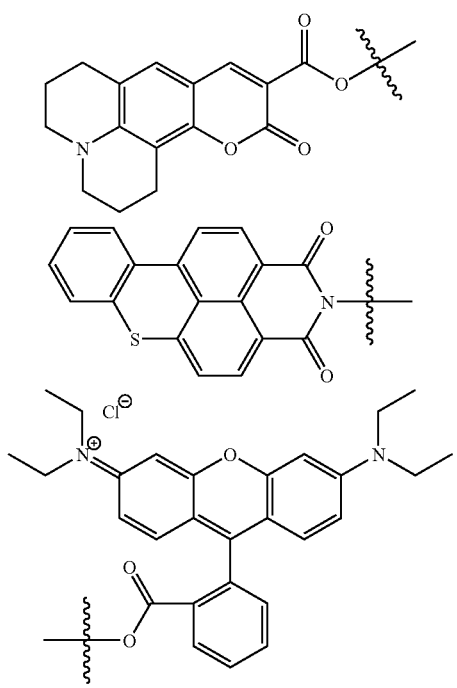

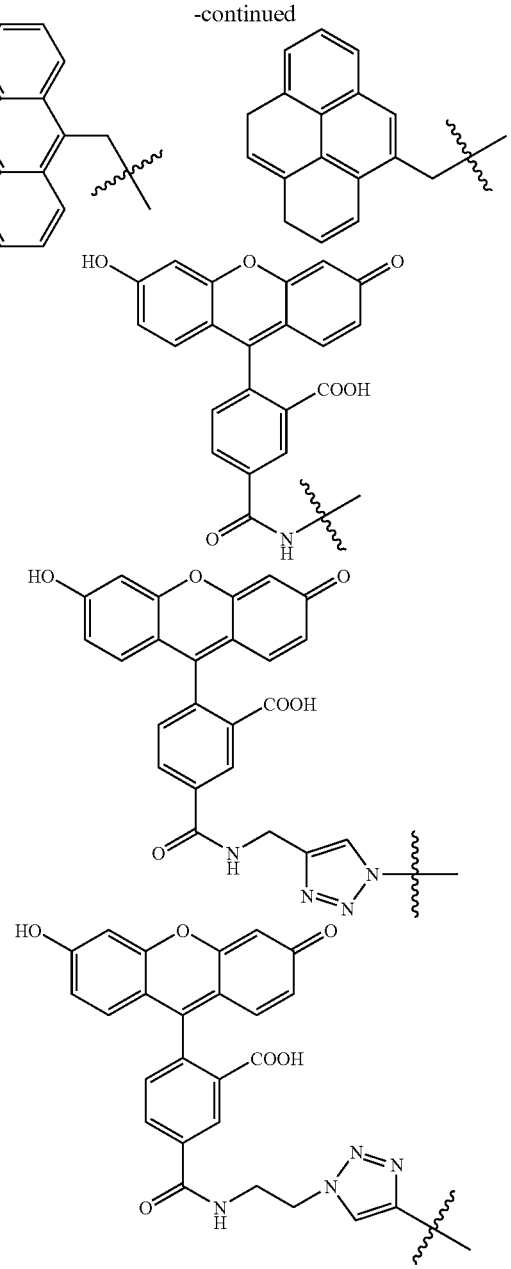

wherein each wavy line indicates the point of attachment to the rest of the molecule.

In certain embodiments, $R^2$ is —P(O)(OR)$_2$, or —P(O)(X)$_2$. According to one aspect, the present invention provides a compound of formula I, wherein $R^2$ is —P(O)(OH)$_2$. According to another aspect, the present invention provides a compound of formula I, wherein $R^2$ is —P(O)(Cl)$_2$.

In certain embodiments, the $R^2$ group of formula I is selected from any of those depicted in any of Tables 1 through 25

As defined generally above, the $L^2$ group of formula I is a valence bond or a bivalent, saturated or unsaturated, straight or branched $C_{1-12}$ hydrocarbon chain, wherein 0-6 methylene units of $L^2$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC (O)—, —C(O)NR—, —OC(O)NR—, —NRC(O)O—, —NH—O—, or —O-Cy-CH₂NH—O—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, $L^2$ is a valence bond. In other embodiments, $L^2$ is a bivalent, saturated $C_{1-12}$ alkylene chain, wherein 0-6 methylene units of $L^2$ are independently replaced by -Cy-, —O—, —NH—, —S—, —OC(O)—, —C(O)O—, —C(O)—, —C(O)NH—, or —NHC(O)—, wherein each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In still other embodiments, $L^2$ is a bivalent, saturated $C_{1-6}$ alkylene chain, wherein 0-3 methylene units of $L^2$ are independently replaced by -Cy-, —O—, —NH—, —S—, —OC(O)—, —C(O)O—, —C(O)—, —C(O)NH—, or —NHC(O)—.

In certain embodiments, $L^2$ is a $C_{1-6}$ alkylene chain wherein one methylene unit of $L^2$ is replaced by -Cy- or —OCy-. In other embodiments, $L^2$ is -Cy- (i.e. a $C_1$ alkylene chain wherein the methylene unit is replaced by -Cy-), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, $L^2$ is —O-Cy- (i.e. a $C_2$ alkylene chain wherein one methylene unit is replaced by -Cy- and the other by —O—), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $L^2$ group of formula I is —O—, —S—, —NH—, or —C(O)O—. In other embodiments, the $L^2$ group of formula I is -Cy-, —C(O)—, —C(O)NH—, —NH—O—, —O-Cy-CH₂NH—O—, or —NHC(O)—. In still other embodiments, the $L^2$ group of formula I is any of —OCH₂—, —OCH₂C(O)—, —OCH₂CH₂C(O)—, —OCH₂CH₂O—, —OCH₂CH₂S—, —OCH₂CH₂C(O)O—, —OCH₂CH₂NH—, —OCH₂CH₂NHC(O)—, —OCH₂CH₂C(O)NH—, and —NHC(O)CH₂CH₂C(O)O—. According to another aspect, the $L^2$ group of formula I is any of —OCH₂CH₂NHC(O)CH₂CH₂C(O)O—, —OCH₂CH₂NHC(O)CH₂OCH₂C(O)O—, —OCH₂CH₂NHC(O)CH₂OCH₂C(O)NH—, —CH₂C(O)NH—, —CH₂C(O)NHNH—, or —OCH₂CH₂NHNH—. In other embodiments, the $L^2$ group of formula I is —OC(O)CH₂CH₂CH₂CH₂—, —OCH₂CH₂—, —NHC(O)CH₂CH₂—, —NHC(O)CH₂CH₂CH₂—, —OC(O)CH₂CH₂CH₂—, —O-Cy-, —O-Cy-CH₂—, —O-Cy-NH—, —O-Cy-S—, —O-Cy-C(O)—, —O-Cy-C(O)O—, —O-Cy-C(O)O-Cy-, —O-Cy-OCH₂CH(CH₃)C(O)O—, —O-Cy-C(O)O—, —O-Cy-OCH(CH₃)CH₂C(O)O—, —OCH₂C(O)O—, —OCH₂C(O)NH—, —OCH₂O—, —OCH₂S—, or —OCH₂NH—. In certain embodiments, $L^2$ is —O—. Exemplary $L^2$ groups of formula I include any of those depicted in any of Tables 1 through 25.

According to another aspect of the present invention, a functional group formed by the -$L^2$-$R^2$ moiety of formula I is optionally protected. Thus, in certain embodiments, the -$L^2$-$R^2$ moiety of formula I optionally comprises a mono-protected amine, a di-protected amine, a protected aldehyde, a protected hydroxyl, a protected carboxylic acid, or a protected thiol group. Such groups include those described above with respect to the -$L^1$-$R^1$ moiety of formula I.

Exemplary compounds of formula I are set forth in the Appendix, wherein each n is as defined herein. In certain embodiments, the present invention provides any compound as depicted in the Appendix.

According to another aspect of the present invention, the $R^2$ group of formula I is —P(O)(OR)₂. Accordingly, the present invention provides a compound of formula IIa:

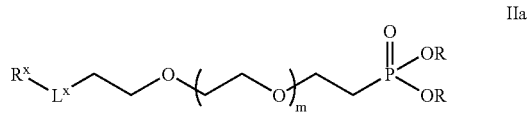

or a salt thereof, wherein:

m is 10-2500;

$R^x$ is hydrogen, halogen, NO₂, CN, N₃, —N=C=O, —C(R)=NN(R)₂, —P(O)(OR)₂, —P(O)(X)₂, a 9-30 membered crown ether, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each X is independently halogen;

each R is independently hydrogen or an optionally substituted group selected from aliphatic or a a 3-8 membered saturated, partially unsaturated, or aryl ring having 0-4 heteroatoms independently selected from nitrogen, oxygen, or sulfur;

$L^x$ is a valence bond or a bivalent, saturated or unsaturated, straight or branched $C_{1-12}$ hydrocarbon chain, wherein 0-6 methylene units of $L^x$ are independently replaced by -Cy-, —O—, —NR—, —S—, —OC(O)—, —C(O)O—, —C(O)—, —SO—, —SO₂—, —NRSO₂—, —SO₂NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

As defined generally above, the m group of formula IIa is 10-2500. In certain embodiments, the present invention provides compounds of formula IIa, as described above, wherein m is about 225. In other embodiments, m is about 10 to about 40. In other embodiments, m is about 40 to about 60. In other embodiments, m is about 60 to about 90. In still other embodiments, m is about 90 to about 150. In other embodiments, m is about 150 to about 200. In still other embodiments, m is about 200 to about 250. In other embodiments, m is about 300 to about 375. In other embodiments, m is about 400 to about 500. In still other embodiments, m is about 650 to about 750.

According to another embodiment, the present invention provides a compound of formula IIa, as described above, wherein said compound has a polydispersity index ("PDI") of about 1.0 to about 1.2. According to another embodiment, the present invention provides a compound of formula IIa, as described above, wherein said compound has a polydispersity index ("PDI") of about 1.02 to about 1.05. According to yet another embodiment, the present invention provides a compound of formula IIa, as described above, wherein said compound has a polydispersity index ("PDI") of about 1.05 to about 1.10. In other embodiments, said compound has a PDI of about 1.01 to about 1.03. In other embodiments, said compound has a PDI of about 1.10 to about 1.15. In still other embodiments, said compound has a PDI of about 1.15 to about 1.20.

In other embodiments, the present invention provides a compound of formula IIa, as described above, wherein -$L^x$-$R^x$ is a hydroxyl group.

As defined generally above, the $R^x$ group of formula IIa is hydrogen, halogen, $NO_2$, CN, $N_3$, —N=C=O, —C(R)=NN(R)$_2$, —P(O)(OR)$_2$, —P(O)(halogen)$_2$, a 9-30-membered crown ether, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; wherein each R is independently hydrogen or an optionally substituted aliphatic group.

In certain embodiments, the $R^x$ group of formula IIa is optionally substituted aliphatic. In other embodiments, $R^x$ is an unsubstituted aliphatic. In some embodiments, said $R^x$ moiety is an optionally substituted alkyl group. In other embodiments, said $R^x$ moiety is an optionally substituted alkynyl or alkenyl group. Such groups include t-butyl, 5-norbornene-2-yl, octane-5-yl, —C≡CH, —$CH_2$C≡CH, —$CH_2CH_2$C≡CH, and —$CH_2CH_2CH_2$C≡CH. When said $R^x$ moiety is a substituted aliphatic group, suitable substituents on $R^x$ include any of CN, $N_3$, $NO_2$, —$CO_2H$, —SH, —$NH_2$, —C(O)H, —NHC(O)$R^o$, —NHC(S)$R^o$, —NHC(O)N$R^o{}_2$, —NHC(S)N$R^o{}_2$, —NHC(O)O$R^o$, —NHNHC(O)$R^o$, —NHNHC(O)N$R^o{}_2$, —NHNHC(O)O$R^o$, —C(O)$R^o$, —C(S)$R^o$, —C(O)O$R^o$, —C(O)S$R^o$, —C(O)OSi$R^o{}_3$, —OC(O)$R^o$, SC(S)S$R^o$, —SC(O)$R^o$, —C(O)N($R^o$)$_2$, —C(S)N($R^o$)$_2$, —C(S)S$R^o$, —SC(S)S$R^o$, —OC(O)N($R^o$)$_2$, —C(O)NHN($R^o$)$_2$, —C(O)N(O$R^o$)$R^o$, —C(O)C(O)$R^o$, —C(O)$CH_2$C(O)$R^o$, —C(NO$R^o$)$R^o$, —SS$R^o$, —S(O)$_2R^o$, —S(O)$_2$O$R^o$, —OS(O)$_2R^o$, —S(O)$_2$N($R^o$)$_2$, —S(O)$R^o$, —N($R^o$)S(O)$_2$N($R^o$)$_2$, —N($R^o$)S(O)$_2R^o$, —N(O$R^o$)$R^o$, —C(NH)N($R^o$)$_2$, —P(O)$_2R^o$, —P(O)($R^o$)$_2$, —OP(O)($R^o$)$_2$, or —OP(O)(O$R^o$)$_2$, wherein each $R^o$ is as defined herein.

In other embodiments, $R^x$ is an aliphatic group optionally substituted with any of Cl, Br, I, F, —$NH_2$, —OH, —SH, —$CO_2H$, —C(O)H, —C(O)($C_{1-6}$ aliphatic), —NHC(O)($C_{1-6}$ aliphatic), —NHC(O)$NH_2$, —NHC(O)NH($C_{1-6}$ aliphatic), —NH C(S)NH—, —NHC(S)N($C_{1-6}$ aliphatic)$_2$, —NHC(O)O($C_{1-6}$ aliphatic), —$NHNH_2$, —NHNHC(O)($C_{1-6}$ aliphatic), —NHNHC(O)$NH_2$, —NHNHC(O)NH($C_{1-6}$ aliphatic), —NHNHC(O)O($C_{1-6}$ aliphatic), —C(O)$NH_2$, —C(O)NH($C_{1-6}$ aliphatic)$_2$, —C(O)NHN$H_2$, —C(S)N($C_{1-6}$ aliphatic)$_2$, —OC(O)NH($C_{1-6}$ aliphatic), —C(O)C(O)($C_{1-6}$ aliphatic), —C(O)$CH_2$C(O)($C_{1-6}$ aliphatic), —S(O)$_2$($C_{1-6}$ aliphatic), —S(O)$_2$O($C_{1-6}$ aliphatic), —OS(O)$_2$($C_{1-6}$ aliphatic), —S(O)$_2$NH($C_{1-6}$ aliphatic), —S(O)($C_{1-6}$ aliphatic), —NHS(O)$_2$NH($C_{1-6}$ aliphatic), —NHS(O)$_2$($C_{1-6}$ aliphatic), —P(O)$_2$($C_{1-6}$ aliphatic), —P(O)($C_{1-6}$ aliphatic)$_2$, —OP(O)($C_{1-6}$ aliphatic)$_2$, or —OP(O)(O$C_{1-6}$ aliphatic)$_2$. In other embodiments, the $R^x$ group of formula IIa is an optionally substituted aliphatic group having substituents as depicted in any of Tables 1 through 25.

In certain embodiments, the $R^x$ group of formula IIa is a group suitable for Click chemistry. Click reactions tend to involve high-energy ("spring-loaded") reagents with well-defined reaction coordinates, that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition is one such reaction. Click chemistry is known in the art and one of ordinary skill in the art would recognize that certain $R^x$ moieties of the present invention are suitable for Click chemistry.

According to one embodiment, the $R^x$ group of formula IIa is an azide-containing group. According to another embodiment, the $R^x$ group of formula IIa is an alkyne-containing group. In certain embodiments, the $R^x$ group of formula IIa has a terminal alkyne moiety. According to another embodiment, the $R^x$ group of formula IIa is an aldehyde-containing group. In certain embodiments, the $R^x$ group of formula I has a terminal hydrazine moiety. In other embodiments, the $R^x$ group of formula IIa has a terminal oxyamine moiety. In still other embodiments, the $R^x$ group of formula IIa is a epoxide-containing group. In certain other embodiments, the $R^x$ group of formula IIa has a terminal maleimide moiety.

In other embodiments, $R^x$ is an optionally substituted 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur. In certain embodiments, $R^x$ is an optionally substituted 5-7 membered saturated or partially unsaturated ring having 0-4 heteroatoms independently selected from nitrogen, oxygen, or sulfur. In other embodiments, $R^x$ is an optionally substituted phenyl ring or a 5-6 membered heteroaryl ring having 1-4 heteroatoms independently selected from nitrogen, oxygen, or sulfur.

In certain embodiments, the $R^x$ group of formula IIa is an optionally substituted aryl group. Examples include optionally substituted phenyl, optionally substituted pyridyl, optionally substituted naphthyl, optionally substituted pyrenyl, optionally substituted triazole, optionally substituted imidazole, optionally substituted phthalimide, optionally substituted tetrazole, optionally substituted furan, and optionally substituted pyran. When said $R^x$ moiety is a substituted aryl group, suitable substituents on $R^1$ include $R^\circ$, CN, $N_3$, $NO_2$, —$CH_3$, —$CH_2N_3$, t-butyl, 5-norbornene-2-yl, octane-5-yl, —CH=$CH_2$, —C≡CH, —$CH_2$C≡CH, —$CH_2CH_2$C≡CH, —$CH_2CH_2CH_2$C≡CH, Cl, Br, I, F, —$NH_2$, —OH, —SH, —$CO_2H$, —C(O)H, —$CH_2NH_2$, —$CH_2OH$, —$CH_2SH$, —$CH_2CO_2H$, —$CH_2C(O)H$, —C(O)($C_{1-6}$ aliphatic), —NHC(O)($C_{1-6}$ aliphatic), —NHC(O)NH—, —NHC(O)NH($C_{1-6}$ aliphatic), —NHC(S)$NH_2$, —NHC(S)N($C_{1-6}$ aliphatic)$_2$, —NHC(O)O($C_{1-6}$ aliphatic), —$NHNH_2$, —NHNHC(O)($C_{1-6}$ aliphatic), —NHNHC(O)$NH_2$, —NHNHC(O)NH($C_{1-6}$ aliphatic), —NHNHC(O)O($C_{1-6}$ aliphatic), —C(O)$NH_2$, —C(O)NH($C_{1-6}$ aliphatic)$_2$, —C(O)$NHNH_2$, —C(S)N($C_{1-6}$ aliphatic)$_2$, —OC(O)NH($C_{1-6}$ aliphatic), —C(O)C(O)($C_{1-6}$ aliphatic), —C(O)$CH_2$C(O)($C_{1-6}$ aliphatic), —S(O)$_2$($C_{1-6}$ aliphatic), —S(O)$_2$O($C_{1-6}$ aliphatic), —OS(O)$_2$($C_{1-6}$ aliphatic), —S(O)$_2$NH($C_{1-6}$ aliphatic), —S(O)($C_{1-6}$ aliphatic), —NHS(O)$_2$NH($C_{1-6}$ aliphatic), —NHS(O)$_2$($C_{1-6}$ aliphatic), —P(O)$_2$($C_{1-6}$ aliphatic), —P(O)($C_{1-6}$ aliphatic)$_2$, —OP(O)($C_{1-6}$ aliphatic)$_2$, or —OP(O)(O$C_{1-6}$ aliphatic)$_2$.

Suitable substitutents on $R^x$ further include bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, $R^x$ is hydrogen.

In certain embodiments, $R^x$ is $N_3$.

In other embodiments, $R^x$ is an epoxide ring.

In certain embodiments, $R^x$ is methyl. In other embodiments, $R^x$ is —$NH_2$.

In certain embodiments, the $R^x$ group of formula IIa is a crown ether. Examples of such crown ethers include 12-crown-4, 15-crown-5, and 18-crown-6.

In still other embodiments, $R^x$ is a detectable moiety. Detectable moieties are known in the art and include those described herein. According to one aspect of the invention, the $R^x$ group of formula IIa is a fluorescent moiety. Such fluorescent moieties are well known in the art and include coumarins, quinolones, benzoisoquinolones, hostasol, and Rhodamine dyes, to name but a few. Exemplary fluorescent moieties of $R^x$ include anthracen-9-yl, pyren-4-yl, 9-H-carbazol-9-yl, the carboxylate of rhodamine B, and the carboxylate of coumarin 343. In certain embodiments, $R^x$ is a detectable moiety selected from:

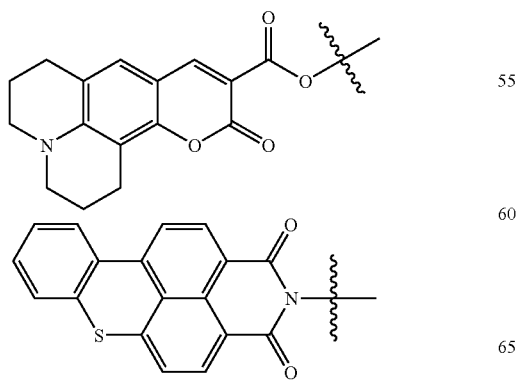

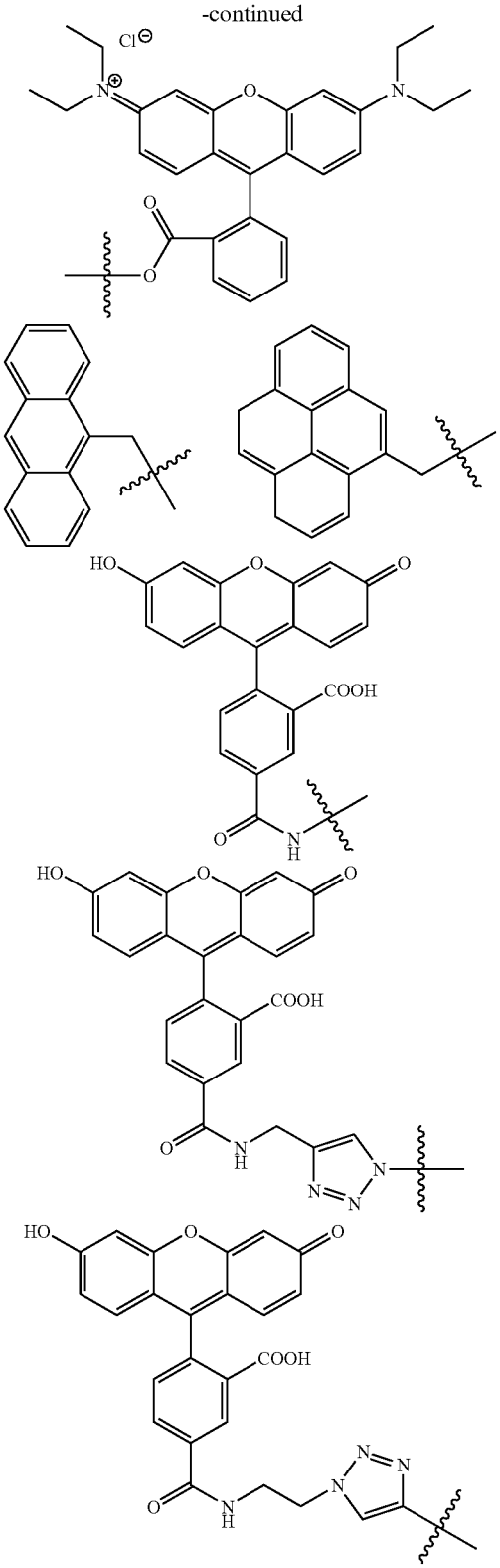

wherein each eavy line indicates the point of attachment to the rest of the molecule.

In certain embodiments, $R^x$ is —P(O)(OR)$_2$, or —P(O)(X)$_2$. According to one aspect, the present invention provides a compound of formula IIa, wherein $R^x$ is —P(O)(OH)$_2$. According to another aspect, the present invention provides a compound of formula IIa, wherein $R^x$ is —P(O)(Cl)$_2$.

As defined generally above, the $L^x$ group of formula IIa is a valence bond or a bivalent, saturated or unsaturated, straight or branched $C_{1-12}$ hydrocarbon chain, wherein 0-6 methylene units of $L^x$ are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the $L^x$ group of formula IIa is a valence bond. In other embodiments, $L^x$ a bivalent, saturated $C_{1-12}$ hydrocarbon chain, wherein 0-6 methylene units of $L^x$ are independently replaced by -Cy-, —O—, —NH—, —S—, —OC(O)—, —C(O)O—, —C(O)—, —C(O)NH—, or —NHC(O)—, wherein -Cy- is an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In still other embodiments, $L^x$ a bivalent, saturated $C_{1-6}$ alkylene chain, wherein 0-3 methylene units of $L^x$ are independently replaced by -Cy-, —O—, —NH—, —S—, —OC(O)—, —C(O)O—, —C(O)—, —C(O)NH—, or —NHC(O)—, In certain embodiments, $L^x$ is -Cy- (i.e. a $C_1$ alkylene chain wherein the methylene unit is replaced by -Cy-), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $L^x$ group of formula IIa is —O—, —S—, —NH—, or —C(O)O—. In other embodiments, the $L^x$ group of formula IIa is -Cy-, —C(O)—, —C(O)NH—, —NHC(O)—, —NH—O—, or —O-Cy-CH$_2$NH—O—. In still other embodiments, the $L^x$ group of formula IIa is any of —OCH$_2$—, —OCH$_2$C(O)—, —OCH$_2$CH$_2$C(O)—, —OCH$_2$CH$_2$O—, —OCH$_2$CH$_2$S—, —OCH$_2$CH$_2$C(O)O—, —OCH$_2$CH$_2$NH—, —OCH$_2$CH$_2$NHC(O)—, —OCH$_2$CH$_2$C(O)NH—, and —NHC(O)CH$_2$CH$_2$C(O)O—. According to another aspect, the $L^x$ group of formula IIa is any of —OCH$_2$CH$_2$NHC(O)CH$_2$CH$_2$C(O)O—, —OCH$_2$CH$_2$NHC(O)CH$_2$OCH$_2$C(O)O—, —OCH$_2$CH$_2$NHC(O)CH$_2$OCH$_2$C(O)NH—, —CH$_2$C(O)NH—, —CH$_2$C(O)NHNH—, or —OCH$_2$CH$_2$NHNH—. Exemplary $L^x$ groups of formula IIa include any of those depicted in any of Tables 1 through 25.

According to another aspect of the present invention, a functional group formed by the -$L^x$-$R^x$ moiety of formula IIa is optionally protected. Thus, in certain embodiments, the -$L^x$-$R^x$ moiety of formula IIa optionally comprises a mono-protected amine, a di-protected amine, a protected aldehyde, a protected hydroxyl, a protected carboxylic acid, or a protected thiol group. Such groups include those described above with respect to the -$L^1$-R1 moiety of formula I.

According to yet another aspect of the present invention, the $R^2$ group of formula I is —P(O)(X)$_2$. Accordingly, the present invention provides a compound of formula IIb:

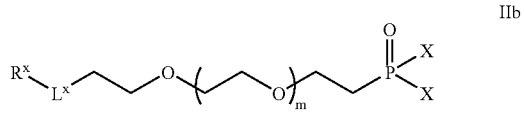

IIb or a salt thereof, wherein:

m is 10-2500;

each X is independently halogen;

$R^x$ is hydrogen, halogen, NO$_2$, CN, N$_3$, —N═C═O, —C(R)═NN(R)$_2$, —P(O)(OR)$_2$, —P(O)(X)$_2$, a 9-30 membered crown ether, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each R is independently hydrogen or an optionally substituted group selected from aliphatic or a a 3-8 membered saturated, partially unsaturated, or aryl ring having 0-4 heteroatoms independently selected from nitrogen, oxygen, or sulfur;

$L^x$ is a valence bond or a bivalent, saturated or unsaturated, straight or branched $C_{1-12}$ hydrocarbon chain, wherein 0-6 methylene units of $L^x$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

As defined generally above, the m group of formula IIb is 10-2500. In certain embodiments, the present invention provides compounds of formula IIb, as described above, wherein m is about 225. In other embodiments, m is about 10 to about 40. In other embodiments, m is about 40 to about 60. In other embodiments, m is about 60 to about 90. In still other embodiments, m is about 90 to about 150. In other embodiments, m is about 150 to about 200. In still other embodiments, m is about 200 to about 250. In other embodiments, m is about 300 to about 375. In other embodiments, m is about 400 to about 500. In still other embodiments, m is about 650 to about 750.

According to another embodiment, the present invention provides a compound of formula IIb, as described above, wherein said compound has a polydispersity index ("PDI") of about 1.0 to about 1.2. According to another embodiment, the present invention provides a compound of formula IIb, as described above, wherein said compound has a polydispersity index ("PDI") of about 1.02 to about 1.05. According to yet another embodiment, the present invention provides a compound of formula IIb, as described above, wherein said compound has a polydispersity index ("PDI") of about 1.05 to about 1.10. In other embodiments, said compound has a PDI of about 1.01 to about 1.03. In other embodiments, said compound has a PDI of about 1.10 to about 1.15. In still other embodiments, said compound has a PDI of about 1.15 to about 1.20.

In other embodiments, the present invention provides a compound of formula IIb, as described above, wherein -$L^x$-$R^x$ is a hydroxyl group.

As defined generally above, the $R^x$ of formula IIb is hydrogen, halogen, $NO_2$, CN, $N_3$, —N=C=O, —C(R)=NN(R)$_2$, —P(O)(OR)$_2$, —P(O)(X)$_2$, a 9-30-membered crown ether, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; wherein each R is independently hydrogen or an optionally substituted aliphatic group.

In certain embodiments, the $R^x$ group of formula IIb is optionally substituted aliphatic. In other embodiments, $R^x$ is an unsubstituted aliphatic. In some embodiments, said $R^x$ moiety is an optionally substituted alkyl group. In other embodiments, said $R^x$ moiety is an optionally substituted alkynyl or alkenyl group. Such groups include t-butyl, 5-norbornene-2-yl, octane-5-yl, —C≡CH, —CH$_2$C≡CH, —CH$_2$CH$_2$C≡CH, and —CH$_2$CH$_2$CH$_2$C≡CH. When said $R^x$ moiety is a substituted aliphatic group, suitable substituents on $R^x$ include any of CN, $N_3$, $NO_2$, —CO$_2$H, —SH, —NH$_2$, —C(O)H, —NHC(O)$R^o$, —NHC(S)$R^o$, —NHC(O)N$R^o{}_2$, —NHC(S)N$R^o{}_2$, —NHC(O)O$R^o$, —NHNHC(O)$R^o$, —NHNHC(O)N$R^o{}_2$, —NHNHC(O)O$R^o$, —C(O)$R^o$, —C(S)$R^o$, —C(O)O$R^o$, —C(O)S$R^o$, —C(O)OSi$R^o{}_3$, —OC(O)$R^o$, SC(S)S$R^o$, —SC(O)$R^o$, —C(O)N($R^o$)$_2$, —C(S)N($R^o$)$_2$, —C(S)S$R^o$, —SC(S)S$R^o$, —OC(O)N($R^o$)$_2$, —C(O)NHN($R^o$)$_2$, —C(O)N(O$R^o$)$R^o$, —C(O)C(O)$R^o$, —C(O)CH$_2$C(O)$R^o$, —C(NO$R^o$)$R^o$, —SS$R^o$, —S(O)$_2$$R^o$, —S(O)$_2$O$R^o$, —OS(O)$_2$$R^o$, —S(O)$_2$N($R^o$)$_2$, —S(O)$R^o$, —N($R^o$)S(O)$_2$N($R^o$)$_2$, —N($R^o$)S(O)$_2$$R^o$, —N(O$R^o$)$R^o$, —C(NH)N($R^o$)$_2$, —P(O)$_2$$R^o$, —P(O)($R^o$)$_2$, —OP(O)($R^o$)$_2$, or —OP(O)(O$R^o$)$_2$, wherein each $R^o$ is as defined herein.

In other embodiments, $R^x$ is an aliphatic group optionally substituted with any of Cl, Br, I, F, —NH$_2$, —OH, —SH, —CO$_2$H, —C(O)H, —C(O)(C$_{1-6}$ aliphatic), —NHC(O)(C$_{1-6}$ aliphatic), —NHC(O)NH$_2$, —NHC(O)NH(C$_{1-6}$ aliphatic), —NHC(S)NH—, —NHC(S)N(C$_{1-6}$ aliphatic)$_2$, —NHC(O)O(C$_{1-6}$ aliphatic), —NHNH$_2$, —NHNHC(O)(C$_{1-6}$ aliphatic), —NHNHC(O)NH$_2$, —NHNHC(O)NH(C$_{1-6}$ aliphatic), —NHNHC(O)O(C$_{1-6}$ aliphatic), —C(O)NH$_2$, —C(O)NH(C$_{1-6}$ aliphatic)$_2$, —C(O)NHNH$_2$, —C(S)N(C$_{1-6}$ aliphatic)$_2$, —OC(O)NH(C$_{1-6}$ aliphatic), —C(O)C(O)(C$_{1-6}$ aliphatic), —C(O)CH$_2$C(O)(C$_{1-6}$ aliphatic), —S(O)$_2$(C$_{1-6}$ aliphatic), —S(O)$_2$O(C$_{1-6}$ aliphatic), —OS(O)$_2$(C$_{1-6}$ aliphatic), —S(O)$_2$NH(C$_{1-6}$ aliphatic), —S(O)(C$_{1-6}$ aliphatic), —NHS(O)$_2$NH(C$_{1-6}$ aliphatic), —NHS(O)$_2$(C$_{1-6}$ aliphatic), —P(O)$_2$(C$_{1-6}$ aliphatic), —P(O)(C$_{1-6}$ aliphatic)$_2$, —OP(O)(C$_{1-6}$ aliphatic)$_2$, or —OP(O)(OC$_{1-6}$ aliphatic)$_2$. In other embodiments, the $R^x$ group of formula IIb is an optionally substituted aliphatic group having substituents as depicted for $R^1$ in any of Tables 1 through 25.

In certain embodiments, the $R^x$ group of formula IIb is a group suitable for Click chemistry. Click reactions tend to involve high-energy ("spring-loaded") reagents with well-defined reaction coordinates, that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition is one such reaction. Click chemistry is known in the art and one of ordinary skill in the art would recognize that certain $R^x$ moieties of the present invention are suitable for Click chemistry.

According to one embodiment, the $R^x$ group of formula IIb is an azide-containing group. According to another embodiment, the $R^x$ group of formula IIb is an alkyne-containing group. In certain embodiments, the $R^x$ group of formula IIb has a terminal alkyne moiety. According to another embodiment, the $R^x$ group of formula IIb is an aldehyde-containing group. In certain embodiments, the $R^x$ group of formula IIb has a terminal hydrazine moiety. In other embodiments, the $R^x$ group of formula IIb has a terminal oxyamine moiety. In still other embodiments, the $R^x$ group of formula IIb is a epoxide-containing group. In certain other embodiments, the $R^x$ group of formula IIb has a terminal maleimide moiety.

In other embodiments, $R^x$ is an optionally substituted 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur. In certain embodiments, $R^x$ is an optionally substituted 5-7 membered saturated or partially unsaturated ring having 0-4 heteroatoms independently selected from nitrogen, oxygen, or sulfur. In other embodiments, $R^x$ is an optionally substituted phenyl ring or a 5-6 membered heteroaryl ring having 1-4 heteroatoms independently selected from nitrogen, oxygen, or sulfur.

In certain embodiments, the $R^x$ group of formula IIb is an optionally substituted aryl group. Examples include optionally substituted phenyl, optionally substituted pyridyl, optionally substituted naphthyl, optionally substituted pyrenyl, optionally substituted triazole, optionally substituted imidazole, optionally substituted phthalimide, optionally substituted tetrazole, optionally substituted furan, and optionally substituted pyran. When said $R^x$ moiety is a substituted aryl group, suitable substituents on $R^x$ include $R^o$, CN, $N_3$, $NO_2$, —CH$_3$, —CH$_2$N$_3$, t-butyl, 5-norbornene-2-yl, octane-5-yl, —CH=CH$_2$, —C≡CH, —CH$_2$C≡CH, —CH$_2$CH$_2$C≡CH, —CH$_2$CH$_2$CH$_2$C≡CH, Cl, Br, I, F, —NH$_2$, —OH, —SH, —CO$_2$H, —C(O)H, —CH$_2$NH$_2$, —CH$_2$OH, —CH$_2$SH, —CH$_2$CO$_2$H, —CH$_2$C(O)H, —C(O)(C$_{1-6}$ aliphatic), —NHC(O)(C$_{1-6}$ aliphatic), —NHC(O)NH—, —NHC(O)NH(C$_{1-6}$ aliphatic), —NHC(S)NH$_2$, —NHC(S)N(C$_{1-6}$ aliphatic)$_2$, —NHC(O)O(C$_{1-6}$ aliphatic), —NHNH$_2$, —NHNHC(O)(C$_{1-6}$ aliphatic), —NHNHC(O)NH$_2$, —NHNHC(O)NH(C$_{1-6}$ aliphatic), —NHNHC(O)O(C$_{1-6}$ aliphatic), —C(O)NH$_2$, —C(O)NH(C$_{1-6}$ aliphatic)$_2$, —C(O)NHNH$_2$, —C(S)N(C$_{1-6}$ aliphatic)$_2$, —OC(O)NH(C$_{1-6}$ aliphatic), —C(O)C(O)(C$_{1-6}$ aliphatic), —C(O)CH$_2$C(O)(C$_{1-6}$ aliphatic), —S(O)$_2$(C$_{1-6}$ aliphatic), —S(O)$_2$O(C$_{1-6}$ aliphatic), —OS(O)$_2$(C$_{1-6}$ aliphatic), —S(O)$_2$NH(C$_{1-6}$ aliphatic), —S(O)(C$_{1-6}$ aliphatic), —NHS(O)$_2$NH(C$_{1-6}$ aliphatic), —NHS(O)$_2$(C$_{1-6}$ aliphatic), —P(O)$_2$(C$_{1-6}$ aliphatic), —P(O)(C$_{1-6}$ aliphatic)$_2$, —OP(O)(C$_{1-6}$ aliphatic)$_2$, or —OP(O)(OC$_{1-6}$ aliphatic)$_2$.

Suitable substituents on $R^x$ further include bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, $R^x$ is hydrogen.

In certain embodiments, $R^x$ is $N_3$.

In certain embodiments, $R^x$ is an epoxide ring.

In certain embodiments, $R^x$ is methyl. In other embodiments, $R^x$ is —$NH_2$.

In certain embodiments, the $R^x$ group of formula IIb is a crown ether. Examples of such crown ethers include 12-crown-4, 15-crown-5, and 18-crown-6.

In still other embodiments, $R^x$ is a detectable moiety. Detectable moieties are known in the art and include those described herein. According to one aspect of the invention, the $R^x$ group of formula IIb is a fluorescent moiety. Such fluorescent moieties are well known in the art and include coumarins, quinolones, benzoisoquinolones, hostasol, and Rhodamine dyes, to name but a few. Exemplary fluorescent moieties of $R^x$ include anthracen-9-yl, pyren-4-yl, 9-H-carbazol-9-yl, the carboxylate of rhodamine B, and the carboxylate of coumarin 343. In certain embodiments, $R^x$ is a detectable moiety selected from:

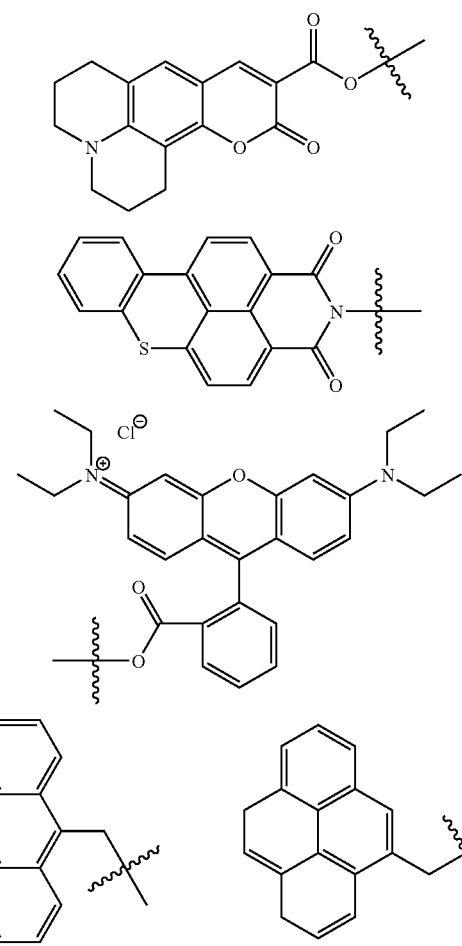

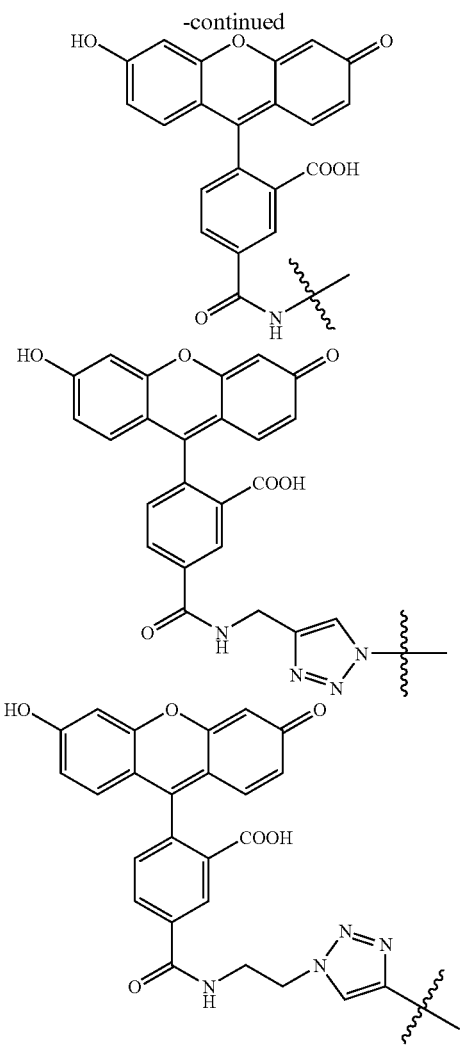

wherein each wavy line indicates the point of attachment to the rest of the molecule.

In certain embodiments, $R^x$ is —$P(O)(OR)_2$, or —$P(O)(X)_2$. According to one aspect, the present invention provides a compound of formula IIb, wherein $R^x$ is —$P(O)(OH)_2$. According to another aspect, the present invention provides a compound of formula IIb, wherein $R^x$ is —$P(O)(Cl)_2$.

As defined generally above, the $L^x$ group of formula IIb is a valence bond or a bivalent, saturated or unsaturated, straight or branched $C_{1-12}$ hydrocarbon chain, wherein 0-6 methylene units of $L^x$ are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the $L^x$ group of formula IIb is a valence bond. In other embodiments, $L^x$ a bivalent, saturated $C_{1-12}$ hydrocarbon chain, wherein 0-6 methylene units of $L^x$ are independently replaced by -Cy-, —O—, —NH—, —S—, —OC(O)—, —C(O)O—, —C(O)—, —C(O)NH—, or —NHC(O)—, wherein -Cy- is an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In still other embodiments, $L^x$ a bivalent, saturated $C_{1-6}$ alkylene chain, wherein 0-3 methylene units of $L^x$ are independently replaced by -Cy-, —O—, —NH—, —S—, —OC(O)—, —C(O)O—, —C(O)—, —C(O)NH—, or —NHC(O)—.

In certain embodiments, $L^x$ is -Cy- (i.e. a $C_1$ alkylene chain wherein the methylene unit is replaced by -Cy-), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $L^x$ group of formula IIb is —O—, —S—, —NH—, or —C(O)O—. In other embodiments, the $L^x$ group of formula IIb is -Cy-, —C(O)—, —C(O)NH—, —NHC(O)—, —NH—O—, or —O-Cy-CH$_2$NH—O—. In still other embodiments, the $L^x$ group of formula IIb is any of —OCH$_2$—, —OCH$_2$C(O)—, —OCH$_2$CH$_2$C(O)—, —OCH$_2$CH$_2$O—, —OCH$_2$CH$_2$S—, —OCH$_2$CH$_2$C(O)O—, —OCH$_2$CH$_2$NH—, —OCH$_2$CH$_2$NHC(O)—, —OCH$_2$CH$_2$C(O)NH—, and —NHC(O)CH$_2$CH$_2$C(O)O—. According to another aspect, the $L^x$ group of formula IIb is any of —OCH$_2$CH$_2$NHC(O)CH$_2$CH$_2$C(O)O—, —OCH$_2$CH$_2$NHC(O)CH$_2$OCH$_2$C(O)O—, —OCH$_2$CH$_2$NHC(O)CH$_2$OCH$_2$C(O)NH—, —CH$_2$C(O)NH—, —CH$_2$C(O)NHNH—, or —OCH$_2$CH$_2$NHNH—. Exemplary $L^x$ groups of formula IIb include any of those depicted in any of Tables 1 through 25.

According to another aspect of the present invention, a functional group formed by the -$L^x$-$R^x$ moiety of formula IIb is optionally protected. Thus, in certain embodiments, the -$L^x$-$R^x$ moiety of formula IIb optionally comprises a mono-protected amine, a di-protected amine, a protected aldehyde, a protected hydroxyl, a protected carboxylic acid, or a protected thiol group. Such groups include those described above with respect to the -$L^1$-$R^1$ moiety of formula I.

Exemplary compounds of formula IIa and IIb are set forth in Tables 1 through 25.

According to another embodiment, the present invention provides a compound of either of formulae IIIa or IIIb:

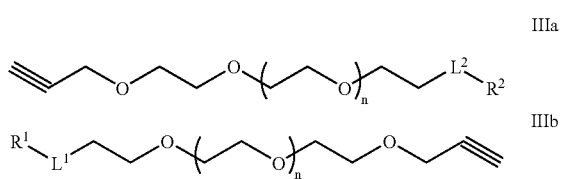

or a salt thereof, wherein n, $L^1$, $L^2$, $R^1$, and $R^2$ are as defined above and described in classes and subclasses herein, singly and in combination.

Yet another embodiment relates to a compound of either of formulae IVa or IVb:

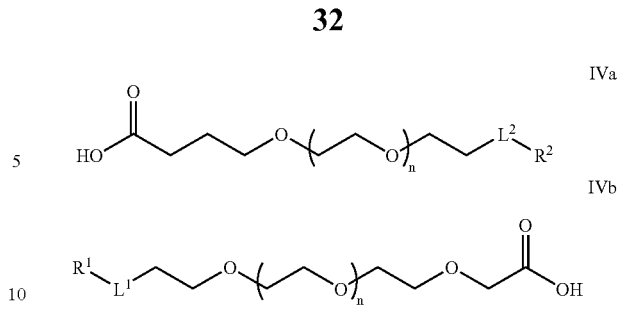

or a salt thereof, wherein n, $L^1$, $L^2$, $R^1$, and $R^2$ are as defined above and described in classes and subclasses herein, singly and in combination.

Yet another embodiment relates to a compound of either of formulae Va or Vb:

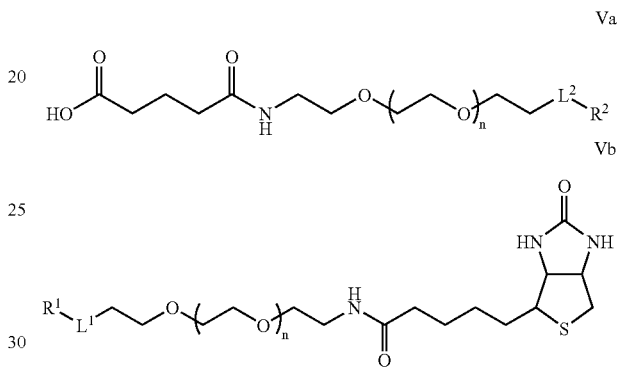

or a salt thereof, wherein n, $L^1$, $L^2$, $R^1$, and $R^2$ are as defined above and described in classes and subclasses herein, singly and in combination.

In certain embodiments, the present invention provides a compound of either of formulae VIa or VIb:

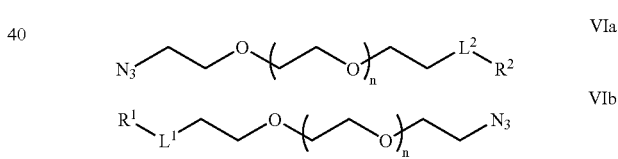

or a salt thereof, wherein n, $L^1$, $L^2$, $R^1$, and $R^2$ are as defined above and described in classes and subclasses herein, singly and in combination.

In other embodiments, the present invention provides a compound of either of formulae VIIa or VIIb:

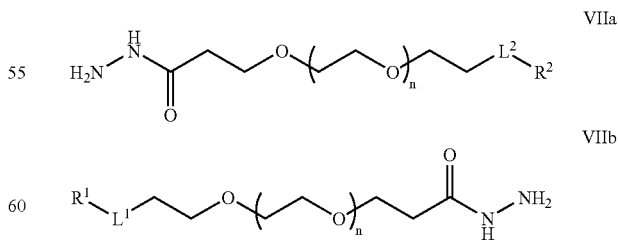

or a salt thereof, wherein n, $L^1$, $L^2$, $R^1$, and $R^2$ are as defined above and described in classes and subclasses herein, singly and in combination.

In still other embodiments, the present invention provides a compound of either of formulae VIIIa or VIIIb:

VIIIa

[Structure: H₂N-CH₂CH₂-O-(CH₂CH₂O)ₙ-CH₂CH₂-L²-R²]

VIIIb

[Structure: R¹-L¹-CH₂CH₂-O-(CH₂CH₂O)ₙ-CH₂CH₂-NH₂]

or a salt thereof, wherein n, L¹, L², R¹, and R² are as defined above and described in classes and subclasses herein, singly and in combination.

According to another embodiment, the present invention provides a compound of either of formulae IXa or IXb:

IXa

[Maleimide-N-CH₂CH₂-O-(CH₂CH₂O)ₙ-CH₂CH₂-L²-R²]

IXb

[R¹-L¹-CH₂CH₂-O-(CH₂CH₂O)ₙ-CH₂CH₂-N-maleimide]

or a salt thereof, wherein n, L¹, L², R¹, and R² are as defined above and described in classes and subclasses herein, singly and in combination.

According to yet another embodiment, the present invention provides a compound of either of formulae Xa or Xb:

Xa

[HS-CH₂CH₂-O-(CH₂CH₂O)ₙ-CH₂CH₂-L²-R²]

Xb

[R¹-L¹-CH₂CH₂-O-(CH₂CH₂O)ₙ-CH₂CH₂-SH]

or a salt thereof, wherein n, L¹, L², R¹, and R² are as defined above and described in classes and subclasses herein, singly and in combination.

In certain embodiments, the present invention provides a compound of any of formulae XIa, XIb, XIc, XId, XIe, or XIf:

XIa

[HOOC-C₆H₄-O-CH₂CH₂-O-(CH₂CH₂O)ₙ-CH₂CH₂-L²-R²]

XIb

[R¹-L¹-CH₂CH₂-O-(CH₂CH₂O)ₙ-CH₂CH₂-O-C₆H₄-COOH]

XIc

[H₂N-C₆H₄-O-CH₂CH₂-O-(CH₂CH₂O)ₙ-CH₂CH₂-L²-R²]

XId

[R¹-L¹-CH₂CH₂-O-(CH₂CH₂O)ₙ-CH₂CH₂-O-C₆H₄-NH₂]

XIe

[OHC-C₆H₄-O-CH₂CH₂-O-(CH₂CH₂O)ₙ-CH₂CH₂-L²-R²]

XIf

[R¹-L¹-CH₂CH₂-O-(CH₂CH₂O)ₙ-CH₂CH₂-O-C₆H₄-CHO]

or a salt thereof, wherein n, L¹, L², R¹, and R² are as defined above and described in classes and subclasses herein, singly and in combination.

In certain embodiments, the present invention provides a compound as described herein, wherein $R^1$ is a $C_{1-6}$ aliphatic substituted with —$CO_2H$. Exemplary compounds include those set forth in Table 1, wherein n is as described in classes and subclasses herein. In certain embodiments, n is selected from 50±10. In other embodiments, n is selected from 80±10, 115±10, 180±10, or 225±10.

TABLE 1

Exemplary Compounds

[Structure: $R^a$-O-(CH₂CH₂O)ₙ-$R^b$]

| # | $R^a$ | $R^b$ |
|---|---|---|
| 1 | HOOC-CH₂CH₂CH₂-··· | ···-CH₂CH₂-S-C(C₆H₅)₃ |

TABLE 1-continued
Exemplary Compounds
$$R^a\text{-}O\text{-}(CH_2CH_2O)_n\text{-}R^b$$
| # | $R^a$ | $R^b$ |
|---|-------|-------|
| 2 | 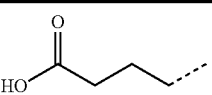 |  |
| 3 | 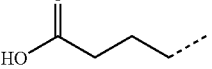 | 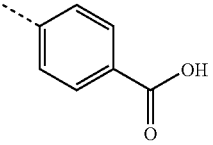 |
| 4 | 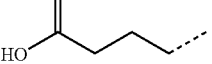 | 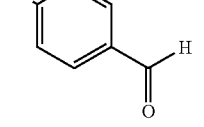 |
| 5 | 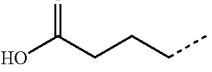 | 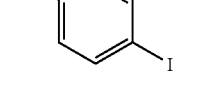 |
| 6 | 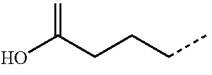 | 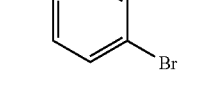 |
| 7 | 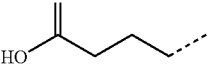 | 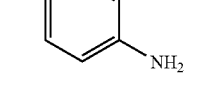 |
| 8 | 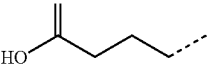 | 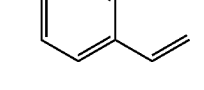 |
| 9 | 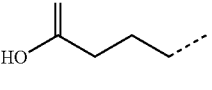 | 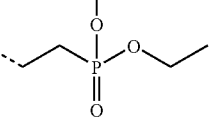 |
| 10 | 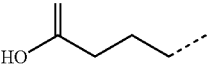 | 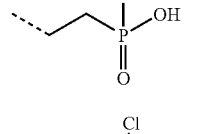 |
| 11 | 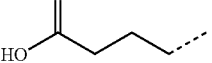 | 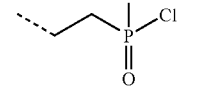 |
| 12 | 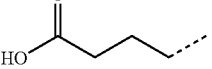 | 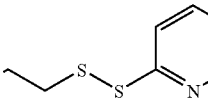 |

TABLE 1-continued

Exemplary Compounds $$R^a-O-(\!\!-\!\!O\!\!-\!\!)_n\!\!-\!\!R^b$$

| # | $R^a$ | $R^b$ |
|---|---|---|
| 13 | HOOC-CH2CH2CH2- | -CH2CH2-NH-C(O)-CH=CH2 |
| 14 | HOOC-CH2CH2CH2- | -CH2CH2-NH-C(O)-C(CH3)=CH2 |
| 15 | HOOC-CH2CH2CH2- | -CH2CH2-NH-C(O)-norbornenyl |
| 16 | HOOC-CH2CH2CH2- | -C6H4-CH2-NH2 |
| 17 | HOOC-CH2CH2CH2- | -C6H4-CH2-SH |
| 18 | HOOC-CH2CH2CH2- | -CH2CH2-maleimide |
| 19 | HOOC-CH2CH2CH2- | -CH2CH2-SH |
| 20 | HOOC-CH2CH2CH2- | -CH2CH2-NH2 |
| 21 | HOOC-CH2CH2CH2- | -CH2CH2-O-C(O)-CH2CH2-C≡CH |
| 22 | HOOC-CH2CH2CH2- | -CH2CH2-NH-C(O)-CH2CH2-C≡CH |

TABLE 1-continued

Exemplary Compounds

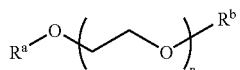

| # | $R^a$ | $R^b$ |
|---|---|---|
| 23 | 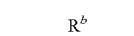 | 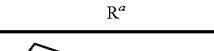 |
| 24 | | |
| 25 | | |
| 26 | | |

In certain embodiments, the present invention provides a compound as described herein, wherein $R^1$ is a $C_{1-6}$ aliphatic substituted with oxazolinyl. Exemplary compounds include those set forth in Table 2, wherein n is as described in classes and subclasses herein. In certain embodiments, n is selected from 50±10. In other embodiments, n is selected from 80±10, 115±10, 180±10, or 225±10.

TABLE 2

Exemplary Compounds

| # | $R^a$ | $R^b$ |
|---|---|---|
| 27 |  | SH |
| 28 | | NH$_2$ |
| 29 | |  |

In certain embodiments, the present invention provides a compound as described herein, wherein $L^1$ is a $C_{1-6}$ alkylene wherein two methylene units of $L^1$ are substituted with —C(O)NH— and —C(O)O—, and $R^1$ is hydrogen. Exemplary compounds include those set forth in Table 3, wherein n is as described in classes and subclasses herein. In certain embodiments, n is selected from 50±10. In other embodiments, n is selected from 80±10, 115±10, 180±10, or 225±10.

TABLE 3
Exemplary Compounds
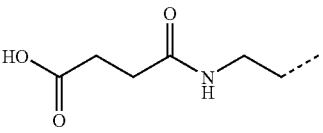
| # | $R^a$ | $R^b$ |
|---|---|---|
| 30 | 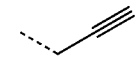 | 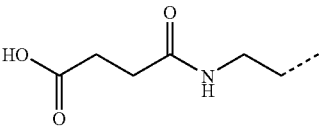 |
| 31 | 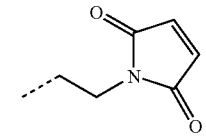 | 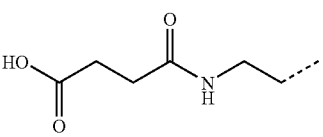 |
| 32 | 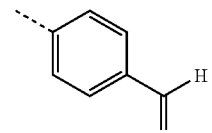 | 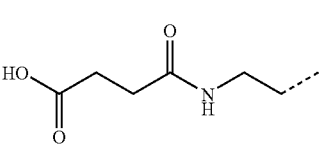 |
| 33 | 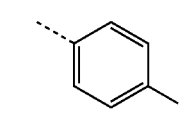 | 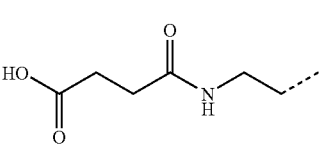 |
| 34 | 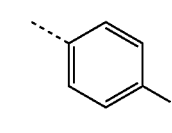 | 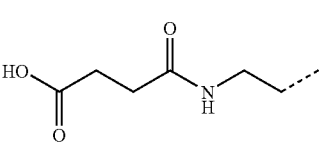 |
| 35 | 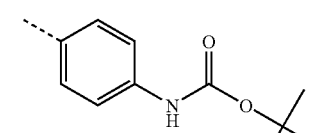 | 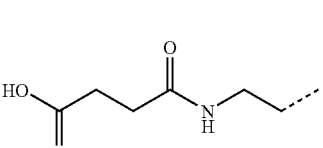 |
| 36 | 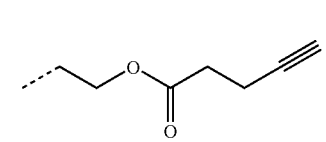 | 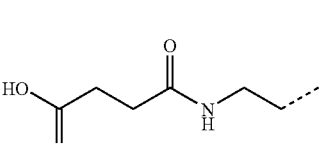 |
| 37 | 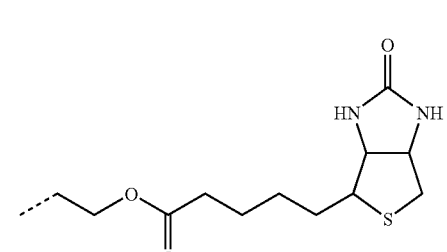 | 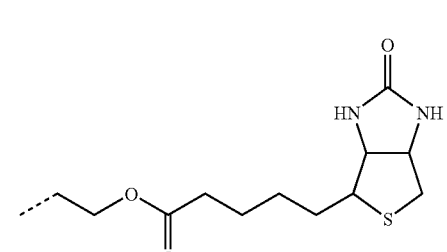 |

TABLE 3-continued
Exemplary Compounds
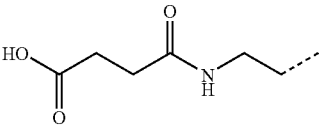
| # | R^a | R^b |
|---|---|---|
| 38 | 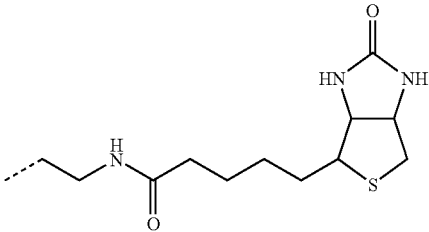 | 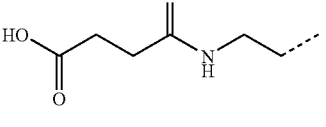 |
| 39 | 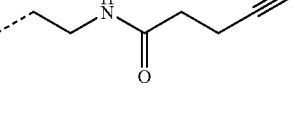 | 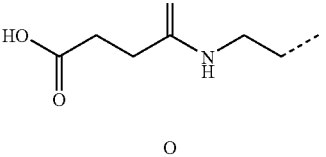 |
| 40 | 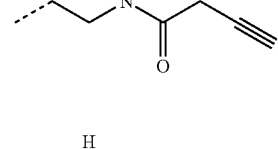 | 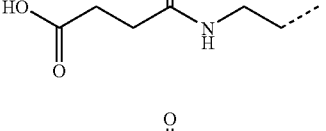 |
| 41 | 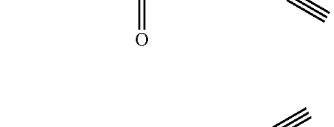 | 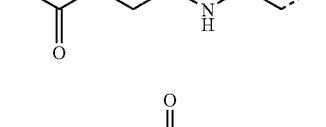 |
| 42 | 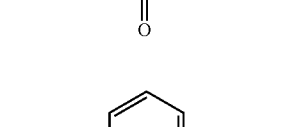 |  |
| 43 | 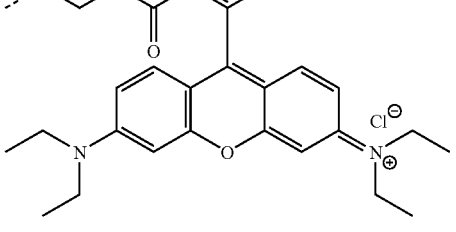 | 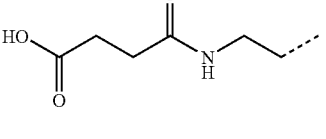 |
| 44 | 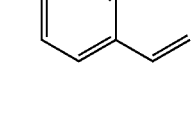 | 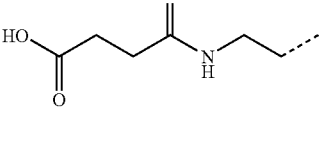 |
| 45 | 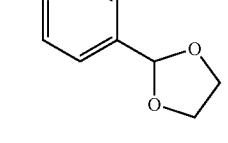 | |

TABLE 3-continued
Exemplary Compounds
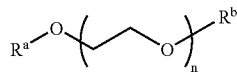
| # | $R^a$ | $R^b$ |
|---|---|---|
| 46 | 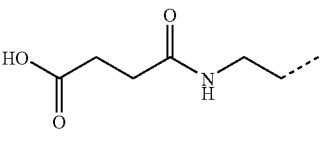 | 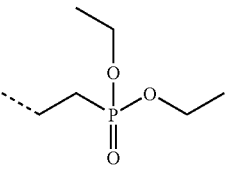 |
| 47 | 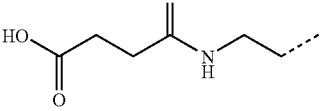 | 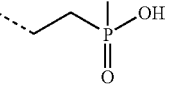 |
| 48 | 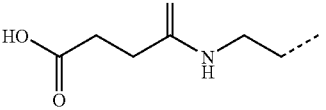 | 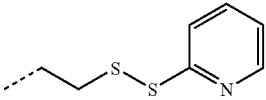 |
| 49 | 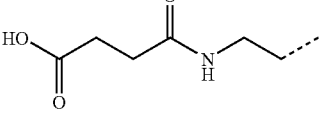 | 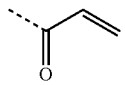 |
| 50 | 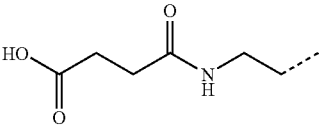 | 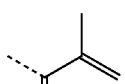 |
| 51 | 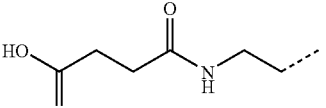 | 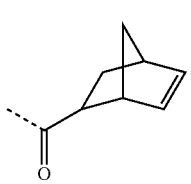 |
| 52 | 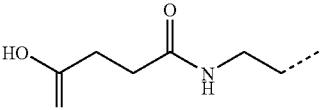 | 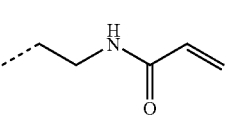 |
| 53 | 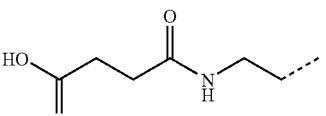 | 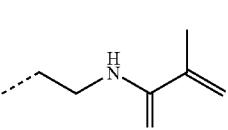 |
| 54 | 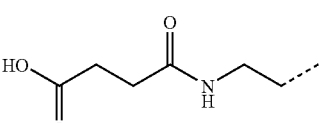 | 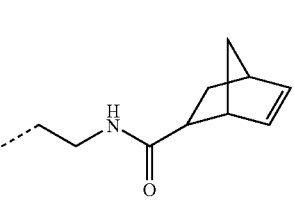 |

TABLE 3-continued

Exemplary Compounds $$R^a-O-(\phantom{xx}O\phantom{xx})_n-R^b$$

| # | $R^a$ | $R^b$ |
|---|-------|-------|
| 55 | HOOC-CH₂CH₂-C(O)-NH-CH₂CH₂- | -C(O)-C≡CH |
| 56 | HOOC-CH₂CH₂-C(O)-NH-CH₂CH₂- | -CH₂CH₂-NH-C(O)-C≡CH |
| 57 | HOOC-CH₂CH₂CH₂-C(O)-NH-CH₂CH₂- | -CH₂CH₂-C≡CH |
| 58 | HOOC-CH₂CH₂CH₂-C(O)-NH-CH₂CH₂- | -CH₂CH₂-N(maleimide) |
| 59 | HOOC-CH₂CH₂CH₂-C(O)-NH-CH₂CH₂- | -C₆H₄-CHO (para) |
| 60 | HOOC-CH₂CH₂CH₂-C(O)-NH-CH₂CH₂- | -C₆H₄-I (para) |
| 61 | HOOC-CH₂CH₂CH₂-C(O)-NH-CH₂CH₂- | -C₆H₄-Br (para) |
| 62 | HOOC-CH₂CH₂CH₂-C(O)-NH-CH₂CH₂- | -C₆H₄-NH-C(O)-O-C(CH₃)₃ (para) |
| 63 | HOOC-CH₂CH₂CH₂-C(O)-NH-CH₂CH₂- | -CH₂CH₂-O-C(O)-CH₂CH₂-C≡CH |

TABLE 3-continued

Exemplary Compounds $$R^a-O-(\phantom{x}\diagup\diagdown O\phantom{x})_n-R^b$$

| # | $R^a$ | $R^b$ |
|---|---|---|
| 64 | HOOC-CH2CH2CH2-C(O)-NH-CH2CH2- | -CH2CH2-O-C(O)-(CH2)4-biotinyl |
| 65 | HOOC-CH2CH2CH2-C(O)-NH-CH2CH2- | -CH2CH2-NH-C(O)-(CH2)4-biotinyl |
| 66 | HOOC-CH2CH2CH2-C(O)-NH-CH2CH2- | -CH2CH2-NH-C(O)-CH2CH2-C≡CH |
| 67 | HOOC-CH2CH2CH2-C(O)-NH-CH2CH2- | -CH2CH2-NH-C(O)-CH2-C≡CH |
| 68 | HOOC-CH2CH2CH2-C(O)-NH-CH2CH2- | -CH2CH2-NH-C(O)-CH2CH2CH2-C≡CH |
| 69 | HOOC-CH2CH2CH2-C(O)-NH-CH2CH2- | -CH2CH2-O-C(O)-CH2CH2-C≡CH |
| 70 | HOOC-CH2CH2CH2-C(O)-NH-CH2CH2- | -CH2CH2-O-C(O)-(rhodamine B) Cl⁻ |
| 71 | HOOC-CH2CH2CH2-C(O)-NH-CH2CH2- | -(4-vinylphenyl) |

TABLE 3-continued
Exemplary Compounds
$$R^a\text{—}O\text{—}(\text{—}O\text{—})_n\text{—}R^b$$
| # | R$^a$ | R$^b$ |
|---|---|---|
| 72 | 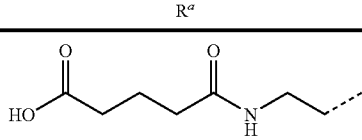 | 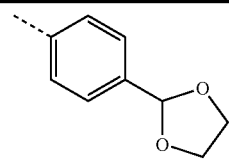 |
| 73 | 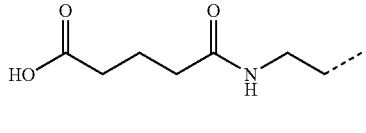 | 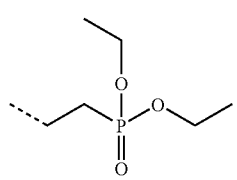 |
| 74 | 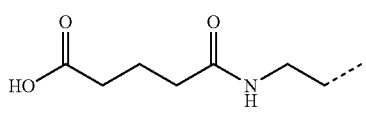 | 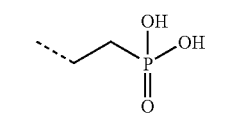 |
| 75 | 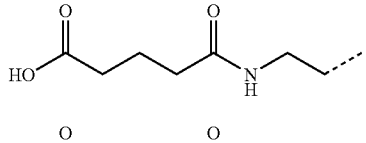 | 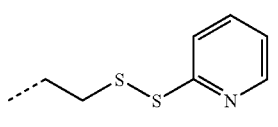 |
| 76 | 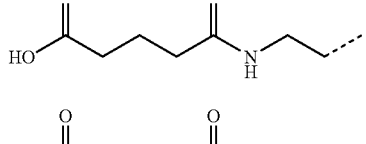 | 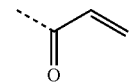 |
| 77 | 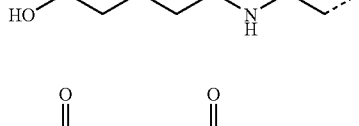 | 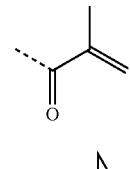 |
| 78 | 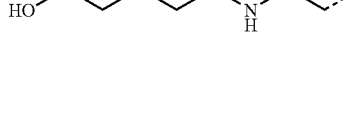 | 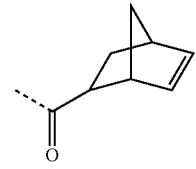 |
| 79 | 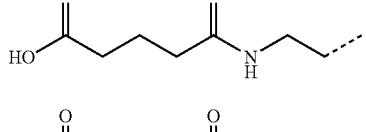 | 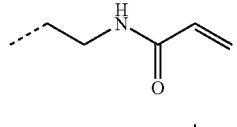 |
| 80 | 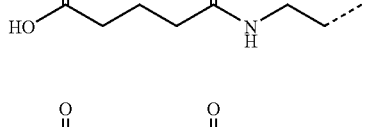 | 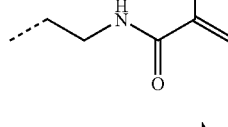 |
| 81 | 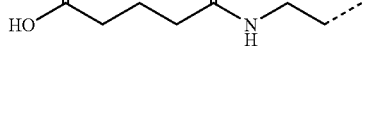 | 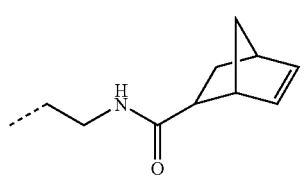 |

TABLE 3-continued

Exemplary Compounds $R^a\text{—O}\left(\diagdown\diagup\text{O}\right)_n R^b$

| # | $R^a$ | $R^b$ |
|---|---|---|
| 82 | 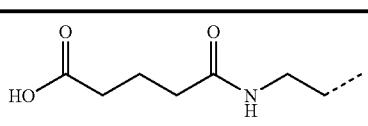 | 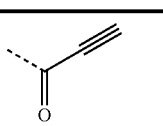 |
| 83 | 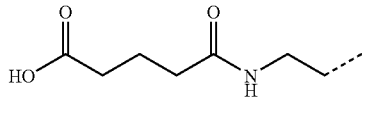 | 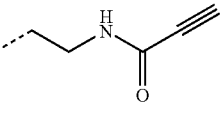 |

In certain embodiments, the present invention provides a compound as described herein, wherein $L^1$ is a $C_{1-6}$ alkylene wherein three methylene units of $L^1$ are substituted with —C(O)NH—, —O—, and —C(O)O—, and $R^1$ is hydrogen. Exemplary compounds include those set forth in Table 4, wherein n is as described in classes and subclasses herein. In certain embodiments, n is selected from 50±10. In other embodiments, n is selected from 80±10, 115±10, 180±10, or 225±10.

TABLE 4

Exemplary Compounds $R^a\text{—O}\left(\diagdown\diagup\text{O}\right)_n R^b$

| # | $R^a$ | $R^b$ |
|---|---|---|
| 84 | 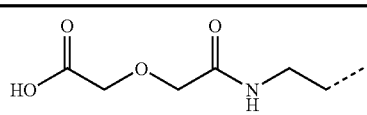 | 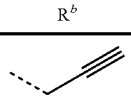 |
| 85 | 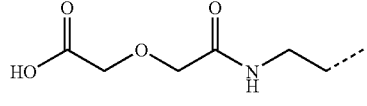 | 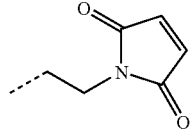 |
| 86 | 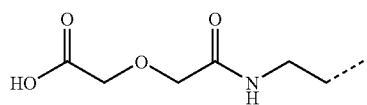 | 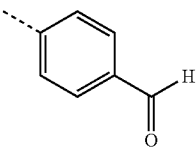 |
| 87 | 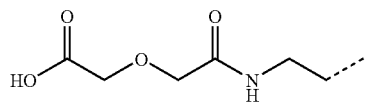 | 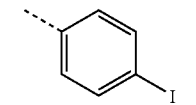 |
| 88 | 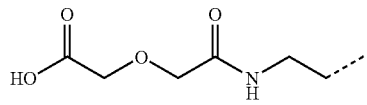 | 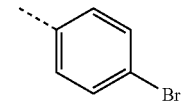 |

TABLE 4-continued

Exemplary Compounds $$R^a-O-(\phantom{x}-O-)_n-R^b$$

| # | $R^a$ | $R^b$ |
|---|---|---|
| 89 | HOOC-CH2-O-CH2-C(O)-NH- | 4-(NHBoc)-phenyl- |
| 90 | HOOC-CH2-O-CH2-C(O)-NH- | -CH2CH2-O-C(O)-CH2CH2-C≡CH |
| 91 | HOOC-CH2-O-CH2-C(O)-NH- | -CH2CH2-O-C(O)-(CH2)3-biotinyl |
| 92 | HOOC-CH2-O-CH2-C(O)-NH- | -CH2CH2-NH-C(O)-(CH2)3-biotinyl |
| 93 | HOOC-CH2-O-CH2-C(O)-NH- | -CH2CH2-NH-C(O)-CH2CH2-C≡CH |
| 94 | HOOC-CH2-O-CH2-C(O)-NH- | -CH2CH2-NH-C(O)-CH2-C≡CH |
| 95 | HOOC-CH2-O-CH2-C(O)-NH- | -CH2CH2-NH-C(O)-(CH2)3-C≡CH |
| 96 | HOOC-CH2-O-CH2-C(O)-NH- | -CH2CH2-O-C(O)-CH2CH2-C≡CH |

TABLE 4-continued
Exemplary Compounds
$R^a\text{—O}{\left(\phantom{\rule{0ex}{0ex}}\right)}_n\text{—O—}R^b$
| # | $R^a$ | $R^b$ |
|---|---|---|
| 97 | 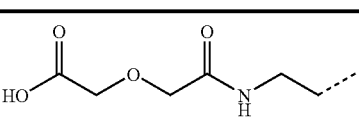 | 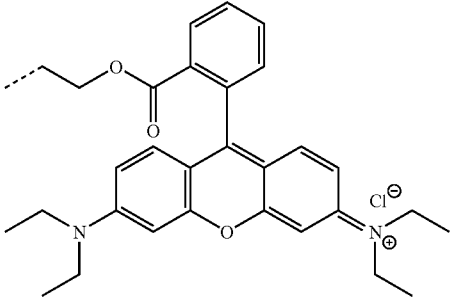 |
| 98 | 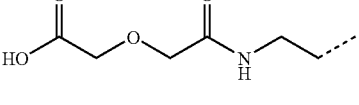 | 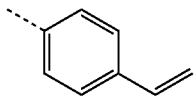 |
| 99 | 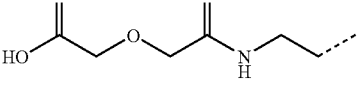 | 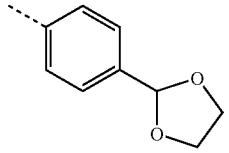 |
| 100 | 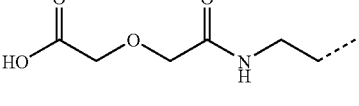 | 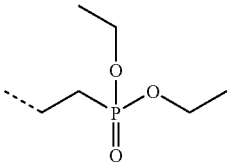 |
| 101 | 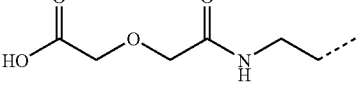 | 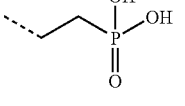 |
| 102 | 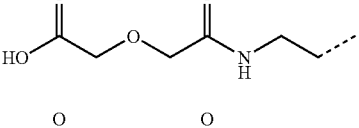 | 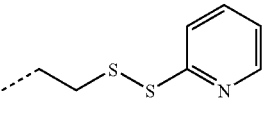 |
| 103 | 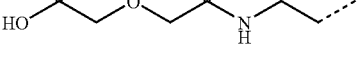 | 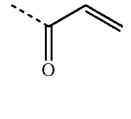 |
| 104 | 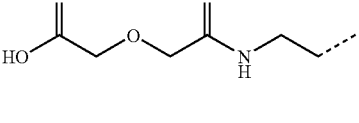 | 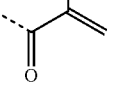 |
| 105 | 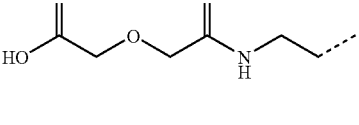 | 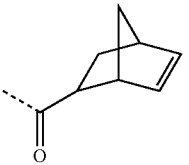 |

TABLE 4-continued

Exemplary Compounds $$R^a-O-(\phantom{x}O)_n-R^b$$

| # | $R^a$ | $R^b$ |
|---|-------|-------|
| 106 | HOOC-CH2-O-CH2-C(O)-NH-CH2CH2- | -CH2CH2-NH-C(O)-CH=CH2 |
| 107 | HOOC-CH2-O-CH2-C(O)-NH-CH2CH2- | -CH2CH2-NH-C(O)-C(CH3)=CH2 |
| 108 | HOOC-CH2-O-CH2-C(O)-NH-CH2CH2- | -CH2CH2-NH-C(O)-(norbornenyl) |
| 109 | HOOC-CH2-O-CH2-C(O)-NH-CH2CH2- | -C(O)-C≡CH |
| 110 | HOOC-CH2-O-CH2-C(O)-NH-CH2CH2- | -CH2CH2-NH-C(O)-C≡CH |

In certain embodiments, the present invention provides a compound as described herein, wherein $L^1$ is —O— and $R^1$ is hydrogen. Exemplary compounds include those set forth in Table 5, wherein n is as described in classes and subclasses herein. In certain embodiments, n is selected from 50±10. In other embodiments, n is selected from 80±10, 115±10, 180±10, or 225±10.

TABLE 5

Exemplary Compounds $$R^a-O-(\phantom{x}O)_n-R^b$$

| # | $R^a$ | $R^b$ |
|---|-------|-------|
| 111 | HO-CH2CH2- | -CH2CH2-S-C(Ph)3 |

TABLE 5-continued

Exemplary Compounds $$R^a-O-\left(\!\!\begin{array}{c}\\ \\ \end{array}\!\!\right)_n\!\!-O-R^b$$

| # | $R^a$ | $R^b$ |
|---|---|---|
| 112 | HO-CH₂CH₂- | -CH₂CH₂-N(maleimide) |
| 113 | HO-CH₂CH₂- | -C₆H₄-COOH (para) |
| 114 | HO-CH₂CH₂- | -C₆H₄-CHO (para) |
| 115 | HO-CH₂CH₂- | -C₆H₄-I (para) |
| 116 | HO-CH₂CH₂- | -C₆H₄-Br (para) |
| 117 | HO-CH₂CH₂- | -C₆H₄-CH=CH₂ (para) |
| 118 | HO-CH₂CH₂- | -C₆H₄-NH₂ (para) |
| 119 | HO-CH₂CH₂- | -CH₂CH₂-P(=O)(OEt)₂ |
| 120 | HO-CH₂CH₂- | -CH₂CH₂-P(=O)(OH)₂ |

TABLE 5-continued

Exemplary Compounds $$R^a\text{-O-}(\text{CH}_2\text{CH}_2\text{O})_n\text{-}R^b$$

| # | $R^a$ | $R^b$ |
|---|---|---|
| 121 | HO-CH₂CH₂- | -CH₂CH₂-P(O)Cl₂ |
| 122 | HO-CH₂CH₂- | biotin amide linker |
| 123 | HO-CH₂CH₂- | biotin ester linker |
| 124 | HO-CH₂CH₂- | acryloyl |
| 125 | HO-CH₂CH₂- | methacryloyl |
| 126 | HO-CH₂CH₂- | norbornene carbonyl |
| 127 | HO-CH₂CH₂- | acrylamidoethyl |
| 128 | HO-CH₂CH₂- | methacrylamidoethyl |

TABLE 5-continued
Exemplary Compounds
$$R^a-O\left(\!\!\begin{array}{c}\\\\\end{array}\!\!O\!\!\right)_{\!n}\!\!R^b$$
| # | $R^a$ | $R^b$ |
|---|---|---|
| 129 | 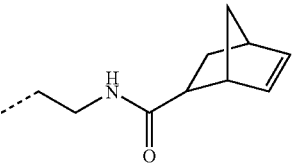 | 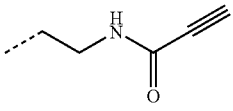 |
| 130 | 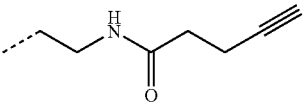 | 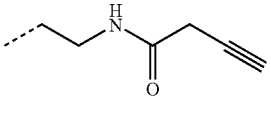 |
| 131 | 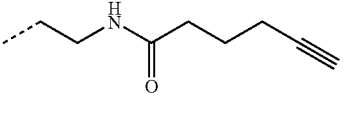 | 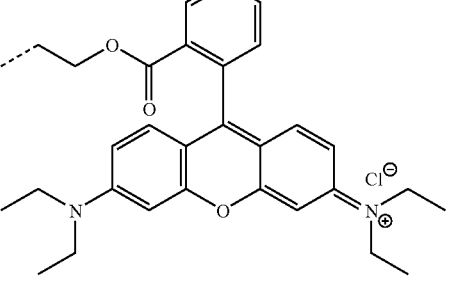 |
| 132 | 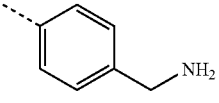 | 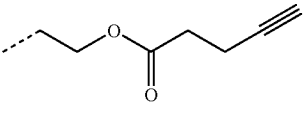 |
| 133 | HO⁓⁓ | ⁓⁓NH-C(O)-CH₂CH₂CH₂-C≡CH |
| 134 | HO⁓⁓ | (rhodamine B ester structure with Cl⁻) |
| 135 | HO⁓⁓ | ⁓⁓-C₆H₄-CH₂NH₂ |
| 136 | HO⁓⁓ | ⁓⁓-O-C(O)-CH₂CH₂-C≡CH |

TABLE 5-continued

Exemplary Compounds $R^a\text{-}O\text{-}(\text{-}CH_2CH_2\text{-}O\text{-})_n\text{-}R^b$

| # | $R^a$ | $R^b$ |
|---|---|---|
| 137 | HO-CH₂CH₂- | -C(O)-C≡CH |

In certain embodiments, the present invention provides a compound as described herein, wherein $L^1$ is —C(O)— and $R^1$ is hydrogen. Exemplary compounds include those set forth in Table 6, wherein n is as described in classes and subclasses herein. In certain embodiments, n is selected from 50±10. In other embodiments, n is selected from 80±10, 115±10, 180±10, or 225±10.

TABLE 6

Exemplary Compounds $R^a\text{-}O\text{-}(\text{-}CH_2CH_2\text{-}O\text{-})_n\text{-}R^b$

| # | $R^a$ | $R^b$ |
|---|---|---|
| 138 | H-C(O)-CH₂CH₂- | -CH₂CH₂-S-C(C₆H₅)₃ |
| 139 | H-C(O)-CH₂CH₂- | -CH₂CH₂-SH |
| 140 | H-C(O)-CH₂CH₂- | -CH₂-C≡CH |
| 141 | H-C(O)-CH₂CH₂- | -C₆H₄-C(O)OH |
| 142 | H-C(O)-CH₂CH₂- | -C₆H₄-C(O)H |

TABLE 6-continued

Exemplary Compounds $$R^a\text{—}O\text{—}(\text{CH}_2\text{CH}_2\text{O})_n\text{—}R^b$$

| # | $R^a$ | $R^b$ |
|---|---|---|
| 143 | OHC-CH2-CH2- | -CH2-CH2-N3 |
| 144 | OHC-CH2-CH2- | -C6H4-I (para) |
| 145 | OHC-CH2-CH2- | -C6H4-Br (para) |
| 146 | OHC-CH2-CH2- | -C6H4-CH=CH2 (para) |
| 147 | OHC-CH2-CH2- | -CH2-CH2-P(O)(OEt)2 |
| 148 | OHC-CH2-CH2- | -CH2-CH2-P(O)(OH)2 |
| 149 | OHC-CH2-CH2- | -CH2-CH2-P(O)Cl2 |
| 150 | OHC-CH2-CH2- | -CH2-CH2-NH-C(O)-(CH2)4-biotinyl |
| 151 | OHC-CH2-CH2- | -CH2-CH2-O-C(O)-(CH2)4-biotinyl |

TABLE 6-continued
Exemplary Compounds
$$R^a-O-\left(\!\!\begin{array}{c}\diagdown\diagup O\end{array}\!\!\right)_{\!n}\!\!-R^b$$
| # | $R^a$ | $R^b$ |
|---|---|---|
| 152 | 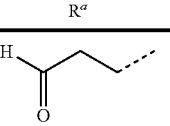 | 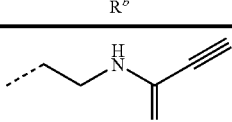 |
| 153 | 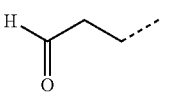 | 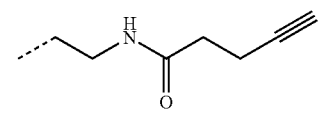 |
| 154 | 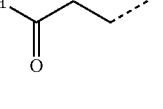 | 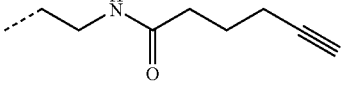 |
| 155 | 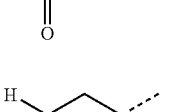 | 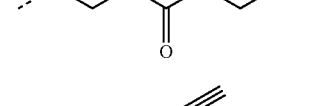 |
| 156 | 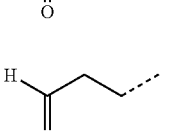 | 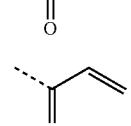 |
| 157 | 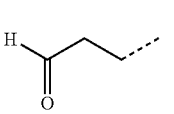 | 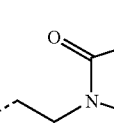 |
| 158 | 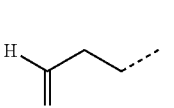 | 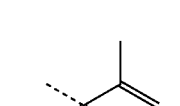 |
| 159 | 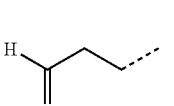 | 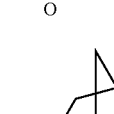 |
| 160 | 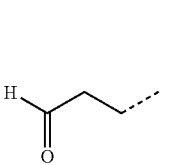 | 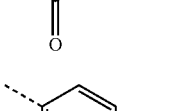 |
| 161 |  | 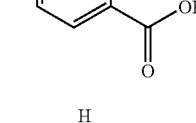 |
| 162 | 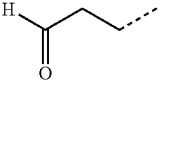 | 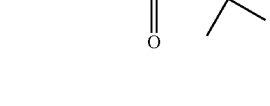 |

TABLE 6-continued

Exemplary Compounds $$R^a\text{-O-}(\text{-CH}_2\text{CH}_2\text{-O-})_n\text{-}R^b$$

| # | Rᵃ | Rᵇ |
|---|----|----|
| 163 | H-C(=O)-CH₂CH₂-··· | ···-CH₂-C(=O)-OH |
| 164 | H-C(=O)-CH₂CH₂-··· | Rhodamine B ester group (···-CH₂CH₂-O-C(=O)-phenyl-xanthene with diethylamino groups, Cl⁻) |
| 165 | H-C(=O)-CH₂CH₂-··· | ···-phenyl-C(=O)-O-N-succinimidyl |

In certain embodiments, the present invention provides a compound as described herein, wherein -L¹-R¹ moiety of formula I comprises a protected aldehyde. Exemplary compounds include those set forth in Table 7, wherein n is as described in classes and subclasses herein. In certain embodiments, n is selected from 50±10. In other embodiments, n is selected from 80±10, 115±10, 180±10, or 225±10.

TABLE 7

Exemplary Compounds $$R^a\text{-O-}(\text{-CH}_2\text{CH}_2\text{-O-})_n\text{-}R^b$$

| # | Rᵃ | Rᵇ |
|---|----|----|
| 166 | CH₃CH₂-O-CH(O-CH₂CH₃)-CH₂CH₂-··· | ···-phenyl-NH₂ |
| 167 | CH₃CH₂-O-CH(O-CH₂CH₃)-CH₂CH₂-··· | ···-phenyl-CH₂-NH₂ |

TABLE 7-continued

Exemplary Compounds $$R^a\text{-O}\!\left(\!\!\begin{array}{c}\diagup\!\!\!\diagdown\!\!\text{O}\end{array}\!\!\right)_{\!\!n}\!\!R^b$$

| # | $R^a$ | $R^b$ |
|---|---|---|
| 168 | 1,1-diethoxybutyl | 4-(mercaptomethyl)phenyl |
| 169 | 1,1-diethoxybutyl | 2-(propiolamido)ethyl |
| 170 | 1,1-diethoxybutyl | 2-(pent-4-ynamido)ethyl |
| 171 | 1,1-diethoxybutyl | 2-(hex-5-ynamido)ethyl |
| 172 | 1,1-diethoxybutyl | 4-(Boc-amino)phenyl |
| 173 | 1,1-diethoxybutyl | 4-carboxyphenyl |
| 174 | 1,1-diethoxybutyl | 4-(N-succinimidyloxycarbonyl)phenyl |
| 175 | 1,1-diethoxybutyl | 4-((4-nitrophenoxy)carbonyl)phenyl |

TABLE 7-continued
Exemplary Compounds
$$R^a\text{-}O\text{-}(\text{-}O\text{-})_n\text{-}R^b$$
| # | $R^a$ | $R^b$ |
|---|-------|-------|
| 176 | 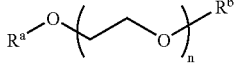 | 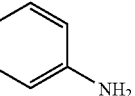 |
| 177 |  | 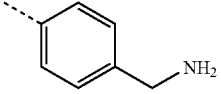 |
| 178 |  | 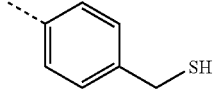 |
| 179 |  | 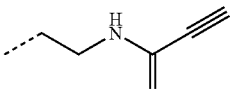 |

TABLE 7-continued
Exemplary Compounds
$$R^a\text{-}O\text{-}(\text{-}\text{-}\text{-}O\text{-})_n\text{-}R^b$$
| # | R$^a$ | R$^b$ |
|---|---|---|
| 180 | 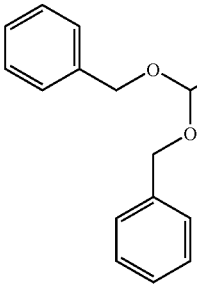 | 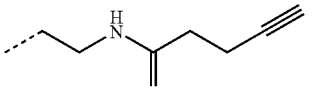 |
| 181 | 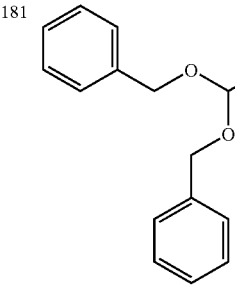 | 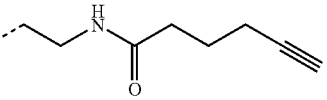 |
| 182 | 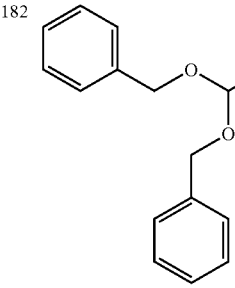 | 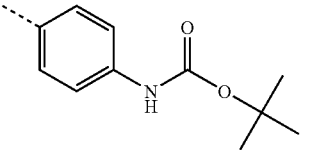 |
| 183 | 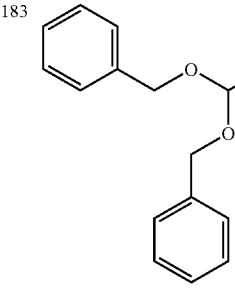 | 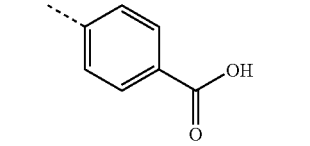 |

TABLE 7-continued

Exemplary Compounds

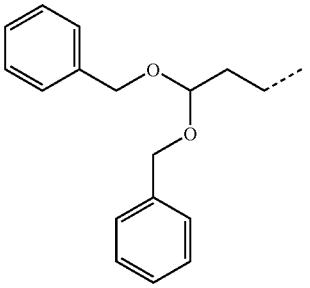

| # | $R^a$ | $R^b$ |
|---|-------|-------|
| 184 | 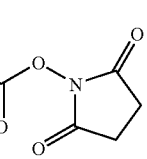 | 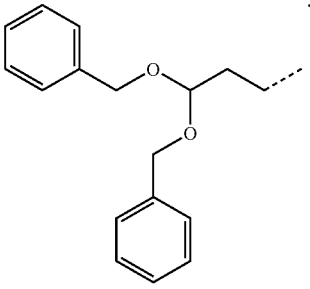 |
| 185 | 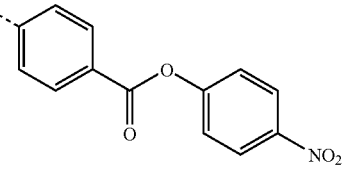 | 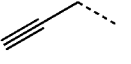 |

In certain embodiments, the present invention provides a compound as described herein, wherein the $R^1$ moiety of formula I comprises an acetylene moiety. Exemplary compounds include those set forth in Table 8, wherein n is as described in classes and subclasses herein. In certain embodiments, n is selected from 50±10. In other embodiments, n is selected from 80±10, 115±10, 180±10, or 225±10.

TABLE 8

Exemplary Compounds

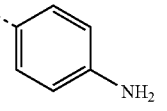

| # | $R^a$ | $R^b$ |
|---|-------|-------|
| 186 | 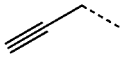 | 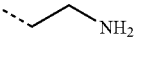 |
| 187 |  | NH$_2$ |
| 188 | 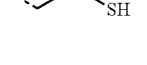 | SH |

TABLE 8-continued

Exemplary Compounds $$R^a\text{—O}\left(\text{—O}\right)_n\text{—}R^b$$

| # | $R^a$ | $R^b$ |
|---|---|---|
| 189 | propargyl | 4-carboxyphenyl |
| 190 | propargyl | biotin ester (ethyl biotinoate linker) |
| 191 | propargyl | biotin amide (ethylamide linker) |
| 192 | propargyl | -CH₂COOH |
| 193 | propargyl | rhodamine B ester (ethyl linker) |
| 194 | propargyl | -CH₂CH₂P(O)(OEt)₂ |
| 195 | propargyl | -CH₂CH₂P(O)(OH)₂ |

TABLE 8-continued

Exemplary Compounds $$R^a\text{-}O\text{-}(\text{-}O\text{-})_n\text{-}R^b$$

| # | $R^a$ | $R^b$ |
|---|-------|-------|
| 196 | propargyl | -CH₂CH₂-P(=O)Cl₂ |
| 197 | propargyl | -CH₂CH₂-(N-maleimidyl) |
| 198 | propargyl | -C₆H₄-CH₂NH₂ (para) |
| 199 | propargyl | -C₆H₄-CH₂SH (para) |

In certain embodiments, the present invention provides a compound as described herein, wherein the $R^1$ moiety of formula I comprises a protected acetylene moiety. Exemplary compounds include those set forth in Table 9, wherein n is as described in classes and subclasses herein. In certain embodiments, n is selected from 50±10. In other embodiments, n is selected from 80±10, 115±10, 180±10, or 225±10.

TABLE 9

Exemplary Compounds $$R^a\text{-}O\text{-}(\text{-}O\text{-})_n\text{-}R^b$$

| # | $R^a$ | $R^b$ |
|---|-------|-------|
| 200 | tert-butyldiphenylsilyl-C≡C-CH₂- | -C₆H₄-NH₂ (para) |
| 201 | tert-butyldiphenylsilyl-C≡C-CH₂- | -CH₂CH₂-NH₂ |

TABLE 9-continued

Exemplary Compounds $$R^a-O-(\!\!-\!\!-O\!\!-\!\!)_n\!\!-\!\!R^b$$

| # | $R^a$ | $R^b$ |
|---|-------|-------|
| 202 | *tert*-butyl(diphenyl)silyl-C≡C-CH₂- | -CH₂CH₂-SH |
| 203 | *tert*-butyl(diphenyl)silyl-C≡C-CH₂- | -C₆H₄-C(O)OH (para) |
| 204 | *tert*-butyl(diphenyl)silyl-C≡C-CH₂- | -CH₂CH₂-O-C(O)-(CH₂)₄-biotinyl |
| 205 | *tert*-butyl(diphenyl)silyl-C≡C-CH₂- | -CH₂CH₂-NH-C(O)-(CH₂)₄-biotinyl |
| 206 | *tert*-butyl(diphenyl)silyl-C≡C-CH₂- | -CH₂-C(O)OH |

TABLE 9-continued

Exemplary Compounds $$R^a-O-(\phantom{x}O)_n-R^b$$

| # | $R^a$ | $R^b$ |
|---|---|---|
| 207 | tert-butyl(diphenyl)silyl-C≡C-CH₂-CH₂-CH₂-O- | rhodamine B ester (2-carboxyphenyl attached to 9-position of 3,6-bis(diethylamino)xanthylium chloride) |
| 208 | tert-butyl(diphenyl)silyl-C≡C-CH₂- | -CH₂-CH₂-P(=O)(OEt)₂ |
| 209 | tert-butyl(diphenyl)silyl-C≡C-CH₂- | -CH₂-CH₂-P(=O)(OH)₂ |
| 210 | tert-butyl(diphenyl)silyl-C≡C-CH₂- | -CH₂-CH₂-P(=O)Cl₂ |
| 211 | tert-butyl(diphenyl)silyl-C≡C-CH₂- | -CH₂-CH₂-N(maleimide) |

TABLE 9-continued

Exemplary Compounds $$R^a-O-(CH_2CH_2O)_n-R^b$$

| # | $R^a$ | $R^b$ |
|---|-------|-------|
| 212 | tert-butyl(diphenyl)silyl-C≡C-CH₂- | 4-(aminomethyl)phenyl- |
| 213 | tert-butyl(diphenyl)silyl-C≡C-CH₂- | 4-(mercaptomethyl)phenyl- |
| 214 | tert-butyl(dimethyl)silyl-C≡C-CH₂- | 4-aminophenyl- |
| 215 | tert-butyl(dimethyl)silyl-C≡C-CH₂- | -CH₂CH₂NH₂ |
| 216 | tert-butyl(dimethyl)silyl-C≡C-CH₂- | -CH₂CH₂SH |
| 217 | tert-butyl(dimethyl)silyl-C≡C-CH₂- | 4-carboxyphenyl- |
| 218 | tert-butyl(dimethyl)silyl-C≡C-CH₂- | biotin ester linker |

TABLE 9-continued

Exemplary Compounds $$R^a\text{—O}\left(\text{—}\!\!\!\!\!\diagup\!\!\!\!\!\text{O}\right)_n\!\!\!R^b$$

| # | $R^a$ | $R^b$ |
|---|---|---|
| 219 | tert-butyldimethylsilyl-alkyne | biotin-amide linker |
| 220 | tert-butyldimethylsilyl-alkyne | -CH2CH2C(O)OH |
| 221 | tert-butyldimethylsilyl-alkyne | rhodamine B ester |
| 222 | tert-butyldimethylsilyl-alkyne | -CH2CH2P(O)(OEt)2 |
| 223 | tert-butyldimethylsilyl-alkyne | -CH2CH2P(O)(OH)2 |
| 224 | tert-butyldimethylsilyl-alkyne | -CH2CH2P(O)Cl2 |
| 225 | tert-butyldimethylsilyl-alkyne | -CH2CH2-maleimide |

TABLE 9-continued

Exemplary Compounds $R^a\text{—O—}(\text{—}\text{—O—})_n\text{—}R^b$

| # | $R^a$ | $R^b$ |
|---|---|---|
| 226 | 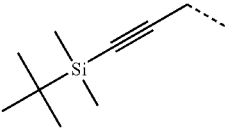 | 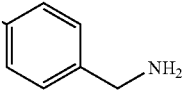 |
| 227 | 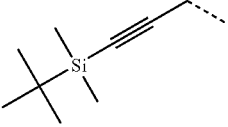 | 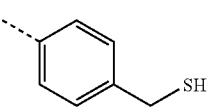 |

In certain embodiments, the present invention provides a compound as described herein, wherein the $R^1$ moiety of formula I comprises —$NH_2$. Exemplary compounds include those set forth in Table 10, wherein n is as described in classes and subclasses herein. In certain embodiments, n is selected from 50±10. In other embodiments, n is selected from 80±10, 115±10, or 225±10.

TABLE 10

Exemplary Compounds $R^a\text{—O—}(\text{—}\text{—O—})_n\text{—}R^b$

| # | $R^a$ | $R^b$ |
|---|---|---|
| 228 | 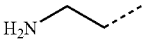 | 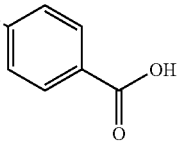 |
| 229 | 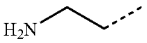 | 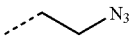 |
| 230 | 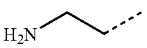 | 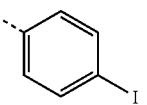 |
| 231 | 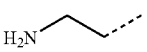 | 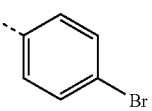 |
| 232 | 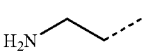 | 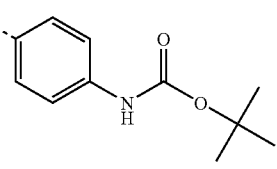 |

TABLE 10-continued

Exemplary Compounds $$R^a-O-(\phantom{x}O\phantom{x})_n-R^b$$

| # | R$^a$ | R$^b$ |
|---|---|---|
| 233 | H$_2$N-CH$_2$CH$_2$- | -CH$_2$CH$_2$-O-C(=O)-CH$_2$-C≡CH |
| 234 | H$_2$N-CH$_2$CH$_2$- | -CH$_2$CH$_2$-NH-C(=O)-(CH$_2$)$_4$-biotinyl |
| 235 | H$_2$N-CH$_2$CH$_2$- | -CH$_2$CH$_2$-O-C(=O)-(CH$_2$)$_4$-biotinyl |
| 236 | H$_2$N-CH$_2$CH$_2$- | -CH$_2$CH$_2$-S-S-(2-pyridyl) |
| 237 | H$_2$N-CH$_2$CH$_2$- | -C(=O)-CH=CH$_2$ |
| 238 | H$_2$N-CH$_2$CH$_2$- | -C(=O)-C(CH$_3$)=CH$_2$ |
| 239 | H$_2$N-CH$_2$CH$_2$- | -C(=O)-norbornenyl |
| 240 | H$_2$N-CH$_2$CH$_2$- | -CH$_2$CH$_2$-NH-C(=O)-CH=CH$_2$ |
| 241 | H$_2$N-CH$_2$CH$_2$- | -CH$_2$CH$_2$-NH-C(=O)-C(CH$_3$)=CH$_2$ |

TABLE 10-continued

Exemplary Compounds $$R^a\text{—O}\left(\text{—}\!\!\!\begin{array}{c}\\\end{array}\!\!\!\text{—O}\right)_n\!\!R^b$$

| # | $R^a$ | $R^b$ |
|---|---|---|
| 242 | H₂N–CH₂CH₂– | –CH₂CH₂–NH–C(=O)–norbornenyl |
| 243 | H₂N–CH₂CH₂– | –C₆H₄–CH₂NH₂ (para) |
| 244 | H₂N–CH₂CH₂– | –C₆H₄–CH=CH₂ (para) |
| 245 | H₂N–CH₂CH₂– | –C₆H₄–CH(OCH₂CH₂O) (para, 1,3-dioxolane) |
| 246 | H₂N–CH₂CH₂– | –CH₂CH₂–P(=O)(OEt)₂ |
| 248 | H₂N–CH₂CH₂– | –CH₂CH₂–P(=O)(OH)₂ |
| 249 | H₂N–CH₂CH₂– | –C₆H₄–C(=O)OCH₃ (para) |
| 250 | H₂N–CH₂CH₂– | –CH₂CH₂–NH–C(=O)–C≡CH |
| 251 | H₂N–CH₂CH₂– | –CH₂CH₂–NH–C(=O)–CH₂–C≡CH |
| 252 | H₂N–CH₂CH₂– | –CH₂CH₂–NH–C(=O)–CH₂CH₂–C≡CH |

TABLE 10-continued

Exemplary Compounds $R^a\text{—O}\left(\diagup\diagup\text{O}\right)_n R^b$

| # | $R^a$ | $R^b$ |
|---|---|---|
| 253 | H₂N–CH₂CH₂– | –C₆H₄–CH₂–SH (para) |
| 254 | H₂N–CH₂CH₂– | –C(=O)–C≡CH |
| 255 | H₂N–CH₂CH₂– | –CH₂CH₂–O–C(=O)–CH₂CH₂–C≡CH |

In certain embodiments, the present invention provides a compound as described herein, wherein the $R^1$ moiety of formula I comprises a protected amino group. Exemplary compounds include those set forth in Table 11, wherein n is as described in classes and subclasses herein. In certain embodiments, n is selected from 50±10. In other embodiments, n is selected from 80±10, 115±10, 180±10, or 225±10.

TABLE 11

Exemplary Compounds $R^a\text{—O}\left(\diagup\diagup\text{O}\right)_n R^b$

| # | $R^a$ | $R^b$ |
|---|---|---|
| 256 | Boc-NH-CH₂CH₂– | –C₆H₄–C(=O)OH (para) |
| 257 | Boc-NH-CH₂CH₂– | –CH₂CH₂–N₃ |
| 258 | Boc-NH-CH₂CH₂– | –C₆H₄–I (para) |
| 259 | Boc-NH-CH₂CH₂– | –C₆H₄–Br (para) |

TABLE 11-continued
Exemplary Compounds
$$R^a\text{-O}\left(\diagdown\diagup\text{O}\right)_n\text{-}R^b$$
| # | $R^a$ | $R^b$ |
|---|---|---|
| 260 | 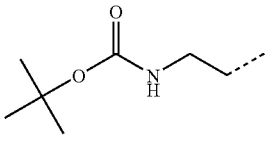 | 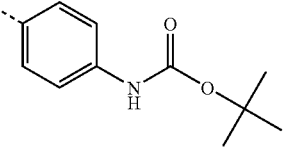 |
| 261 | 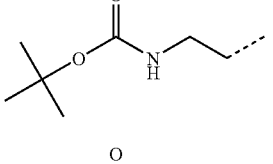 | 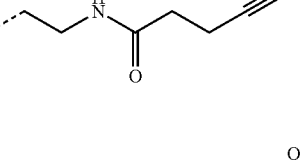 |
| 262 | 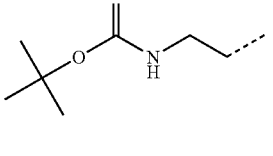 | 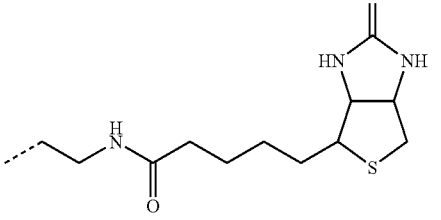 |
| 263 | 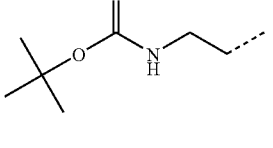 | 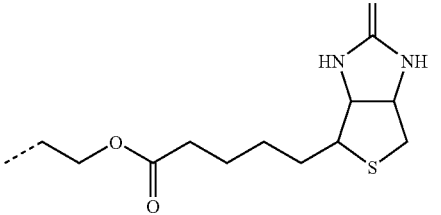 |
| 264 | 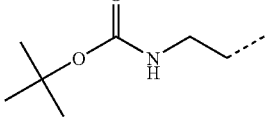 | 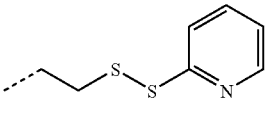 |
| 265 | 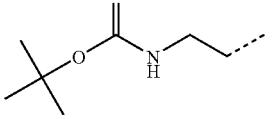 | 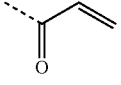 |
| 266 | 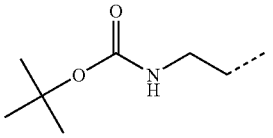 | 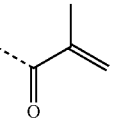 |
| 267 | 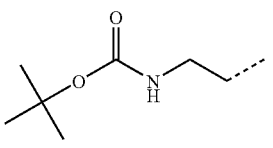 | 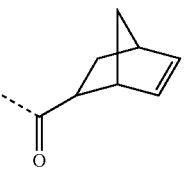 |

TABLE 11-continued

Exemplary Compounds $$R^a-O-(\!\!\!\sim\!\!\!O\!\!\!\sim\!\!\!)_n-R^b$$

| # | R$^a$ | R$^b$ |
|---|---|---|
| 268 | tert-butyl carbamate-ethyl- | -ethyl-NH-C(O)-CH=CH$_2$ |
| 269 | tert-butyl carbamate-ethyl- | -ethyl-NH-C(O)-C(CH$_3$)=CH$_2$ |
| 270 | tert-butyl carbamate-ethyl- | -ethyl-NH-C(O)-norbornenyl |
| 271 | tert-butyl carbamate-ethyl- | -4-(aminomethyl)phenyl- |
| 272 | tert-butyl carbamate-ethyl- | -4-vinylphenyl- |
| 273 | tert-butyl carbamate-ethyl- | -4-(1,3-dioxolan-2-yl)phenyl- |
| 274 | tert-butyl carbamate-ethyl- | -ethyl-P(O)(OEt)$_2$ |
| 275 | tert-butyl carbamate-ethyl- | -ethyl-NH$_2$ |
| 276 | tert-butyl carbamate-ethyl- | -4-(methoxycarbonyl)phenyl- |

TABLE 11-continued
Exemplary Compounds
$$R^a-O-(\phantom{x}O\phantom{x})_n-R^b$$
| # | $R^a$ | $R^b$ |
|---|---|---|
| 277 | 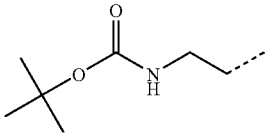 | 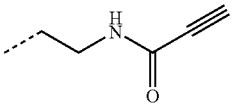 |
| 278 | 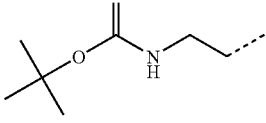 | 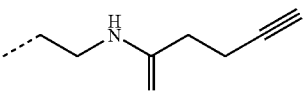 |
| 279 | 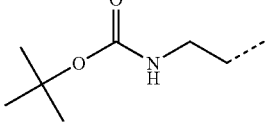 | 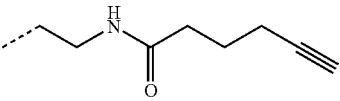 |
| 280 | 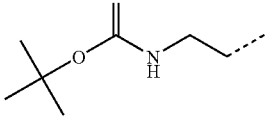 | 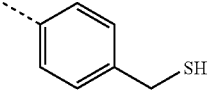 |
| 281 | 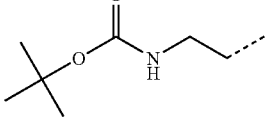 | 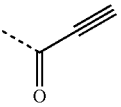 |
| 282 | 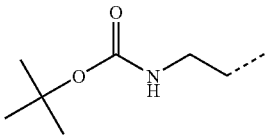 | 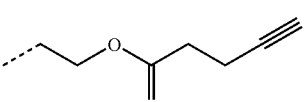 |
| 283 | 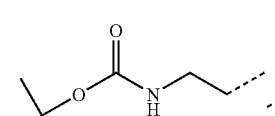 | 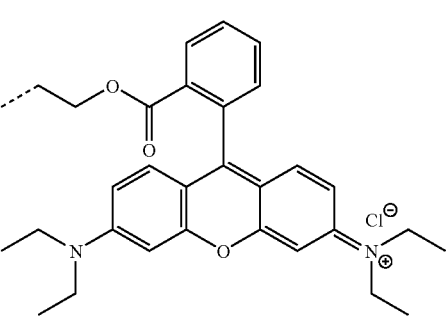 |

TABLE 11-continued

Exemplary Compounds $$R^a-O-(\phantom{x}O\phantom{x})_n-R^b$$

| # | $R^a$ | $R^b$ |
|---|---|---|
| 284 | tert-butyl carbamate ethyl | 4-formylphenyl |
| 285 | tert-butyl carbamate ethyl | ethylphosphonic dichloride |
| 286 | tert-butyl carbamate ethyl | N-ethylmaleimide |
| 287 | tert-butyl carbamate ethyl | 4-(N-succinimidyloxycarbonyl)phenyl |
| 288 | tert-butyl carbamate ethyl | 4-(4-nitrophenoxycarbonyl)phenyl |
| 289 | tert-butyl carbamate ethyl | 2-methyl-3-(4-phenoxy)-N-succinimidyl propanoate |

TABLE 11-continued

Exemplary Compounds

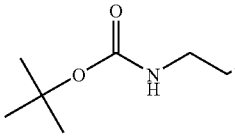

| # | $R^a$ | $R^b$ |
|---|---|---|
| 290 | 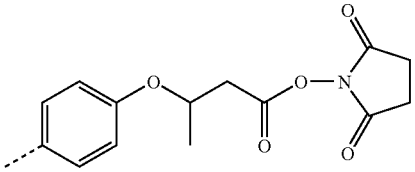 | 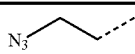 |

In certain embodiments, the present invention provides a compound as described herein, wherein the $R^1$ moiety of formula I comprises an azide. Exemplary compounds include those set forth in Table 12, wherein n is as described in classes and subclasses herein. In certain embodiments, n is selected from 50±10. In other embodiments, n is selected from 80±10, 115±10, 180±10, or 225±10.

TABLE 12

Exemplary Compounds

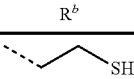

| # | $R^a$ | $R^b$ |
|---|---|---|
| 291 | 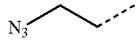 | 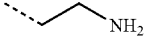 |
| 292 | 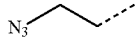 | 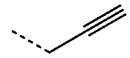 |
| 293 | 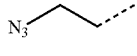 | 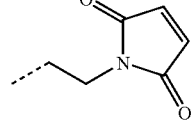 |
| 294 | 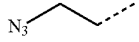 | 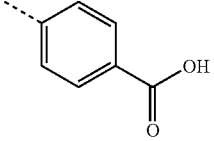 |
| 295 | 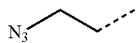 | 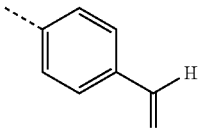 |
| 296 |  |  |

TABLE 12-continued

Exemplary Compounds $$R^a-O\left(\!\!\!\begin{array}{c}\\ \\ \end{array}\!\!\!\!O\!\!\!\right)_{\!n}\!\!R^b$$

| # | $R^a$ | $R^b$ |
|---|---|---|
| 297 | N₃–CH₂CH₂– | 4-iodophenyl |
| 298 | N₃–CH₂CH₂– | 4-bromophenyl |
| 299 | N₃–CH₂CH₂– | 4-(NHBoc)phenyl |
| 300 | N₃–CH₂CH₂– | –CH₂CH₂–O–C(O)–CH₂CH₂–C≡CH |
| 301 | N₃–CH₂CH₂– | –CH₂CH₂–NH–C(O)–(CH₂)₄–biotinyl |
| 302 | N₃–CH₂CH₂– | –CH₂CH₂–O–C(O)–(CH₂)₄–biotinyl |
| 303 | N₃–CH₂CH₂– | –CH₂CH₂–S–S–(2-pyridyl) |

TABLE 12-continued

Exemplary Compounds $$R^a\text{-}O\text{-}(\text{-}CH_2CH_2\text{-}O\text{-})_n\text{-}R^b$$

| # | $R^a$ | $R^b$ |
|---|-------|-------|
| 304 | N₃–CH₂CH₂CH₂– | –C(=O)–CH=CH₂ |
| 305 | N₃–CH₂CH₂CH₂– | –C(=O)–C(CH₃)=CH₂ |
| 306 | N₃–CH₂CH₂CH₂– | –C(=O)–norbornenyl |
| 307 | N₃–CH₂CH₂CH₂– | –C(=O)–C≡CH |
| 308 | N₃–CH₂CH₂CH₂– | –CH₂CH₂–NH–C(=O)–CH=CH₂ |
| 309 | N₃–CH₂CH₂CH₂– | –CH₂CH₂–NH–C(=O)–C(CH₃)=CH₂ |
| 310 | N₃–CH₂CH₂CH₂– | –CH₂CH₂–NH–C(=O)–norbornenyl |
| 311 | N₃–CH₂CH₂CH₂– | –C₆H₄–CH₂–NH₂ |

TABLE 12-continued

Exemplary Compounds $$R^a\text{-}O\text{-}(\text{CH}_2\text{CH}_2\text{O})_n\text{-}R^b$$

| # | $R^a$ | $R^b$ |
|---|---|---|
| 312 | N₃–CH₂CH₂CH₂– | –C₆H₄–CH=CH₂ (4-vinylphenyl) |
| 313 | N₃–CH₂CH₂CH₂– | 4-(1,3-dioxolan-2-yl)phenyl |
| 314 | N₃–CH₂CH₂CH₂– | –CH₂CH₂–P(=O)(OEt)₂ |
| 315 | N₃–CH₂CH₂CH₂– | –CH₂CH₂–P(=O)(OH)₂ |
| 316 | N₃–CH₂CH₂CH₂– | –CH₂CH₂–P(=O)Cl₂ |
| 317 | N₃–CH₂CH₂CH₂– | –CH₂CH₂–NH–C(=O)–C≡CH |
| 318 | N₃–CH₂CH₂CH₂– | –CH₂CH₂–NH–C(=O)–CH₂CH₂–C≡CH |
| 319 | N₃–CH₂CH₂CH₂– | –CH₂CH₂–NH–C(=O)–CH₂CH₂CH₂–C≡CH |
| 320 | N₃–CH₂CH₂CH₂– | –CH₂CH₂–O–C(=O)–CH₂CH₂–C≡CH |

TABLE 12-continued

Exemplary Compounds $$R^a\text{-}O\text{-}(\text{-}O\text{-})_n\text{-}R^b$$

| # | $R^a$ | $R^b$ |
|---|---|---|
| 321 | N₃–CH₂CH₂– | rhodamine B ester derivative (with Cl⁻ counterion) |

In certain embodiments, the present invention provides a compound as described herein, wherein the $R^1$ moiety of formula I comprises an epoxide. Exemplary compounds include those set forth in Table 13, wherein n is as described in classes and subclasses herein. In certain embodiments, n is selected from 50±10. In other embodiments, n is selected from 80±10, 115±10, 180±10, or 225±10.

TABLE 13

Exemplary Compounds $$R^a\text{-}O\text{-}(\text{-}O\text{-})_n\text{-}R^b$$

| # | $R^a$ | $R^b$ |
|---|---|---|
| 322 | glycidyl | –CH₂CH₂–S–C(C₆H₅)₃ |
| 323 | glycidyl | 4-vinylphenyl |
| 324 | glycidyl | –CH₂CH₂–P(=O)(Cl)₂ |

TABLE 13-continued

Exemplary Compounds $$R^a\text{-}O\text{-}(\text{CH}_2\text{CH}_2\text{O})_n\text{-}R^b$$

| # | R$^a$ | R$^b$ |
|---|---|---|
| 325 | (glycidyl) | -CH$_2$CH$_2$-P(=O)(OEt)$_2$ |
| 326 | (glycidyl) | -CH$_2$CH$_2$-P(=O)(OH)$_2$ |
| 327 | (glycidyl) | 4-formylphenyl |
| 328 | (glycidyl) | -CH$_2$CH$_2$-NH-C(=O)-(CH$_2$)$_4$-biotinyl |
| 329 | (glycidyl) | -CH$_2$CH$_2$-O-C(=O)-(CH$_2$)$_4$-biotinyl |
| 330 | (glycidyl) | 4-aminophenyl |
| 331 | (glycidyl) | -CH$_2$CH$_2$-NH-C(=O)-C≡CH |
| 332 | (glycidyl) | -CH$_2$CH$_2$-NH-C(=O)-CH$_2$-C≡CH |
| 333 | (glycidyl) | -CH$_2$CH$_2$-NH-C(=O)-CH$_2$CH$_2$-C≡CH |

TABLE 13-continued

Exemplary Compounds $$R^a\text{-}O{\left(\text{-}O\text{-}\right)}_n R^b$$

| # | $R^a$ | $R^b$ |
|---|---|---|
| 334 | glycidyl | propyl-O-C(=O)-CH₂CH₂-C≡CH |
| 335 | glycidyl | acryloyl |
| 336 | glycidyl | methacryloyl |
| 337 | glycidyl | norbornene-carbonyl |
| 338 | glycidyl | propyl-NH-C(=O)-CH=CH₂ |
| 339 | glycidyl | propyl-NH-C(=O)-C(CH₃)=CH₂ |
| 340 | glycidyl | propyl-NH-C(=O)-norbornenyl |
| 341 | glycidyl | propargyl carbonyl (C(=O)-C≡CH) |
| 342 | glycidyl | rhodamine B ester (propyl ester linker) Cl⁻ |

TABLE 13-continued

Exemplary Compounds

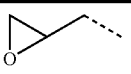

| # | $R^a$ | $R^b$ |
|---|---|---|
| 343 | 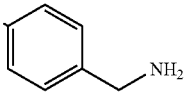 | 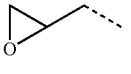 |
| 344 | 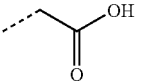 | 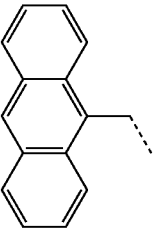 |

In certain embodiments, the present invention provides a compound as described herein, wherein the $R^1$ moiety of formula I comprises a detectable moiety. Exemplary compounds include those set forth in Table 14, wherein n is as described in classes and subclasses herein. In certain embodiments, n is selected from 50±10. In other embodiments, n is selected from 80±10, 115±10, 180±10, or 225±10.

TABLE 14

Exemplary Compounds

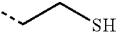

| # | $R^a$ | $R^b$ |
|---|---|---|
| 345 | 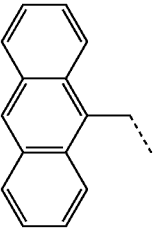 | 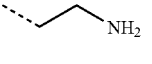 |
| 346 | 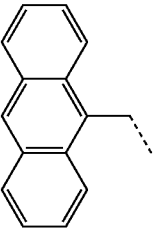 | 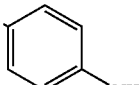 |
| 347 | | |

TABLE 14-continued
Exemplary Compounds
$$R^a-O-(\phantom{x}O\phantom{x})_n-R^b$$
| # | $R^a$ | $R^b$ |
|---|---|---|
| 348 | 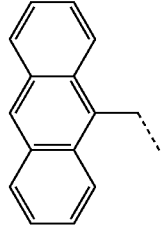 | 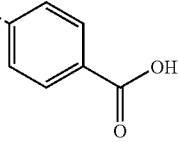 |
| 349 | 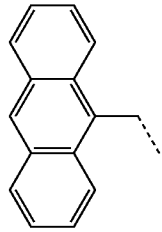 | 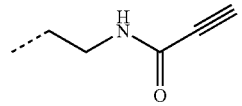 |
| 350 | 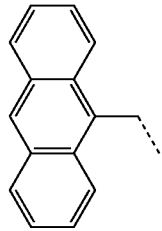 | 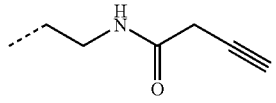 |
| 351 | 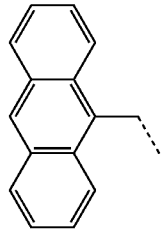 | 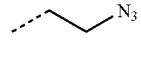 |
| 352 | 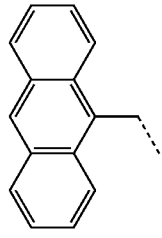 | 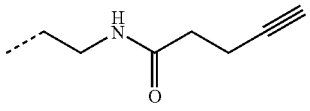 |
| 353 | 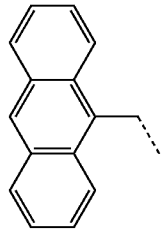 | 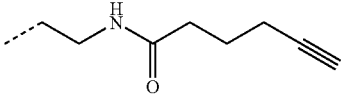 |

TABLE 14-continued

Exemplary Compounds $$R^a\text{—}O\text{—}(\text{—}\text{—}O\text{—})_n\text{—}R^b$$

| # | $R^a$ | $R^b$ |
|---|-------|-------|
| 354 | 9-anthracenylmethyl | -CH2CH2-NH-C(O)-CH=CH2 |
| 355 | 9-anthracenylmethyl | -CH2CH2-NH-C(O)-C(CH3)=CH2 |
| 356 | 9-anthracenylmethyl | -CH2CH2-NH-C(O)-norbornenyl |
| 357 | 9-anthracenylmethyl | -CH2CH2-S-S-(2-pyridyl) |
| 358 | 9-anthracenylmethyl | -C6H4-C(O)H |
| 359 | 9-anthracenylmethyl | -C(O)-CH=CH2 |

TABLE 14-continued

Exemplary Compounds $$R^a-O-(-CH_2CH_2-O-)_n-R^b$$

| # | $R^a$ | $R^b$ |
|---|---|---|
| 360 | 9-anthracenylmethyl | methacryloyl |
| 361 | 9-anthracenylmethyl | norbornene-2-carbonyl |
| 362 | 1-pyrenylmethyl | -CH₂CH₂SH |
| 363 | 1-pyrenylmethyl | -CH₂CH₂NH₂ |
| 364 | 1-pyrenylmethyl | 4-aminophenyl |
| 365 | 1-pyrenylmethyl | 4-carboxyphenyl |

TABLE 14-continued

Exemplary Compounds $$R^a\text{-O-}(\text{-}CH_2CH_2\text{-O-})_n\text{-}R^b$$

| # | $R^a$ | $R^b$ |
|---|---|---|
| 366 | pyrenyl-CH2- | -CH2CH2-NH-C(O)-C≡CH |
| 367 | pyrenyl-CH2- | -CH2CH2-NH-C(O)-CH2-C≡CH |
| 368 | pyrenyl-CH2- | -CH2CH2-N3 |
| 369 | pyrenyl-CH2- | -CH2CH2-NH-C(O)-CH2CH2-C≡CH |
| 370 | pyrenyl-CH2- | -CH2CH2-NH-C(O)-CH2CH2CH2-C≡CH |
| 371 | pyrenyl-CH2- | -CH2CH2-NH-C(O)-CH=CH2 |

TABLE 14-continued
Exemplary Compounds
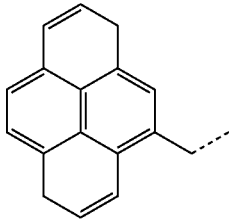
| # | R$^a$ | R$^b$ |
|---|---|---|
| 372 | 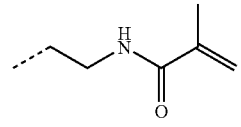 | 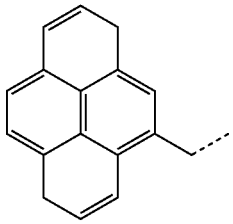 |
| 373 | 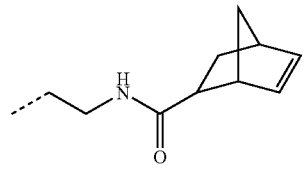 | 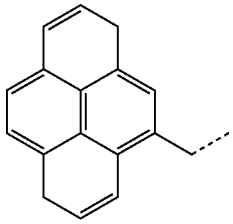 |
| 374 | 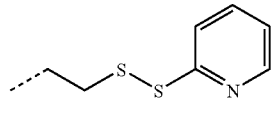 | 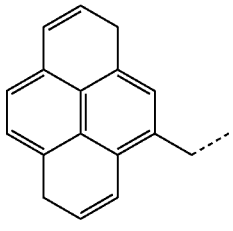 |
| 375 | 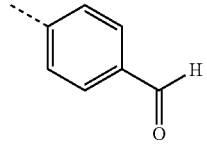 | 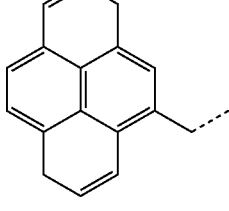 |
| 376 | 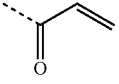 | 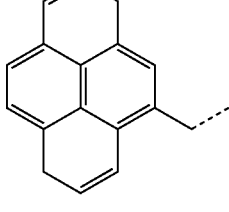 |
| 377 | 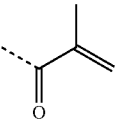 | |

TABLE 14-continued

Exemplary Compounds $$R^a\text{-}O\text{-}(\text{-}\diagup\text{-}O\text{-})_n\text{-}R^b$$

| # | R$^a$ | R$^b$ |
|---|---|---|
| 378 | (pyrene-CH₂-) | (norbornenyl-C(O)-) |

In certain embodiments, the present invention provides a compound as described herein, wherein the L$^1$ moiety of formula I is a C$_{1-8}$ membered alkylene wherein three methylene units of L$^1$ are replaced by —C(O)NH—, —NHC(O)—, and —NH—, and R$^1$ is hydrogen. Exemplary compounds include those set forth in Table 15, wherein n is as described in classes and subclasses herein. In certain embodiments, n is selected from 50±10. In other embodiments, n is selected from 80±10, 115±10, 180±10, or 225±10.

TABLE 15

Exemplary Compounds $$R^a\text{-}O\text{-}(\text{-}\diagup\text{-}O\text{-})_n\text{-}R^b$$

| # | R$^a$ | R$^b$ |
|---|---|---|
| 379 | H₂N-NH-C(O)-CH₂CH₂-C(O)-NH-CH₂CH₂- | -CH₂-C≡CH |
| 380 | H₂N-NH-C(O)-CH₂CH₂-C(O)-NH-CH₂CH₂- | -CH₂CH₂-N₃ |
| 381 | H₂N-NH-C(O)-CH₂CH₂-C(O)-NH-CH₂CH₂- | -C₆H₄-I |
| 382 | H₂N-NH-C(O)-CH₂CH₂-C(O)-NH-CH₂CH₂- | -C₆H₄-Br |

TABLE 15-continued

Exemplary Compounds $$R^a\text{—O}\left(\phantom{\rule{1em}{0ex}}\text{O}\right)_n R^b$$

| # | $R^a$ | $R^b$ |
|---|---|---|
| 383 | H₂N-NH-C(O)-CH₂CH₂-C(O)-NH-CH₂CH₂- | -C₆H₄-NH-C(O)-O-C(CH₃)₃ |
| 384 | H₂N-NH-C(O)-CH₂CH₂-C(O)-NH-CH₂CH₂- | -CH₂CH₂-O-C(O)-CH₂-C≡CH |
| 385 | H₂N-NH-C(O)-CH₂CH₂-C(O)-NH-CH₂CH₂- | -CH₂CH₂-NH-C(O)-(CH₂)₄-biotinyl |
| 386 | H₂N-NH-C(O)-CH₂CH₂-C(O)-NH-CH₂CH₂- | -CH₂CH₂-O-C(O)-(CH₂)₄-biotinyl |
| 387 | H₂N-NH-C(O)-CH₂CH₂-C(O)-NH-CH₂CH₂- | -CH₂CH₂-NH-C(O)-C≡CH |
| 388 | H₂N-NH-C(O)-CH₂CH₂-C(O)-NH-CH₂CH₂- | -CH₂CH₂-NH-C(O)-CH₂-C≡CH |
| 389 | H₂N-NH-C(O)-CH₂CH₂-C(O)-NH-CH₂CH₂- | -CH₂CH₂-NH-C(O)-CH₂CH₂-C≡CH |

TABLE 15-continued

Exemplary Compounds $$R^a\text{—O}\left(\text{~~~~O}\right)_n\text{—}R^b$$

| # | $R^a$ | $R^b$ |
|---|---|---|
| 390 | H₂N-NH-C(O)-CH₂CH₂-C(O)-NH-CH₂CH₂- | rhodamine B ester linkage (propyl ester of 2-(3,6-bis(diethylamino)xanthylium-9-yl)benzoate, Cl⁻) |
| 391 | H₂N-NH-C(O)-CH₂CH₂-C(O)-NH-CH₂CH₂- | 4-vinylphenyl |
| 392 | H₂N-NH-C(O)-CH₂CH₂-C(O)-NH-CH₂CH₂- | 4-(1,3-dioxolan-2-yl)phenyl |
| 393 | H₂N-NH-C(O)-CH₂CH₂-C(O)-NH-CH₂CH₂- | -CH₂CH₂-P(O)(OEt)₂ |
| 394 | H₂N-NH-C(O)-CH₂CH₂-C(O)-NH-CH₂CH₂- | -CH₂CH₂-S-S-(2-pyridyl) |
| 395 | H₂N-NH-C(O)-CH₂CH₂-C(O)-NH-CH₂CH₂- | -C(O)-CH=CH₂ |
| 396 | H₂N-NH-C(O)-CH₂CH₂-C(O)-NH-CH₂CH₂- | -C(O)-C(CH₃)=CH₂ |
| 397 | H₂N-NH-C(O)-CH₂CH₂-C(O)-NH-CH₂CH₂- | -CH₂CH₂-NH-C(O)-CH=CH₂ |

TABLE 15-continued

Exemplary Compounds $$R^a\text{—}O\left(\text{—}\diagdown\diagdown\text{—}O\right)_n R^b$$

| # | R$^a$ | R$^b$ |
|---|---|---|
| 398 | H₂N-NH-C(O)-CH₂-CH₂-C(O)-NH-CH₂- | -CH₂-NH-C(O)-C(CH₃)=CH₂ |
| 399 | H₂N-NH-C(O)-CH₂-CH₂-C(O)-NH-CH₂- | -CH₂-NH-C(O)-norbornenyl |
| 400 | H₂N-NH-C(O)-CH₂-CH₂-C(O)-NH-CH₂- | -CH₂-NH-C(O)-C≡CH |
| 401 | H₂N-NH-C(O)-CH₂-CH₂-C(O)-NH-CH₂- | -CH₂-NH-C(O)-CH₂-C≡CH |
| 402 | H₂N-NH-C(O)-CH₂-CH₂-C(O)-NH-CH₂- | -CH₂-NH-C(O)-CH₂-CH₂-C≡CH |
| 403 | H₂N-NH-C(O)-CH₂-CH₂-C(O)-NH-CH₂- | -CH₂-NH-C(O)-O-C(CH₃)₃ |
| 404 | H₂N-NH-C(O)-CH₂-CH₂-C(O)-NH-CH₂- | -CH₂-NH₂ |
| 405 | H₂N-NH-C(O)-CH₂-CH₂-C(O)-NH-CH₂- | -C(O)-C≡CH |

TABLE 15-continued

Exemplary Compounds

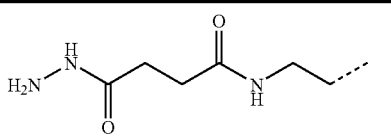

| # | $R^a$ | $R^b$ |
|---|---|---|
| 406 | 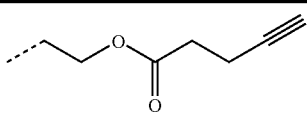 | 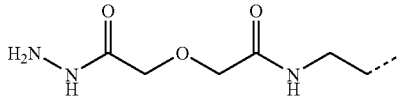 |

In certain embodiments, the present invention provides a compound as described herein, wherein the $L^1$ moiety of formula I is a $C_{1-10}$ membered alkylene wherein four methylene units of $L^1$ are replaced by —C(O)NH—, —NHC(O)—, —O—, and —NH—, and $R^1$ is hydrogen. Exemplary compounds include those set forth in Table 16, wherein n is as described in classes and subclasses herein. In certain embodiments, n is selected from 50±10. In other embodiments, n is selected from 80±10, 115±10, 180±10, or 225±10.

TABLE 16

Exemplary Compounds

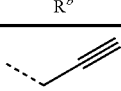

| # | $R^a$ | $R^b$ |
|---|---|---|
| 407 | 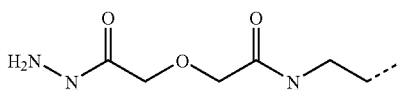 | 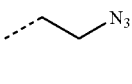 |
| 408 | 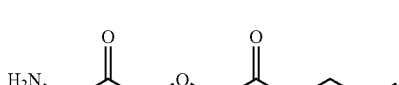 | 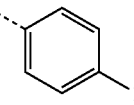 |
| 409 |  | 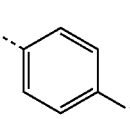 |
| 410 | 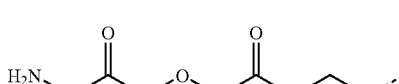 | 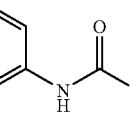 |
| 411 | 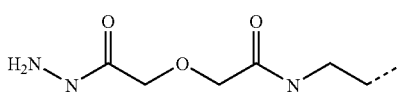 | 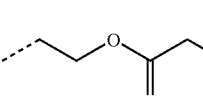 |
| 412 |  |  |

TABLE 16-continued

Exemplary Compounds $$R^a-O-\left(\phantom{\rule{0ex}{0ex}}\diagup\diagdown_O\right)_n-R^b$$

| # | $R^a$ | $R^b$ |
|---|---|---|
| 413 | H₂N-NH-C(O)-CH₂-O-CH₂-C(O)-NH-CH₂CH₂- | -CH₂CH₂-NH-C(O)-(CH₂)₄-biotinyl |
| 414 | H₂N-NH-C(O)-CH₂-O-CH₂-C(O)-NH-CH₂CH₂- | -CH₂CH₂-O-C(O)-(CH₂)₄-biotinyl |
| 415 | H₂N-NH-C(O)-CH₂-O-CH₂-C(O)-NH-CH₂CH₂- | -CH₂CH₂-NH-C(O)-C≡CH |
| 416 | H₂N-NH-C(O)-CH₂-O-CH₂-C(O)-NH-CH₂CH₂- | -CH₂CH₂-NH-C(O)-CH₂CH₂-C≡CH |
| 417 | H₂N-NH-C(O)-CH₂-O-CH₂-C(O)-NH-CH₂CH₂- | -CH₂CH₂-NH-C(O)-(CH₂)₃-C≡CH |
| 418 | H₂N-NH-C(O)-CH₂-O-CH₂-C(O)-NH-CH₂CH₂- | -CH₂CH₂-O-C(O)-(rhodamine B) |
| 419 | H₂N-NH-C(O)-CH₂-O-CH₂-C(O)-NH-CH₂CH₂- | 4-vinylphenyl- |
| 420 | H₂N-NH-C(O)-CH₂-O-CH₂-C(O)-NH-CH₂CH₂- | 4-(1,3-dioxolan-2-yl)phenyl- |

TABLE 16-continued

Exemplary Compounds $$R^a-O-(\phantom{x}-O\phantom{x})_n-R^b$$

| # | $R^a$ | $R^b$ |
|---|---|---|
| 421 | H₂N-NH-C(O)-CH₂-O-CH₂-C(O)-NH-CH₂CH₂- | -CH₂CH₂-P(O)(OEt)₂ |
| 422 | H₂N-NH-C(O)-CH₂-O-CH₂-C(O)-NH-CH₂CH₂- | -CH₂CH₂-S-S-(2-pyridyl) |
| 423 | H₂N-NH-C(O)-CH₂-O-CH₂-C(O)-NH-CH₂CH₂- | -C(O)-CH=CH₂ |
| 424 | H₂N-NH-C(O)-CH₂-O-CH₂-C(O)-NH-CH₂CH₂- | -C(O)-C(CH₃)=CH₂ |
| 425 | H₂N-NH-C(O)-CH₂-O-CH₂-C(O)-NH-CH₂CH₂- | -CH₂CH₂-NH-C(O)-CH=CH₂ |
| 426 | H₂N-NH-C(O)-CH₂-O-CH₂-C(O)-NH-CH₂CH₂- | -CH₂CH₂-NH-C(O)-C(CH₃)=CH₂ |
| 427 | H₂N-NH-C(O)-CH₂-O-CH₂-C(O)-NH-CH₂CH₂- | -CH₂CH₂-NH-C(O)-norbornenyl |
| 428 | H₂N-NH-C(O)-CH₂-O-CH₂-C(O)-NH-CH₂CH₂- | -CH₂CH₂-NH-C(O)-C≡CH |
| 429 | H₂N-NH-C(O)-CH₂-O-CH₂-C(O)-NH-CH₂CH₂- | -CH₂CH₂-O-C(O)-CH₂CH₂-C≡CH |
| 430 | H₂N-NH-C(O)-CH₂-O-CH₂-C(O)-NH-CH₂CH₂- | -CH₂CH₂-NH-C(O)-CH₂CH₂-C≡CH |
| 431 | H₂N-NH-C(O)-CH₂-O-CH₂-C(O)-NH-CH₂CH₂- | -CH₂CH₂-NH-C(O)-O-C(CH₃)₃ |

TABLE 16-continued

Exemplary Compounds $R^a\text{—O}\left(\phantom{x}\diagdown\text{O}\right)_n R^b$

| # | $R^a$ | $R^b$ |
|---|---|---|
| 432 | H₂N-NH-C(O)-CH₂-O-CH₂-C(O)-NH- | -CH₂CH₂-NH₂ |
| 433 | H₂N-NH-C(O)-CH₂-O-CH₂-C(O)-NH- | -C(O)-C≡CH |
| 434 | H₂N-NH-C(O)-CH₂-O-CH₂-C(O)-NH- | -CH₂CH₂-O-C(O)-CH₂CH₂-C≡CH |

In certain embodiments, the present invention provides a compound as described herein, wherein the $L^1$ moiety of formula I is a $C_{1-6}$ membered alkylene wherein two methylene units of $L^1$ are replaced by —C(O)NH— and —NH—, and $R^1$ is hydrogen. Exemplary compounds include those set forth in Table 17, wherein n is as described in classes and subclasses herein. In certain embodiments, n is selected from 50±10. In other embodiments, n is selected from 80±10, 115±10, 180±10, or 225±10.

TABLE 17

Exemplary Compounds $R^a\text{—O}\left(\phantom{x}\diagdown\text{O}\right)_n R^b$

| # | $R^a$ | $R^b$ |
|---|---|---|
| 435 | H₂N-NH-C(O)-CH₂CH₂CH₂- | -CH₂-C≡CH |
| 436 | H₂N-NH-C(O)-CH₂CH₂CH₂- | -CH₂CH₂-N₃ |
| 437 | H₂N-NH-C(O)-CH₂CH₂CH₂- | -C₆H₄-I |
| 438 | H₂N-NH-C(O)-CH₂CH₂CH₂- | -C₆H₄-Br |

TABLE 17-continued

Exemplary Compounds $$R^a\text{-}O\text{-}(\text{-}O\text{-})_n\text{-}R^b$$

| # | $R^a$ | $R^b$ |
|---|---|---|
| 439 | H₂N-NH-C(=O)-CH₂CH₂CH₂- (acyl hydrazide) | 4-(Boc-amino)phenyl |
| 440 | H₂N-NH-C(=O)-CH₂CH₂CH₂- | -CH₂CH₂-O-C(=O)-CH₂CH₂-C≡CH |
| 441 | H₂N-NH-C(=O)-CH₂CH₂CH₂- | -CH₂CH₂-NH-C(=O)-(CH₂)₄-biotinyl |
| 442 | H₂N-NH-C(=O)-CH₂CH₂CH₂- | -CH₂CH₂-O-C(=O)-(CH₂)₄-biotinyl |
| 443 | H₂N-NH-C(=O)-CH₂CH₂CH₂- | -CH₂CH₂-NH-C(=O)-C≡CH |
| 444 | H₂N-NH-C(=O)-CH₂CH₂CH₂- | -CH₂CH₂-NH-C(=O)-CH₂CH₂-C≡CH |
| 445 | H₂N-NH-C(=O)-CH₂CH₂CH₂- | -CH₂CH₂-NH-C(=O)-(CH₂)₃-C≡CH |
| 446 | H₂N-NH-C(=O)-CH₂CH₂CH₂- | rhodamine B ester (Cl⁻) |

TABLE 17-continued

Exemplary Compounds $$R^a\text{-}O\text{-}(\text{-}O\text{-})_n\text{-}R^b$$

| # | R$^a$ | R$^b$ |
|---|---|---|
| 447 | H$_2$N-NH-C(O)-CH$_2$CH$_2$CH$_2$- | 4-vinylphenyl |
| 448 | H$_2$N-NH-C(O)-CH$_2$CH$_2$CH$_2$- | 4-(1,3-dioxolan-2-yl)phenyl |
| 449 | H$_2$N-NH-C(O)-CH$_2$CH$_2$CH$_2$- | -CH$_2$CH$_2$-P(O)(OEt)$_2$ |
| 450 | H$_2$N-NH-C(O)-CH$_2$CH$_2$CH$_2$- | -CH$_2$CH$_2$-S-S-(2-pyridyl) |
| 451 | H$_2$N-NH-C(O)-CH$_2$CH$_2$CH$_2$- | -CH$_2$-C(O)-CH=CH$_2$ |
| 452 | H$_2$N-NH-C(O)-CH$_2$CH$_2$CH$_2$- | -CH$_2$-C(O)-C(CH$_3$)=CH$_2$ |
| 453 | H$_2$N-NH-C(O)-CH$_2$CH$_2$CH$_2$- | -CH$_2$CH$_2$-NH-C(O)-CH=CH$_2$ |
| 454 | H$_2$N-NH-C(O)-CH$_2$CH$_2$CH$_2$- | -CH$_2$CH$_2$-NH-C(O)-C(CH$_3$)=CH$_2$ |
| 455 | H$_2$N-NH-C(O)-CH$_2$CH$_2$CH$_2$- | -CH$_2$CH$_2$-NH-C(O)-(norbornenyl) |
| 456 | H$_2$N-NH-C(O)-CH$_2$CH$_2$CH$_2$- | -CH$_2$CH$_2$-NH-C(O)-C≡CH |

TABLE 17-continued

Exemplary Compounds $$R^a\text{-}O\underset{n}{\underbrace{(\phantom{xx}O\phantom{xx})}}R^b$$

| # | $R^a$ | $R^b$ |
|---|---|---|
| 457 | H₂N-NH-C(O)-CH₂CH₂CH₂-- | --CH₂CH₂-NH-C(O)-CH₂CH₂-C≡CH |
| 458 | H₂N-NH-C(O)-CH₂CH₂CH₂-- | --CH₂CH₂-NH-C(O)-CH₂CH₂CH₂-C≡CH |
| 459 | H₂N-NH-C(O)-CH₂CH₂CH₂-- | --CH₂CH₂-NH-C(O)-O-C(CH₃)₃ |
| 460 | H₂N-NH-C(O)-CH₂CH₂CH₂-- | --CH₂CH₂-NH₂ |
| 461 | H₂N-NH-C(O)-CH₂CH₂CH₂-- | --C(O)-C≡CH |
| 462 | H₂N-NH-C(O)-CH₂CH₂CH₂-- | --CH₂CH₂-O-C(O)-CH₂CH₂-C≡CH |

In certain embodiments, the present invention provides a compound as described herein, wherein the $L^1$ moiety of formula I is a $C_{1-6}$ membered alkylene wherein two methylene units of $L^1$ are replaced by —NH— and $R^1$ is hydrogen. Exemplary compounds include those set forth in Table 18, wherein n is as described in classes and subclasses herein. In certain embodiments, n is selected from 50±10. In other embodiments, n is selected from 80±10, 115±10, 180±10, or 225±10.

TABLE 18

Exemplary Compounds $$R^a\text{-}O\underset{n}{\underbrace{(\phantom{xx}O\phantom{xx})}}R^b$$

| # | $R^a$ | $R^b$ |
|---|---|---|
| 463 | H₂N-NH-CH₂CH₂-- | --CH₂-C≡CH |
| 464 | H₂N-NH-CH₂CH₂-- | --CH₂CH₂-N₃ |

TABLE 18-continued
Exemplary Compounds
$$R^a\text{—}O\left(\text{—}\!\!\!\!\overbrace{\phantom{xxxx}}^{}\!\!\!\!\text{—}O\right)_n\!\!R^b$$
| # | $R^a$ | $R^b$ |
|---|---|---|
| 465 | 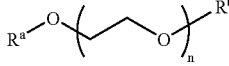 | 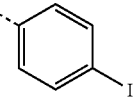 |
| 466 |  | 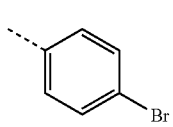 |
| 467 |  | 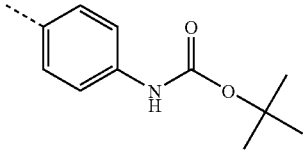 |
| 468 |  | 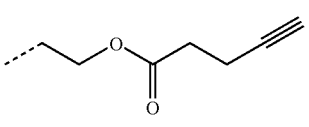 |
| 469 |  | 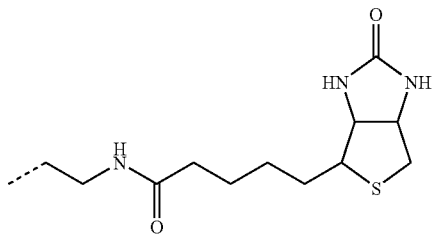 |
| 470 |  | 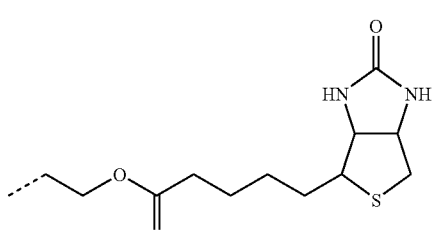 |
| 471 |  | 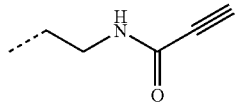 |
| 472 |  | 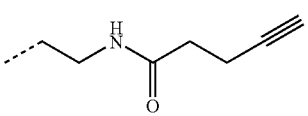 |

TABLE 18-continued

Exemplary Compounds $$R^a\text{-O}\left(\underset{}{\overset{}{\phantom{X}}}\text{O}\right)_n R^b$$

| # | R$^a$ | R$^b$ |
|---|---|---|
| 473 | H$_2$N-NH-CH$_2$CH$_2$- | -CH$_2$CH$_2$-NH-C(O)-CH$_2$CH$_2$-C≡CH |
| 474 | H$_2$N-NH-CH$_2$CH$_2$- | rhodamine B ester group |
| 475 | H$_2$N-NH-CH$_2$CH$_2$- | 4-vinylphenyl |
| 476 | H$_2$N-NH-CH$_2$CH$_2$- | 4-(1,3-dioxolan-2-yl)phenyl |
| 477 | H$_2$N-NH-CH$_2$CH$_2$- | -CH$_2$CH$_2$-P(O)(OEt)$_2$ |
| 478 | H$_2$N-NH-CH$_2$CH$_2$- | -CH$_2$CH$_2$-S-S-(2-pyridyl) |
| 479 | H$_2$N-NH-CH$_2$CH$_2$- | -C(O)-CH=CH$_2$ |
| 480 | H$_2$N-NH-CH$_2$CH$_2$- | -C(O)-C(CH$_3$)=CH$_2$ |

TABLE 18-continued

Exemplary Compounds $$R^a\text{-}O\text{-}(\text{CH}_2\text{CH}_2\text{O})_n\text{-}R^b$$

| # | $R^a$ | $R^b$ |
|---|---|---|
| 481 | H₂N-NH-CH₂CH₂- | -CH₂CH₂-NH-C(O)-CH=CH₂ |
| 482 | H₂N-NH-CH₂CH₂- | -CH₂CH₂-NH-C(O)-C(CH₃)=CH₂ |
| 483 | H₂N-NH-CH₂CH₂- | -CH₂CH₂-NH-C(O)-norbornenyl |
| 484 | H₂N-NH-CH₂CH₂- | -CH₂CH₂-NH-C(O)-C≡CH |
| 485 | H₂N-NH-CH₂CH₂- | -CH₂CH₂-NH-C(O)-CH₂CH₂-C≡CH |
| 486 | H₂N-NH-CH₂CH₂- | -CH₂CH₂-NH-C(O)-CH₂CH₂CH₂-C≡CH |
| 487 | H₂N-NH-CH₂CH₂- | -CH₂CH₂-NH-C(O)-O-C(CH₃)₃ |
| 488 | H₂N-NH-CH₂CH₂- | -CH₂CH₂-NH₂ |
| 489 | H₂N-NH-CH₂CH₂- | -C(O)-C≡CH |

TABLE 18-continued

Exemplary Compounds

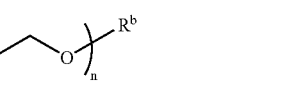

| # | $R^a$ | $R^b$ |
|---|---|---|
| 490 |  | 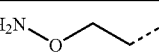 |
| 491 | 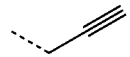 | 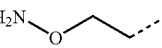 |

In certain embodiments, the present invention provides a compound as described herein, wherein the $L^1$ moiety of formula I is a $C_{1-6}$ membered alkylene wherein two methylene units of $L^1$ are replaced by —O— and —NH—, and $R^1$ is hydrogen. Exemplary compounds include those set forth in Table 19, wherein n is as described in classes and subclasses herein. In certain embodiments, n is selected from 50±10. In other embodiments, n is selected from 80±10, 115±10, 180±10, or 225±10.

TABLE 19

Exemplary Compounds

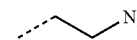

| # | $R^a$ | $R^b$ |
|---|---|---|
| 492 | 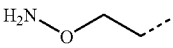 | 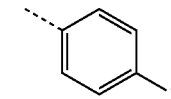 |
| 493 | 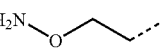 | 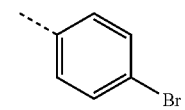 |
| 494 | 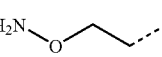 | 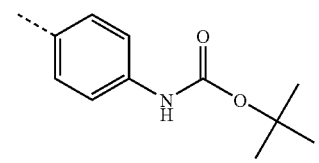 |
| 495 | 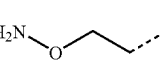 | 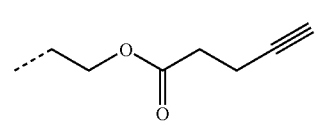 |
| 496 | H₂N—O— | (p-phenyl)-NH-C(=O)-O-C(CH₃)₃ |
| 497 | H₂N—O— | —CH₂CH₂-O-C(=O)-CH₂CH₂-C≡CH |

TABLE 19-continued

Exemplary Compounds $$R^a-O-(-\text{CH}_2\text{CH}_2-O-)_n-R^b$$

| # | $R^a$ | $R^b$ |
|---|---|---|
| 498 | H₂N–O–CH₂CH₂– | –CH₂CH₂–NH–C(O)–(CH₂)₄–biotinyl |
| 499 | H₂N–O–CH₂CH₂– | –CH₂CH₂–O–C(O)–(CH₂)₄–biotinyl |
| 500 | HO–NH–CH₂CH₂– | –CH₂CH₂–NH–C(O)–C≡CH |
| 501 | H₂N–O–CH₂CH₂– | –CH₂CH₂–NH–C(O)–CH₂CH₂–C≡CH |
| 502 | H₂N–O–CH₂CH₂– | –CH₂CH₂–NH–C(O)–(CH₂)₃–C≡CH |
| 503 | H₂N–O–CH₂CH₂– | –CH₂CH₂–O–C(O)–(2-rhodamine B aryl ester), Cl⁻ |
| 504 | H₂N–O–CH₂CH₂– | –(4-vinylphenyl) |
| 505 | H₂N–O–CH₂CH₂– | –(4-(1,3-dioxolan-2-yl)phenyl) |

TABLE 19-continued

Exemplary Compounds $$R^a\text{—}O\!\left(\phantom{\!}\!\!\!\!\!\!\!\right)_{\!n}\!\!R^b$$

| # | $R^a$ | $R^b$ |
|---|---|---|
| 506 | H₂N–O–CH₂CH₂– | –CH₂CH₂–P(=O)(OEt)₂ (diethyl phosphonate) |
| 507 | H₂N–O–CH₂CH₂– | –CH₂CH₂–S–S–(2-pyridyl) |
| 508 | H₂N–O–CH₂CH₂– | acryloyl (–C(=O)CH=CH₂) |
| 509 | H₂N–O–CH₂CH₂– | methacryloyl (–C(=O)C(CH₃)=CH₂) |
| 510 | H₂N–O–CH₂CH₂– | –CH₂CH₂–NH–C(=O)–CH=CH₂ (acrylamide) |
| 511 | H₂N–O–CH₂CH₂– | –CH₂CH₂–NH–C(=O)–C(CH₃)=CH₂ (methacrylamide) |
| 512 | H₂N–O–CH₂CH₂– | –CH₂CH₂–NH–C(=O)–(norbornenyl) |
| 513 | H₂N–O–CH₂CH₂– | –CH₂CH₂–NH–C(=O)–C≡CH |
| 514 | H₂N–O–CH₂CH₂– | –CH₂CH₂–NH–C(=O)–CH₂CH₂–C≡CH |
| 515 | H₂N–O–CH₂CH₂– | –CH₂CH₂–NH–C(=O)–CH₂CH₂CH₂–C≡CH |
| 516 | H₂N–O–CH₂CH₂– | –CH₂CH₂–NH–C(=O)–O–C(CH₃)₃ (Boc) |

TABLE 19-continued

Exemplary Compounds $$R^a\text{—O}\left(\diagdown\diagup\text{O}\right)_n R^b$$

| # | $R^a$ | $R^b$ |
|---|---|---|
| 517 | H₂N–O–CH₂CH₂– | –CH₂CH₂–NH₂ |
| 518 | H₂N–O–CH₂CH₂– | –C(O)–C≡CH |
| 519 | H₂N–O–CH₂CH₂– | –CH₂CH₂–O–C(O)–CH₂CH₂–C≡CH |

In certain embodiments, the present invention provides a compound as described herein, wherein the $L^1$ moiety of formula I is a $C_{1-6}$ membered alkylene wherein one methylene unit of $L^1$ is replaced by —O— and $R^1$ is —CN. Exemplary compounds include those set forth in Table 20, wherein n is as described in classes and subclasses herein. In certain embodiments, n is selected from 50±10. In other embodiments, n is selected from 80±10, 115±10, 180±10, or 225±10.

TABLE 20

Exemplary Compounds $$R^a\text{—O}\left(\diagdown\diagup\text{O}\right)_n R^b$$

| # | $R^a$ | $R^b$ |
|---|---|---|
| 520 | OCN–CH₂CH₂– | –C≡CH |
| 521 | OCN–CH₂CH₂– | –CH₂CH₂–N(maleimide) |
| 522 | OCN–CH₂CH₂– | –C₆H₄–CHO (para) |
| 523 | OCN–CH₂CH₂– | –CH₂CH₂–N₃ |
| 524 | OCN–CH₂CH₂– | –C₆H₄–I (para) |
| 525 | OCN–CH₂CH₂– | –C₆H₄–Br (para) |

TABLE 20-continued

Exemplary Compounds $$R^a\!-\!O\!\left(\!\!\begin{array}{c}\\ \\ \end{array}\!\!O\!\right)_{\!n}\!\!R^b$$

| # | $R^a$ | $R^b$ |
|---|---|---|
| 526 | OCN–CH₂CH₂– | 4-(Boc-NH)phenyl– |
| 527 | OCN–CH₂CH₂– | –CH₂CH₂OC(O)CH₂CH₂C≡CH |
| 528 | OCN–CH₂CH₂– | biotinamidoethyl– |
| 529 | OCN–CH₂CH₂– | biotin ester (ethyl pentanoate linker) |
| 530 | OCN–CH₂CH₂– | –CH₂CH₂S-S-(2-pyridyl) |
| 531 | OCN–CH₂CH₂– | acryloyl– |
| 532 | OCN–CH₂CH₂– | methacryloyl– |
| 533 | OCN–CH₂CH₂– | norbornenyl carbonyl– |
| 534 | OCN–CH₂CH₂– | –CH₂CH₂NHC(O)CH=CH₂ |

TABLE 20-continued

Exemplary Compounds $$R^a-O-(CH_2CH_2O)_n-R^b$$

| # | $R^a$ | $R^b$ |
|---|---|---|
| 535 | OCN-CH2CH2- | -CH2CH2-NH-C(=O)-C(CH3)=CH2 |
| 536 | OCN-CH2CH2- | -CH2CH2-NH-C(=O)-norbornenyl |
| 537 | OCN-CH2CH2- | -(4-vinylphenyl) |
| 538 | OCN-CH2CH2- | -(4-(1,3-dioxolan-2-yl)phenyl) |
| 539 | OCN-CH2CH2- | -CH2CH2-P(=O)(OEt)2 |
| 540 | OCN-CH2CH2- | -CH2CH2-NH-C(=O)-C≡CH |
| 541 | OCN-CH2CH2- | -CH2CH2-NH-C(=O)-CH2CH2-C≡CH |
| 542 | OCN-CH2CH2- | -CH2CH2-NH-C(=O)-CH2CH2CH2-C≡CH |
| 543 | OCN-CH2CH2- | rhodamine B ester |

TABLE 20-continued

Exemplary Compounds $$R^a\text{-O-}(\text{CH}_2\text{CH}_2\text{-O})_n\text{-}R^b$$

| # | $R^a$ | $R^b$ |
|---|-------|-------|
| 544 | OCN–CH₂CH₂– | –C(=O)–C≡CH |

In certain embodiments, the present invention provides a compound as described herein, wherein the $L^1$ moiety of formula I is a $C_{1-6}$ membered alkylene wherein one methylene unit of $L^1$ is replaced by —S— and $R^1$ is —H. Exemplary compounds include those set forth in Table 21, wherein n is as described in classes and subclasses herein. In certain embodiments, n is selected from 50±10. In other embodiments, n is selected from 80±10, 115±10, 180±10, or 225±10.

TABLE 21

Exemplary Compounds $$R^a\text{-O-}(\text{CH}_2\text{CH}_2\text{-O})_n\text{-}R^b$$

| # | $R^a$ | $R^b$ |
|---|-------|-------|
| 545 | HS–CH₂CH₂– | –CH₂CH₂–S–C(C₆H₅)₃ |
| 546 | HS–CH₂CH₂– | –C≡CH |
| 547 | HS–CH₂CH₂– | –C₆H₄–COOH |
| 548 | HS–CH₂CH₂– | –C₆H₄–CHO |
| 549 | HS–CH₂CH₂– | –CH₂CH₂–N₃ |
| 550 | HS–CH₂CH₂– | –C₆H₄–I |
| 551 | HS–CH₂CH₂– | –C₆H₄–Br |

TABLE 21-continued

Exemplary Compounds $$R^a\text{—O}\left(\phantom{\rule{0ex}{0ex}}\text{—O}\phantom{\rule{0ex}{0ex}}\right)_n R^b$$

| # | $R^a$ | $R^b$ |
|---|---|---|
| 552 | HS–CH₂CH₂– | 4-vinylphenyl |
| 553 | HS–CH₂CH₂– | –CH₂CH₂P(=O)(OEt)₂ |
| 554 | HS–CH₂CH₂– | –CH₂CH₂P(=O)(OH)₂ |
| 555 | HS–CH₂CH₂– | biotinamidoethyl |
| 556 | HS–CH₂CH₂– | biotin ester (ethyl) |
| 557 | HS–CH₂CH₂– | 4-aminophenyl |
| 558 | HS–CH₂CH₂– | acryloyl |
| 559 | HS–CH₂CH₂– | methacryloyl |
| 560 | HS–CH₂CH₂– | norbornenecarbonyl |

TABLE 21-continued

Exemplary Compounds $$R^a-O-(\!\!-\!\!\diagup\!\!\diagdown\!\!-\!\!O\!\!-\!\!)_n\!\!-\!\!R^b$$

| # | $R^a$ | $R^b$ |
|---|---|---|
| 561 | HS⁓ | ⁓NHC(O)CH=CH₂ (acrylamide) |
| 562 | HS⁓ | ⁓NHC(O)C(CH₃)=CH₂ (methacrylamide) |
| 563 | HS⁓ | ⁓NHC(O)-norbornenyl |
| 564 | HS⁓ | ⁓-C₆H₄-CH₂NH₂ |
| 565 | HS⁓ | ⁓NHC(O)C≡CH |
| 566 | HS⁓ | ⁓NHC(O)CH₂CH₂C≡CH |
| 567 | HS⁓ | ⁓NHC(O)CH₂CH₂CH₂C≡CH |
| 568 | HS⁓ | ⁓OC(O)CH₂CH₂C≡CH |
| 569 | HS⁓ | ⁓C(O)C≡CH |
| 570 | HS⁓ | rhodamine B ester (via propyl linker) |

TABLE 21-continued

Exemplary Compounds $R^a\text{-O-}(\text{-CH}_2\text{CH}_2\text{-O-})_n\text{-}R^b$

| # | $R^a$ | $R^b$ |
|---|-------|-------|
| 571 | HS-CH₂CH₂- | -CH₂-C(=O)-OH |
| 572 | HS-CH₂CH₂- | -CH₂-C(=O)-OH |

In certain embodiments, the present invention provides a compound as described herein, wherein $R^1$ is a protected thiol moiety. Exemplary compounds include those set forth in Table 22, wherein n is as described in classes and subclasses herein. In certain embodiments, n is selected from 50±10. In other embodiments, n is selected from 80±10, 115±10, 180±10, or 225±10.

TABLE 22

Exemplary Compounds $R^a\text{-O-}(\text{-CH}_2\text{CH}_2\text{-O-})_n\text{-}R^b$

| # | $R^a$ | $R^b$ |
|---|-------|-------|
| 573 | tBu-S-CH₂CH₂- | -C₆H₄-NH₂ |
| 574 | tBu-S-CH₂CH₂- | -C₆H₄-C(=O)OH |
| 575 | tBu-S-CH₂CH₂- | -CH₂CH₂-NH₂ |
| 576 | tBu-S-CH₂CH₂- | -CH₂CH₂-SH |

In certain embodiments, the present invention provides a compound as described herein, wherein $R^1$ is $C_{1-6}$ aliphatic and, in certain embodiments, alkenyl. Exemplary compounds include those set forth in Table 23, wherein n is as described in classes and subclasses herein. In certain embodiments, n is selected from 50±10. In other embodiments, n is selected from 80±10, 115±10, 180±10, or 225±10.

TABLE 23

Exemplary Compounds $R^a\text{-O-}(\text{-CH}_2\text{CH}_2\text{-O-})_n\text{-}R^b$

| # | $R^a$ | $R^b$ |
|---|-------|-------|
| 577 | CH₂=CH-CH₂- | -CH₂CH₂-SH |
| 578 | CH₂=CH-CH₂- | -CH₂CH₂-NH₂ |
| 579 | CH₂=CH-CH₂- | -C₆H₄-C(=O)OH |
| 580 | CH₂=CH-CH₂- | -CH₂CH₂-NH-C(=O)-O-tBu |

In certain embodiments, the present invention provides a compound as described herein, wherein $R^1$ is a bicyclic, partially unsaturated 7 membered ring. Exemplary compounds include those set forth in Table 24, wherein n is as described in classes and subclasses herein. In certain embodiments, n is selected from 50±10. In other embodiments, n is selected from 80±10, 115±10, 180±10, or 225±10.

TABLE 24

Exemplary Compounds $R^a\text{-O-}(\text{-CH}_2\text{CH}_2\text{-O-})_n\text{-}R^b$

| # | $R^a$ | $R^b$ |
|---|-------|-------|
| 581 | norbornenyl-CH₂- | -CH₂CH₂-SH |

TABLE 24-continued

Exemplary Compounds $R^a\text{-}O\text{-}(\text{CH}_2\text{CH}_2\text{O})_n\text{-}R^b$

| # | $R^a$ | $R^b$ |
|---|---|---|
| 582 | norbornenyl-CH₂– | –CH₂CH₂NH₂ |
| 583 | norbornenyl-CH₂– | –C₆H₄–COOH (para) |
| 584 | norbornenyl-CH₂– | –CH₂CH₂–NH–C(O)–O–C(CH₃)₃ |

In certain embodiments, the present invention provides a compound selected from those set forth in Table 25, wherein n is as described in classes and subclasses herein. In certain embodiments, n is selected from 50±10. In other embodiments, n is selected from 80±10, 115±10, 180±10, or 225±10.

TABLE 25

Exemplary Compounds $R^a\text{-}O\text{-}(\text{CH}_2\text{CH}_2\text{O})_n\text{-}R^b$

| # | $R^a$ | $R^b$ |
|---|---|---|
| 585 | $N_3$–CH₂CH₂CH₂– | 4-(NHS-OC(O)-CH(CH₃)-CH₂-O)-C₆H₄– |
| 586 | $N_3$–CH₂CH₂CH₂– | 4-(NHS-OC(O))-C₆H₄– |
| 587 | $N_3$–CH₂CH₂CH₂– | 4-((4-NO₂-C₆H₄-O-C(O))-C₆H₄– |
| 588 | $N_3$–CH₂CH₂CH₂– | 4-(NHS-OC(O)-CH₂-CH(CH₃)-O)-C₆H₄– |
| 589 | $N_3$–CH₂CH₂CH₂– | –CH₂CH₂CH₂-C(O)-O-NHS |

TABLE 25-continued

Exemplary Compounds $$R^a-O-(\phantom{x}O\phantom{x})_n-R^b$$

| # | $R^a$ | $R^b$ |
|---|---|---|
| 590 | N₃-CH₂CH₂- | N-(oxanorbornene dicarboximide)ethyl |
| 591 | N₃-CH₂CH₂- | -CH₂CH₂-S-C(O)CH₃ |
| 592 | H₂N-CH₂CH₂- | -CH₂CH₂-NH-C(O)CF₃ |
| 593 | H₂N-CH₂CH₂- | N-(oxanorbornene dicarboximide)ethyl |
| 594 | H₂N-CH₂CH₂- | -CH₂CH₂-S-C(O)CH₃ |
| 595 | HC≡C-CH₂- | N-(oxanorbornene dicarboximide)ethyl |
| 596 | HOOC-CH₂CH₂CH₂- | N-(oxanorbornene dicarboximide)ethyl |
| 597 | (oxazoline)-CH₂CH₂CH₂- | N-(oxanorbornene dicarboximide)ethyl |
| 598 | HC≡C-CH₂- | -CH₂CH₂-S-C(O)CH₃ |
| 599 | OHC-CH₂- | -CH₂CH₂-S-C(O)CH₃ |

TABLE 25-continued

Exemplary Compounds

| # | R^a | R^b |
|---|---|---|
| 600 | (HOOC-propyl-) | (-CH2CH2-S-C(=O)-CH3) |
| 601 | (H2N-CH2CH2-) | (-CH2CH2-SH) |

4. General Methods of Providing the Present Compounds:

Compounds of this invention may be prepared in general by synthetic methods known to those skilled in the art for analogous compounds and as illustrated by the general schemes and the preparative examples that follow. In certain embodiments, compounds of the present invention are prepared by methods as described in detail in United States patent application entitled "Heterobifunctional poly(ethylene glycol) and Uses Thereof" filed Oct. 24, 2005, and given Ser. No. 11/256,735, the entirety of which is hereby incorporated herein by reference.

(c) to form the hydroxyl compound 4. Compound 4 is then derivatized to afford a compound of formula I by methods known in the art.

One of ordinary skill in the art will recognize that the derivatization of a compound of formula 4 to form a compound of formula I may be achieved in a single step or via a multi-step process. For example, the hydroxyl group of formula 4 can be converted to a suitable leaving group which is then displaced by a nucleophile to form a compound of formula I. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy,

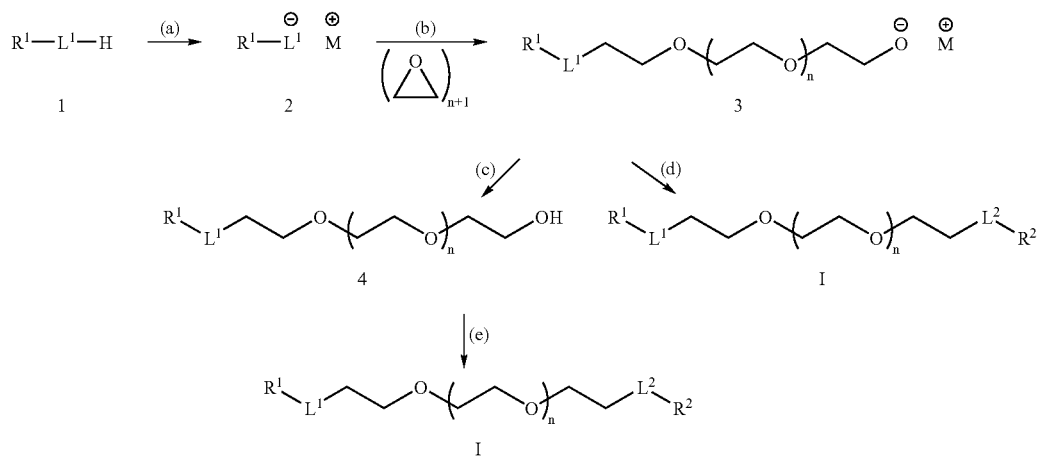

Scheme I

Scheme I above shows a general method for preparing compounds of the present invention. At step (a), the polymerization initiator is treated with a suitable base to form 2. A variety of bases are suitable for the reaction at step (a). Such bases include, but are not limited to, potassium naphthalenide, diphenylmethyl potassium, triphenylmethyl potassium, and potassium hydride. At step (b), the resulting anion is treated with ethylene oxide to form the polymer 3. Polymer 3 can be transformed at step (d) to a compound of formula I directly by terminating the living polymer chain-end of 3 with a suitable polymerization terminator to afford a compound of formula I. Alternatively, polymer 3 may be quenched at step optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy (mesyloxy), tosyloxy, triflyloxy, nitro-phenylsulfonyloxy (nosyloxy), and bromo-phenylsulfonyloxy (brosyloxy).

According to an alternate embodiment, the suitable leaving group may be generated in situ within a reaction medium. For example, a leaving group may be generated in situ from a precursor of that compound wherein said precursor contains a group readily replaced by said leaving group in situ.

Derivatization of the hydroxyl group of formula 4 can be achieved using methods known to one of ordinary skill in the art to obtain a variety of compounds. For example, said hydroxyl group may be transformed to a protected hydroxyl group, or, alternatively, to a suitable leaving group. Hydroxyl protecting groups are well known and include those described above and herein. Such transformations are known to one skilled in the art and include, among others, those described herein.

An exemplary transformation includes coupling of the hydroxyl group of formula 4 with an acid to form an ester thereof. Once of ordinary skill in the art would recognize that this transformation would result in compounds of formula I wherein $L^2$ is a bivalent, saturated or unsaturated, straight or branched $C_{1-12}$ alkylene chain, as defined and described herein, wherein the terminal methylene group is replaced by —C(O)O—. Such coupling reactions are well known in the art. In certain embodiments, the coupling is achieved with a suitable coupling reagent. Such reagents are well known in the art and include, for example, DCC and EDC, among others. In other embodiments, the carboxylic acid moiety is activated for use in the coupling reaction. Such activation includes formation of an acyl halide, use of a Mukaiyama reagent, and the like. These methods, and others, are known to one of ordinary skill in the art, e.g., see, "Advanced Organic Chemistry," Jerry March, 5$^{th}$ Ed., pp. 351-357, John Wiley and Sons, N.Y.

In certain embodiments, the $R^2$-$L^2$- group of formula I is incorporated at either of steps (b) or (e) by derivatization of the hydroxyl group of formula 4 via Mitsunobu coupling. The Mitsunobu reaction is a mild method for achieving formal substitution of the hydroxyl group using azodicarboxylic esters/amides and triphenylphosphine (TPP) or trialkylphosphines or phosphites. In addition, other azo compounds have been developed as alternatives to the traditional azodicarboxylic esters diethylazodicarboxylate (DEAD) and diisopropylazodicarboxylate (DIAD). These include dibenzyl azodicarboxylate (DBAD), N,N,N',N'-tetramethylazodicarbonamide (TMAD), and dipiperidyl azodicarboxylate (DPAD). Mitsunobu coupling provides access to terminal groups including, but not limited to, halides, azide, amines, esters, ethers, thioethers and isothiocyanates. Accordingly, it will be appreciated that a variety of compounds of formula I are obtained by the derivatization of the hydroxyl group of formula 4 by Mitsunobu reaction.

In certain embodiments, the polymerization terminating agent is one that is capable of Mistunobu coupling. These include optionally substituted phenols, optionally substituted thiophenols, cyclic imides, carboxylic acids, azide, and other reagents capable of Mitsunobu coupling. Such Mitsunobu terminating agents include, but are not limited to, those set forth in Table 26, below.

TABLE 26

Representative Mitsunobu Polymerization Terminating Agents

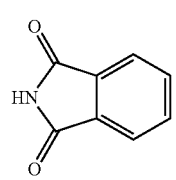

M-1

TABLE 26-continued

Representative Mitsunobu Polymerization Terminating Agents

M-2

M-3

M-4

M-5

M-6

M-7

M-8

M-9

M-10

TABLE 26-continued
Representative Mitsunobu Polymerization Terminating Agents
M-11 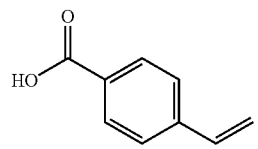
M-12 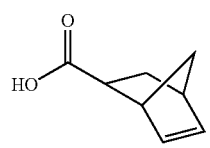
M-13 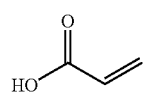
M-14 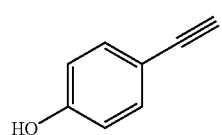
M-15 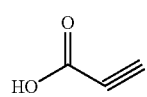
M-16 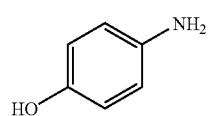
M-17 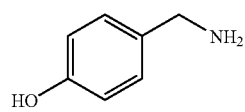
M-18 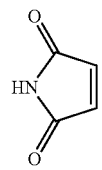
M-19 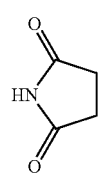
TABLE 26-continued
Representative Mitsunobu Polymerization Terminating Agents
M-20 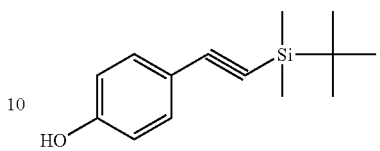
M-21 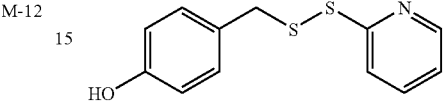
M-22 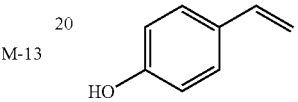
M-23 
M-24 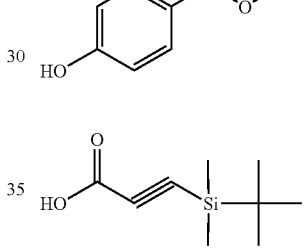
M-25 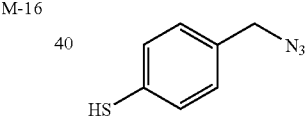
M-26 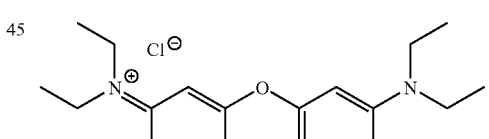
M-27 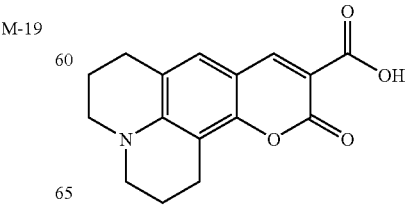

TABLE 26-continued
Representative Mitsunobu Polymerization Terminating Agents
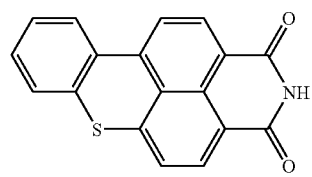
M-28
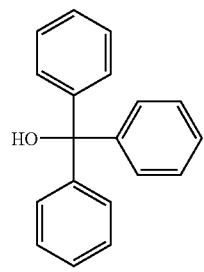
M-29
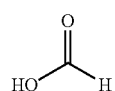
M-30
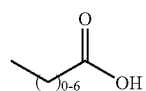
M-31
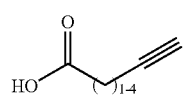
M-32
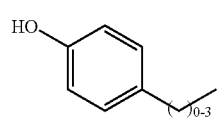
M-33
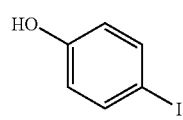
M-34
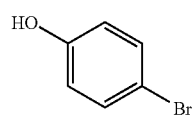
M-35
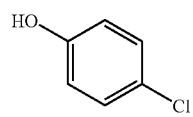
M-36
TABLE 26-continued
Representative Mitsunobu Polymerization Terminating Agents
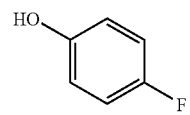
M-37
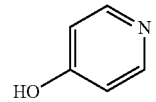
M-38
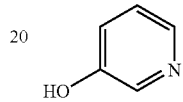
M-39
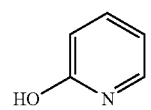
M-40
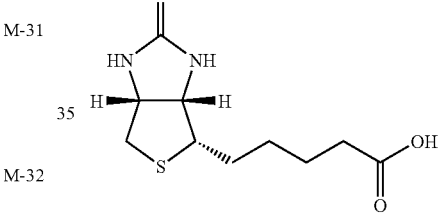
M-41
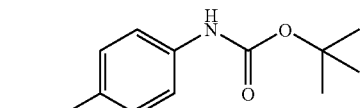
M-42
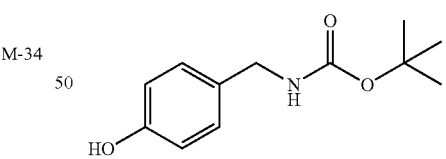
M-43
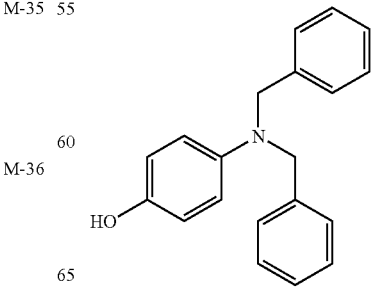
M-44

TABLE 26-continued

Representative Mitsunobu Polymerization Terminating Agents

NaBr     M-60
NaI     M-61
H—N₃     M-62
Na—N₃     M-63

TABLE 26-continued
Representative Mitsunobu Polymerization Terminating Agents
M-64
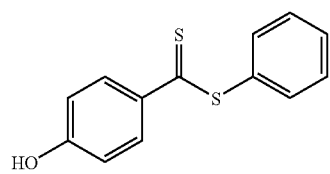
M-65
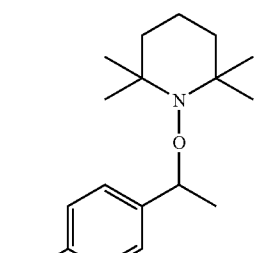
M-66
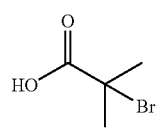
M-67
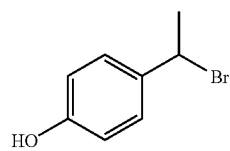
M-68
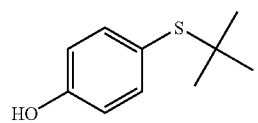
M-69
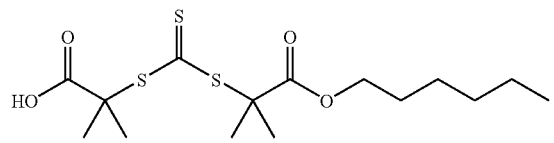
M-70
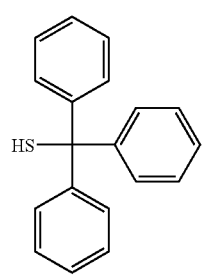
TABLE 26-continued
Representative Mitsunobu Polymerization Terminating Agents
M-71
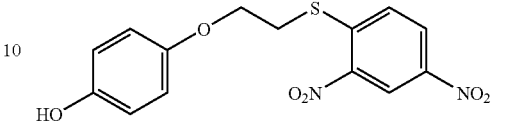
M-72
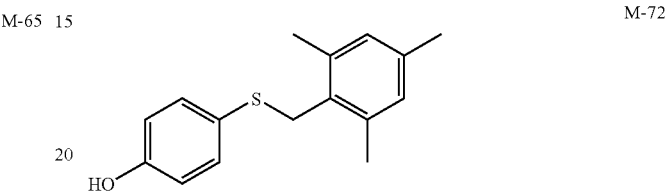
M-73
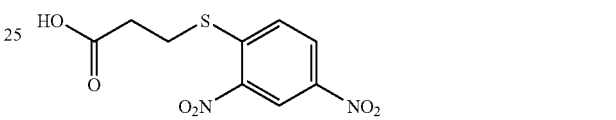
M-74
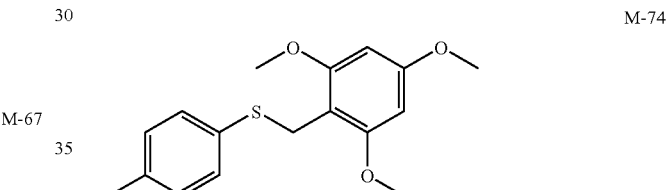
M-75
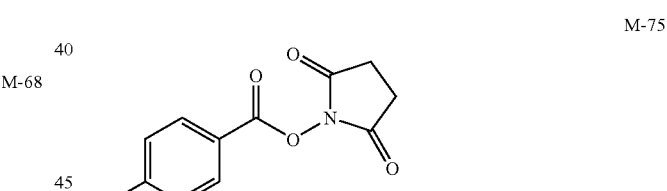
M-76
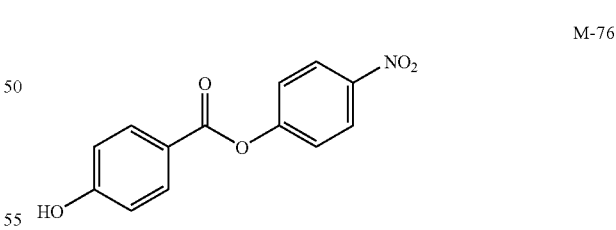
M-77
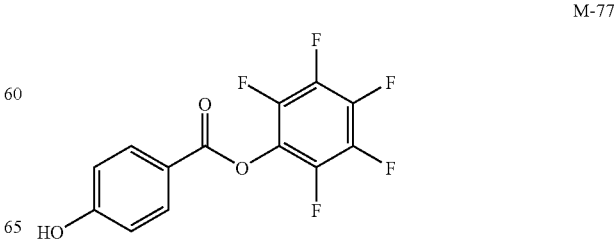

TABLE 26-continued

Representative Mitsunobu Polymerization Terminating Agents

M-78, M-79, M-80, M-81, M-82, M-83, M-84, M-85

TABLE 26-continued

Representative Mitsunobu Polymerization Terminating Agents

M-86

In other embodiments, the $R^2$-$L^2$- group of formula I is incorporated by derivatization of the hydroxyl group of formula 4 via anhydride coupling. One of ordinary skill in the art would recognize that anhydride polymerization terminating agents containing an azide, an aldehyde, a protected hydroxyl, an alkyne, and other groups, may be used to incorporate said azide, said aldehyde, said protected hydroxyl, said alkyne, and other groups into the $R^2$-$L^2$- group of compounds of formula I. It will also be appreciated that such anhydride polymerization terminating agents are also suitable for terminating the living polymer chain-end of a compound of formula 3. Such anhydride polymerization terminating agents include, but are not limited to, those set forth in Table 27, below.

TABLE 27

Representative Anhydride Polymerization Terminating Agents

A-1, A-2, A-3, A-4, A-5, A-6, A-7

TABLE 27-continued

Representative Anhydride Polymerization Terminating Agents

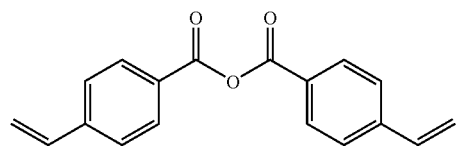
A-8

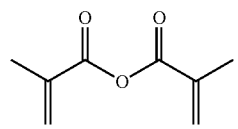
A-9

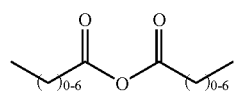
A-10

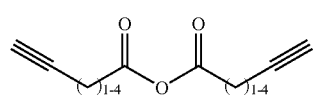
A-11

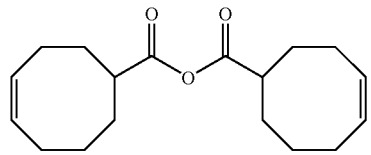
A-12

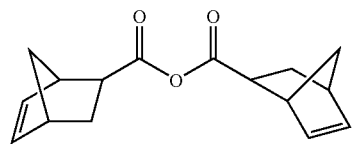
A-13

In other embodiments, the $R^2\text{-}L^2$- group of formula I is incorporated by derivatization of the hydroxyl group of formula 4 via reaction with a polymerization terminating agent having a suitable leaving group. It will also be appreciated that such polymerization terminating agents are also suitable for terminating the living polymer chain-end of a compound of formula 3. Examples of these polymerization terminating agents include, but are not limited to, those set forth in Table 28, below.

TABLE 28

Representative Polymerization Terminating Agents

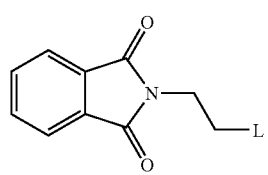
L-1

TABLE 28-continued

Representative Polymerization Terminating Agents

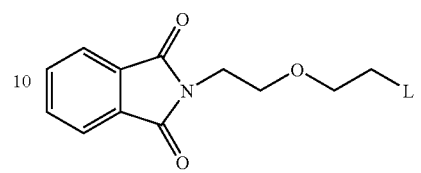
L-2

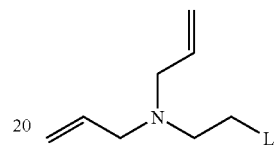
L-3

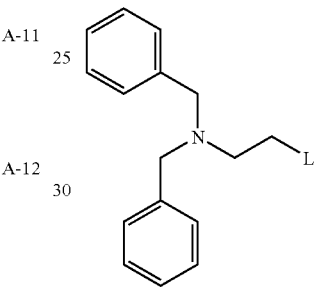
L-4

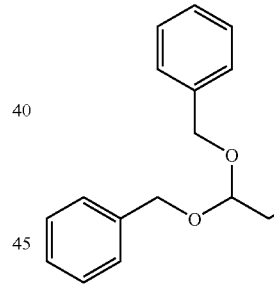
L-5

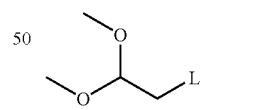
L-6

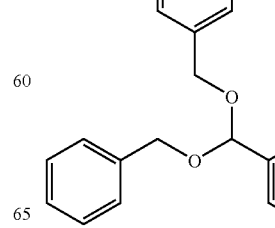
L-7

TABLE 28-continued
Representative Polymerization Terminating Agents
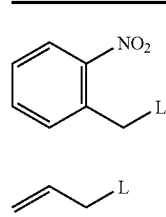
L-8
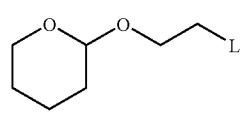
L-9
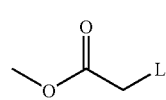
L-10
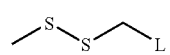
L-11
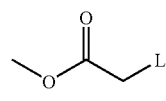
L-12
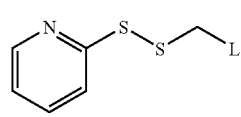
L-13
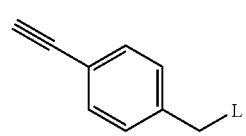
L-14
L-15
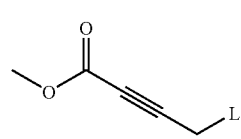
L-16
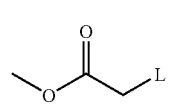
L-17
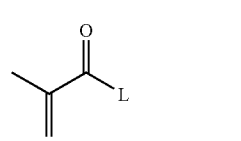
L-18
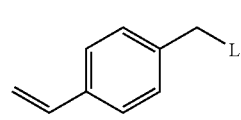
L-19
TABLE 28-continued
Representative Polymerization Terminating Agents
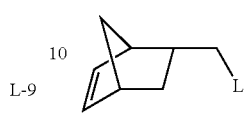
L-20
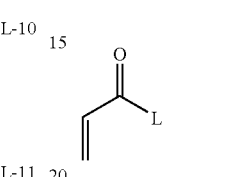
L-21
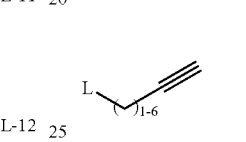
L-22
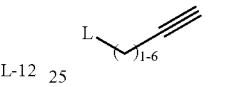
L-23
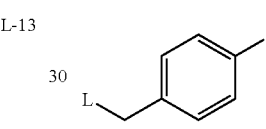
L-24
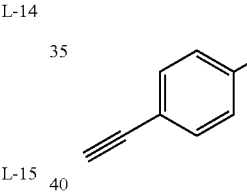
L-25
L-26
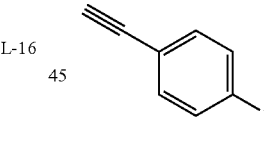
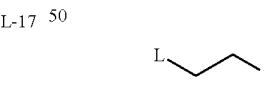
L-27
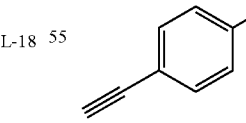
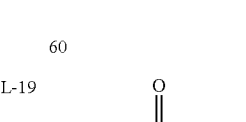

TABLE 28-continued

Representative Polymerization Terminating Agents

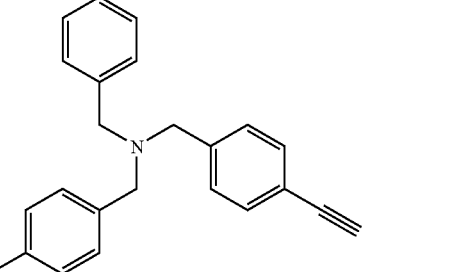

L-28

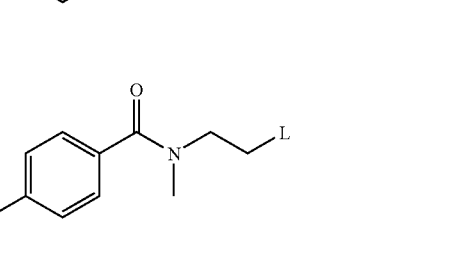

L-29

L-30

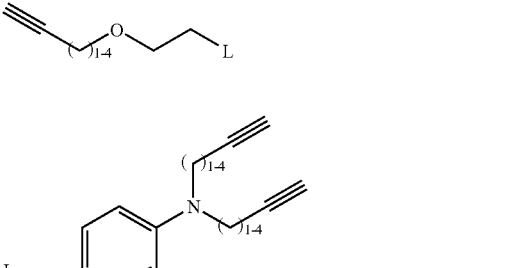

L-31

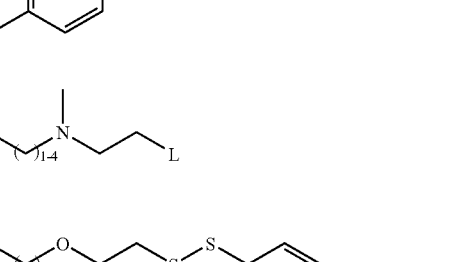

L-32

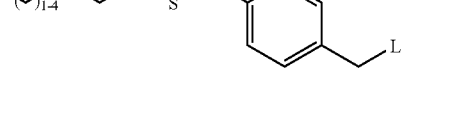

L-33

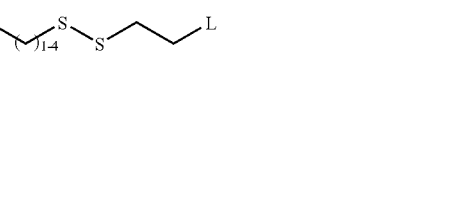

L-34

L-35

L-36

TABLE 28-continued

Representative Polymerization Terminating Agents

L-37

L-38

L-39

L-40

L-41

L-42

L-43

L-44 wherein each L is a suitable leaving group as defined above and in classes and subclasses as described above and herein.

One of ordinary skill in the art will recognize that certain of the terminating groups depicted in Tables 26, 27, and 28 comprise protected functional groups. It will be appreciated that these protecting groups are optionally removed to form compounds of the present invention. Methods for the deprotection of functional groups are well known to one of ordinary skill in the art and include those described in detail in Greene (1999).

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

5. Uses, Methods, and Compositions

As discussed above, the present invention provides bifunctional PEG's, intermediates thereto, and methods of preparing the same. Such functionalized PEG's are useful for a variety of purposes in the pharmaceutical and biomedical fields. Such uses include using the bifunctional PEG's of the present invention in the process of PEGylating other molecules or substrates. Accordingly, another embodiment of the present invention provides a molecule or substrate conjugation with a compound of the present invention. The term "PEGylation," as used herein, is used interchangeably with the term "conjugation". Thus, the product of PEGylation is known as a "conjugate."

For example, U.S. Pat. No. 6,797,257 describes imaging agents prepared by PEGylating gadolinium oxide albumin microspheres. U.S. Pat. Nos. 6,790,823 and 6,764,853 describe the PEGylation of proteins by covalently bonding through amino acid residues via a reactive group, such as, a free amino or carboxyl group. Reactive groups are those to which an activated polyethylene glycol molecule may be bound. Amino acid residues having a free amino group include lysine residues. N-terminal amino acid residues; i.e. those having a free carboxyl group, include aspartic acid residues, glutamic acid residues, and the C-terminal amino acid residue. Sulfhydryl groups may also be used as a reactive group for attaching the polyethylene glycol molecule(s).

Another aspect of the invention provides a method of PEGylating a primary or secondary label, a dye, or another detectable moiety for biosensors, bioassays, biorecognition, detection, proteomics, genomics, microarray, and other molecular biological applications. Thus, in certain embodiments, the present invention provides a detectable moiety conjugated with a compound of the present invention. Such PEGylation may be carried out by covalent linking of one PEG functionality to the detectable moiety or through coordination of a PEG functionality (e.g. thiol, amine, alcohol, carboxylic acid) to the detectable moiety. The opposite PEG end group can be further linked to targeting groups, permeation enhancers, proteins, sugars, DNA, RNA, cells, viruses, or other biomolecules for targeted delivery or recognition. Such labels or detectable moieties include but are not limited to organic and inorganic dyes, semiconducting nanoparticles (e.g. CdSe, CdS, CdSe/ZnS, ZnSe, PbSe nanoparticles), magnetic nanoparticles (e.g. Co, FePt, $Fe_3O_4$, $Fe_2O_3$ nanoparticles), or other metal nanoparticles (e.g. Au nanoparticles). For representative examples of nanoparticle PEGylation see Takae, S.; Akiyama, Y.; Otsuka, H.; Nakamura, T.; Nagasaki, Y.; Kataoka, K. "Ligand density effect on biorecognition by PEGylated gold nanoparticles: regulated interaction of RCA120 lectin with lactose installed to the distal end of tethered PEG strands on gold surface" *Biomacromolecules* 2005, 6, 818-824; Ishii, T.; Sunaga, Y.; Otsuka, H.; Nagasaki, Y.; Kataoka, K. "Preparation of water soluble CdS quantum dots stabilized by functional poly(ethylene glycol) and its application for bioassay" *J. Photopolym. Sci. Technol.* 2004, 17, 95-98; Otsuka, H.; Akiyama, Y.; Nagasaki, Y.; Kataoka, K. "Quantitative and Reversible Lectin-Induced Association of Gold Nanoparticles Modified with α-Lactosyl-ω-mercapto-poly(ethylene glycol)" *J. Am. Chem. Soc.* 2001, 123, 8226-8230; Åkerman, M. E.; Chan, W. C. W.; Laakkonen, P.; Bhatia, S. N.; Ruoslahti, E. R. "Nanocrystal targeting in vivo" *P. Natl. Acad. Sci. USA* 2002, 99, 12617-12621; Skaff, H.; Emrick, T. "A Rapid Route to Amphiphilic Cadmium Selenide Nanoparticles Functionalized with Poly(ethylene glycol)" *Chem. Comm.*, 2003, 1, 52-53.

Accordingly, another aspect of the present invention provides a method of PEGylating a biomolecule with a compound of formula I as described generally above and in classes and subclasses defined above and herein. Thus, in certain embodiments, the present invention provides a biomolecule conjugated with a compound of the present invention. In certain embodiments, the present invention provides a method of PEGylating a therapeutic or a therapeutic carrier such as a protein, a cell, a virus particle, a plasmid, an oligopeptide, an oligonucleotide (e.g. siRNA, miRNA, aptamer), small molecule drug, a liposome, a polymersome, a polymer microshere, or a lipid emulsion with a compound of formula I as described generally above and in classes and subclasses defined above and herein. According to another aspect, the present invention provides a method for PEGylating a substrate. Such PEGylation may be carried out by covalent linking of a terminal PEG functionality to the substrate or using any number of bioconjugation techniques.

The bifunctional PEG's of the present invention are also useful for linking two biomolecules together wherein said biomolecules are the same or different from each other. For example, one terminus of the present compounds may be linked to a surface, another polymer, therapeutic, therapeutic carrier, protein, cell, virus particle, a plasmid, oligopeptide, oligonucleotide (e.g. siRNA, miRNA, aptamer), small molecule drug, liposome, polymersome, polymer microshere, lipid emulsion, or a detectable moiety and the other terminus of the present compounds may be linked to a surface, targeting group, permeation enhancer, growth factor, protein, sugar, DNA, RNA, cell, virus, diagnostic agent, or a detectable moiety. Accordingly, the present invention also provides a method for linking two biomolecules together wherein said method comprises coupling one terminus of a compound of formula I to a first biomolecule then coupling the other terminus of a compound of formula I to a second molecule, wherein the first and second biomolecules may be the same or different from each other.

Accordingly, one aspect of the present invention provides a method of PEGylating a protein therapeutic with a compound of formula I as described generally above and in classes and subclasses defined above and herein. Thus, in certain embodiments, the present invention provides a protein therapeutic conjugated with a compound of the present invention. Such PEGylation may be carried out by covalent linking of one PEG functionality to the protein using any number of bioconjugation techniques. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of PEGylating a protein see Harris, J. M.; Chess, R. B. "Effect of PEGylation on Pharmaceuticals" *Nat. Rev. Drug. Discov.* 2003, 2, 214-221; Kozlowski, A.; Harris, J. M. "Improvements in protein PEGylation: pegylated interferons for treatment of hepatitis C" *J. Control. Release* 2001, 72, 217-224; Koslowski, A.; Charles, S. A.; Harris, J. M. "Development of pegylated interferons for the treatment of chronic hepatitis C" *Biodrugs* 2001, 15, 419-429; Harris, J. M.; Martin, N. E.; Modi, M. "Pegylation: a novel process for modifying pharmacokinetics" *Clin. Pharmacokinet.* 2001, 40, 539-551;

Roberts, M. J.; Bentley, M. D.; Harris, J. M. "Chemistry for peptide and protein PEGylation" *Adv. Drug Deliver. Rev.* 2002, 54, 459-476.

Another aspect of the present invention provides a method of PEGylating a small molecule drug with a compound of formula I as described generally above and in classes and subclasses defined above and herein. Thus, in certain embodiments, the present invention provides a small molecule drug conjugated with a compound of the present invention, also referred to as a "drug-polymer conjugate." Such PEGylation may be carried out by covalent linking of one PEG functionality to the small molecule drug using any number of bioconjugation techniques. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of PEGylating a small molecule drug see Greenwald, R. B. "PEG drugs: an overview" *J. Control. Release* 2001, 74, 159-171; Caliceti, P.; Monfardini, C.; Sartore, L.; Schiavon, O.; Baccichetti, F.; Carlassare, F.; Veronese, F. M. "Preparation and properties of monomethoxy poly(ethylene glycol) doxorubicin conjugates linked by an amino acid or a peptide as spacer" *Il Farmaco* 1993, 48, 919-932; Fleming, A. B.; Haverstick, K.; Saltzman, W. M. "In vitro cytotoxicity and in vivo distribution after direct delivery of PEG-camptothecin conjugates to the rat brain" *Bioconjug. Chem.* 2004, 15, 1364-1375.

Yet another aspect of the present invention provides a drug-polymer conjugate comprising a compound of formula I and a pharmaceutically active agent. In still another aspect of the present invention, pharmaceutically acceptable compositions are provided, wherein these compositions comprise a drug-polymer conjugate as described herein, and optionally comprise a pharmaceutically acceptable carrier, adjuvant or vehicle. In certain embodiments, such compositions optionally further comprise one or more additional therapeutic agents.

One of ordinary skill in the art would recognize that the present compounds are useful for the PEGylation of small molecule drugs. Small molecule drugs suitable for PEGylation with the present compounds include, but are not limited to, those having a functional group suitable for covalently linking to the bifunctional PEG's of the present invention. Such drugs include, without limitation, chemotherapeutic agents or other anti-proliferative agents including taxanes (Taxol and taxotere derivatives), camptothecin, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), angiogenesis inhibitors (Avastin) and hormones (Tamoxifen, Leuprolide, Flutamide, and Megestrol), Gleevec, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of small molecule drugs that may be PEGylated with the compounds of this invention include treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Another aspect of the present invention provides a method of PEGylating a virus with a compound of formula I as described generally above and in classes and subclasses defined above and herein. Thus, in certain embodiments, the present invention provides a virus conjugated with a compound of the present invention. Such PEGylation may be carried out by covalent linking of one PEG functionality to the virus using any number of bioconjugation techniques. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of virus PEGylation see Gupta, S. S.; Kuzelka, J.; Singh, P.; Lewis, W. G.; Manchester, M.; Finn, M. G. "Accelerated Bioorthogonal Conjugation: A Practical Method for the Ligation of Diverse Functional Molecules to a Polyvalent Virus Scaffold" *Bioconjug. Chem.* 2005, 16, 1572-1579; Raja, K. S.; Wang, Q.; Gonzalez, M. J.; Manchester, M.; Johnson, J. E.; Finn, M. G. "Hybrid Virus-Polymer Materials. 1. Synthesis and Properties of PEG-Decorated Cowpea Mosaic Virus" *Biomacromolecules* 2003, 4, 472-476; Oh, I. K.; Mok, H.; Park, T. G. "Folate Immobilized and PEGylated Adenovirus for Retargeting to Tumor Cells" *Bioconjugate Chem*. ASAP Article (Published online Apr. 14, 2006)

Yet another aspect of the present invention provides a method of PEGylating therapeutic carriers such as liposomes, polymersomes, microspheres, capsules, or lipid emulsions with a compound of formula I as described generally above and in classes and subclasses defined above and herein. Thus, in certain embodiments, the present invention provides a therapeutic carrier conjugated with a compound of the present invention. Such PEGylation may be carried out by covalent linking of one PEG functionality to the therapeutic carrier using any number of bioconjugation techniques or by the non-covalent incorporation of a PEGylated molecule (e.g. lipid, phospholipid, or polymer) into the carrier. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of PEGylating therapeutic carriers see Lukyanov, A. N.; Elbayoumi, T. A.; Chakilam, A. R.;

Torchilin, V. P. "Tumor-targeted liposomes: doxorubicin-loaded long-circulating liposomes modified with anti-cancer antibody" *J. Control. Release* 2004, 100, 135-144; Forssen, E.; Willis, M. "Ligand-targeted liposomes" *Adv. Drug Del. Rev.* 1998, 29, 249-271; Koning, G. A.; Schiffelers, R. M.; Wauben, M. H. M.; Kok, R. J.; Mastrobattista, E.; Molema, G.; ten Hagen, T. L. M.; Storm, G. "Targeting of Angiogenic Endothelial Cells at Sites of Inflammation by Dexamethasone Phosphate-Containing RGD Peptide Liposomes Inhibits Experimental Arthritis" *Arthritis Rheum.* 2006, 54, 1198-1208; Torchilin, V. P. "Structure and design of polymeric surfactant-based drug delivery systems" *J. Control. Release* 2001, 73, 137-172.

Another aspect of the present invention provides a method of PEGylating a cell with a compound of formula I as described generally above and in classes and subclasses defined above and herein. Thus, in certain embodiments, the present invention provides a cell conjugated with a compound of the present invention. Such PEGylation may be carried out by covalent linking of one PEG functionality to the cell using any number of bioconjugation techniques. The opposite PEG end group can be further linked to targeting groups, permeation enhancers, proteins, sugars, DNA, RNA, cells, viruses, dyes, detectable moieties, labels or other biomolecules for targeted delivery, biorecognition, or detection. See Scott, M. D.; Chen, A. M. "Beyond the red cell: pegylation of other blood cells and tissues" *Transfus. Clin. Biol.* 2004, 11, 40-46.

Another aspect of the present invention provides a method of PEGylating the surface of a natural or synthetic material or biomaterial with a compound of formula I as described generally above and in classes and subclasses defined above and herein. Thus, in certain embodiments, the present invention provides a surface conjugated with a compound of the present invention. Such PEGylation may be carried out by covalent linking of one PEG functionality to the surface using any number of bioconjugation techniques or through non-covalent interactions with PEG or the PEG end-groups. Such surface PEGylation generally enhances anti-fouling properties of the material and can reduce the foreign-body response of injectable or implantable biomaterials. For representative examples of Bergström, K.; Holmberg, K.; Safranj, A.; Hoffman, A. S.; Edgell, M. J.; Kozlowski, A.; Hovanes, B. A.; Harris, J. M. "Reduction of fibrinogen adsorption on PEG-coated polystyrene surfaces" *J. Biomed. Mater. Res.* 1992, 26, 779-790; Vladkova, T.; Krasteva, N.; Kostadinova, A.; Altankov, G. "Preparation of PEG-coated surfaces and a study for their interaction with living cells" *J. Biomater. Sci. Polym. Ed.* 1999, 10, 609-620.

Another aspect of the present invention provides a method of linking molecules or biomolecules to a synthetic or natural surface with a compound of formula I as described generally above and in classes and subclasses defined above and herein. Such PEGylation may be carried out by covalent linking of one PEG functionality to the surface using any number of bioconjugation techniques or through non-covalent interactions with PEG or the PEG end-groups. The opposite PEG end group can be further linked to proteins, sugars, DNA, RNA, cells, viruses, dyes, detectable moieties, labels or other biomolecules for biorecognition and/or detection. For representatives examples of using PEGylated surface linkers see Otsuka, H.; Nagasaki, Y.; Kataoka, K. "Characterization of aldehyde-PEG tethered surfaces: influence of PEG chain length on the specific biorecognition" *Langmuir* 2004, 20, 11285-11287; Muñoz, E. M.; Yu, H.; Hallock, J.; Edens, R. E.; Linhardt, R. J. "Poly(ethylene glycol)-based biosensor chip to study heparin-protein interactions" *Anal. Biochem.* 2005, 343, 176-178; Metzger, S. W.; Natesan, M.; Yanavich, C.; Schneider, J.; Leea, G. U. "Development and characterization of surface chemistries for microfabricated biosensors" *J. Vac. Sci. Technol. A* 1999, 17, 2623-2628; Hahn, M. S.; Taite, L. J.; Moon, J. J.; Rowland, M. C.; Ruffino, K. A.; West, J. L. "Photolithographic patterning of polyethylene glycol hydrogels" *Biomaterials* 2006, 27, 2519-2524; Veiseh, M.; Zareie, M. H.; Zhang, M. "Highly Selective Protein Patterning on Gold-Silicon Substrates for Biosensor Applications" *Langmuir,* 2002, 18, 6671-6678.

Another aspect of the present invention provides a method of incorporating PEG into a hydrogel with a compound of formula I as described generally above and in classes and subclasses defined above and herein. Thus, in certain embodiments, the present invention provides a hydrogel conjugated with a compound of the present invention. Such PEGylation may be carried out by the reaction of one PEG functionality for incorporation into the hydrogel matrix or through non-covalent interaction of the hydrogel and PEG or the PEG end-groups. The opposite PEG end group can be further linked to proteins, growth factors, antibodies, oligopeptides, sugars, DNA, RNA, cells, viruses, dyes, detectable moieties, labels or other biomolecules to promote cell adhesion and growth, for biorecognition, or detection. For examples of producing hydrogels from functional PEGs see Kim, P.; Kim, D. H.; Kim, B.; Choi, S. K.; Lee, S. H.; Khademhosseini, A.; Langer, R.; Suh, K. Y. "Fabrication of nanostructures of polyethylene glycol for applications to protein adsorption and cell adhesion" *Nanotechnology,* 2005, 16, 2420-2426; Raeber, G. P.; Lutolf, M. P; Hubbell, J. A. "Molecularly Engineered PEG Hydrogels: A Novel Model System for Proteolytically Mediated Cell Migration" *Biophys. J.* 2005, 89, 1374-1388; Quick, D. J.; Anseth, K. S. "DNA delivery from photocrosslinked PEG hydrogels: encapsulation efficiency, release profiles, and DNA quality" *J. Control. Release* 2004, 96, 341-351.

Another aspect of the present invention provides a method of producing block and graft copolymers of PEG using a compound of formula I as described generally above and in classes and subclasses defined above and herein. Thus, in certain embodiments, the present invention provides a block or graft copolymer comprising a compound of the present invention. PEGs of formula I which possess appropriate reactive functionality may serve as macroinitiators of cyclic esters (e.g. caprolactone, lactide, glycolide), cyclic ethers, cyclic phosphazenes, N-carboxyanhydrides (NCAs), or vinyl monomers (e.g. N-isopropylacrylamide, methyl acrylate, styrene) to synthesize block copolymers for use as micellar therapeutic carriers. One or both PEG functionalities can be used to initiate or mediate the growth of additional polymer blocks. In cases where a single PEG functionality serves as an initiator, the opposite PEG end group can be further linked to targeting groups, permeation enhancers, proteins, sugars, DNA, RNA, cells, viruses, dyes, detectable moieties, labels or other biomolecules for targeted delivery, biorecognition, or detection. For representative examples of PEG macroinitiators see Akiyama, Y.; Harada, A.; Nagasaki, Y.; Kataoka, K. *Macromolecules* 2000, 33, 5841-5845; Yamamoto, Y.; Nagasaki, Y.; Kato, Y.; Sugiyama, Y.; Kataoka, K. "Long-circulating poly(ethylene glycol)-poly(D,L-lactide) block copolymer micelles with modulated surface charge" *J. Control. Release* 2001, 77, 27-38; Bae, Y.; Jang, W. D.; Nishiyama, N.; Fukushima, S.; Kataoka, K. "Multifunctional polymeric micelles with folate-mediated cancer cell targeting and pH-triggered drug releasing properties for active intracellular drug delivery" *Mol. Biosyst.* 2002, 1, 242-250; Nasongkla, N.; Shuai, X.; Ai, H.; Weinberg, B. D.; Pink, J.;

Boothman, D. A.; Gao, J. "cRGD-Functionalized Polymer Micelles for Targeted Doxorubicin Delivery" Angew. *Chem. Int. Ed.* 2004, 43, 6323-6327.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds and compositions, according to the method of the present invention, may be administered using any amount and any route of administration effective for treating or lessening the severity of the disorder being treated. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

EXAMPLES

As depicted in the Examples below, in certain exemplary embodiments, compounds are prepared according to the following general procedures. It will be appreciated that, although the general methods depict the synthesis of certain compounds of the present invention, the following general methods, in addition to the Schemes set forth above and other methods known to one of ordinary skill in the art, can be applied to all compounds and subclasses and species of each of these compounds, as described herein. Each compound number referenced below corresponds to compound numbers recited in Tables 1 through 25, supra.

General Methods

Method A: Polymerization

To a stirred solution of initiator (1 mmol) in anhydrous THF (100 mL) was added a solution of potassium naphthalenide in THF (0.2 M, 5 mL, 1 mmol). The resulting solution was then cooled to 0° C. Ethylene oxide (10 g, 227 mmol) was introduced to the alkoxide solution using Schlenk techniques. Upon complete addition of the ethylene oxide, the flask was backfilled with Argon, sealed and stirred at room temperature for 24 h. At this point, additional terminating agents were added or the reaction was quenched with water and methanol followed by the removal of solvent under reduced pressure.

Method B: Purification by Solid Phase Extraction

The viscous liquid containing the desired polymer was loaded onto 100 g silica gel which was rinsed with 3% MeOH in $CHCl_3$ (1 L) followed by 10% MeOH in $CHCl_3$ (1 L) which contained the polymer product. The solvent was removed and the resulting liquid was diluted with a minimal amount of methanol and precipitated into diethyl ether. A white powder was isolated following filtration.

Method C: Purification by Liquid Extraction

The viscous liquid containing the desired polymer was dissolved in 100 mL water then extracted with $CHCl_3$ (4×300 mL). The combined organic layers dried over $MgSO_4$, and filtered. The solvent was removed and the resulting liquid was diluted with a minimal amount of methanol and precipitated in to diethyl ether. A white powder was isolated following filtration.

Method D: Removal of Benzyl Protecting Groups

To a 250 mL round bottom flask was added 10% palladium hydroxide on carbon (0.6 g) and methanol (50 mL). Dibenzylamino-polyethylene glycol (10 g) and ammonium formate (2 g) was added and the reaction heated to reflux for 16 hours. The solution was cooled, diluted with chloroform (100 mL) then filtered over celite, then the solvent removed. The resulting liquid was dissolved in 1 N sodium hydroxide and purified according to Method C.

Method E: Application of the BOC Protecting Group

To a 250 mL round bottom flask was added amino-polyethylene glycol-alcohol (10 g) and methanol (150 mL). Di-t-butyldicarbonate (10 equiv) and DMAP (1 equiv) was added and the resulting solution stirred at room temperature. The solvent was removed and purified according to Method B.

Method F: Mitsunobu Coupling

The desired PEG derivative (1 equiv) was dissolved in dichloromethane (~10 mL/g PEG). Triphenylphosphine (4 equiv) followed by the desired Mitsunobu terminating agent (5 equiv) then DIAD (3 equiv) was added to the solution then stirred for 8 hours. The solvent was removed and purified according to Method B.

Method G: Mesylation

The desired PEG derivative (1 equiv) was dissolved in $CH_2Cl_2$ (~10 mL/g PEG), and cooled to 0° C. Methanesulfonyl chloride (2 equiv) was added dropwise via syringe under nitrogen followed by addition of triethylamine (2.5 equiv). The solution was warmed to room temperature and stirred for 12 hours. The solvent was removed and the product used as is or was optionally further purified by Method B.

Method H: Azide Functionalization

The desired PEG derivative (1 equiv) was dissolved in ethanol (~10 mL/g PEG), and then $NaN_3$ (10 equiv) was added. The solution was stirred at reflux for 16 hours, allowed to cool, the solvent evaporated and purified by Method B.

Method I: Removal of the BOC Protecting Group

The desired PEG (1 g) was dissolved in a minimal amount of THF (2 mL) and stirred at room temperature. HCl in dioxane (4M, 5 mL) was added and the solution stirred under Argon for 6 hours. The solution was poured into cold diethyl ether and the polymer product obtained as a white powder following filtration.

Method J: Removal of the Oxazoline Protecting Group

The desired PEG (1 g) was dissolved in 10 mL of 3 N HCl (aq) and stirred at reflux for 4 hours. The solution was cooled and purified according to Method C.

Method K: Application of the Trifluoracetamide Group

The desired amino-PEG derivative (1 equiv) was dissolved in methanol ((~10 mL/g PEG). Ethyl trifluoracetate (3 equiv) was added and the resulting solution stirred at room temperature for 16 h. The solvent was removed and purified according to Method B.

Method L: Removal of the THP Protecting Group

The desired PEG derivative (1 equiv) was dissolved in ethanol (~10 mL/g PEG), and then pyridinium para-toluene sulfonate (PPTS) (3 equiv) was added. The solution was stirred at reflux for 16 hours, allowed to cool, the solvent evaporated and purified by Method C.

Method M: Removal of the Furan Protecting Group

The desired PEG derivative was dissolved in toluene (~10 mL/g PEG) and refluxed for 4 hours. After allowing the solution to cool, the polymer was precipitated in to diethyl ether. A white powder was isolated following filtration.

Example 1

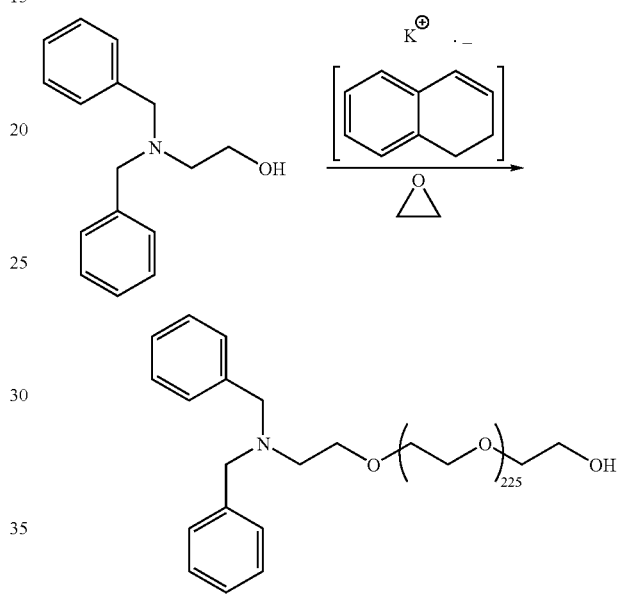

Dibenzylamino-poly(ethylene glycol)-alcohol was prepared according to Method A and purified according to Method B in 80% yield. $^1$H NMR (400 MHz, DMSO-$d_6$, δ) 7.4-7.2 (m, Ar—H), 4.63 (t, $CH_2OH$), 3.7-3.3 (br-m, —O—$CH_2$—$CH_2$—O—). GPC (DMF, PEG standards) $M_n$=10,800; PDI=1.10.

Example 2

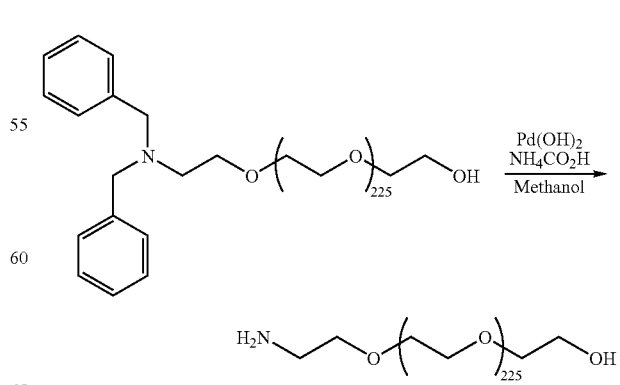

Amino-poly(ethylene glycol)-alcohol was prepared according to Method D in 84% yield. ¹H NMR (400 MHz, DMSO-d₆, δ) 3.7-3.3 (br-m, —O—CH₂—CH₂—O—), 2.62 (m, —CH₂—NH₂).

Example 3

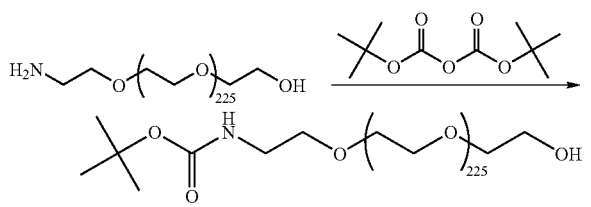

Boc-amino-poly(ethylene glycol)-alcohol was prepared according to Method E in 89% yield. ¹H NMR (400 MHz, DMSO-d₆, δ) 6.82 (br-s, CH₂—NH—CO—), 4.63 (t, CH₂OH), 3.7-3.3 (br-m, —O—CH₂—CH₂—O), 1.40 (s, —C—(CH₃)₃). GPC (DMF, PEG standards) $M_n$=10,100; PDI=1.06.

Example 4

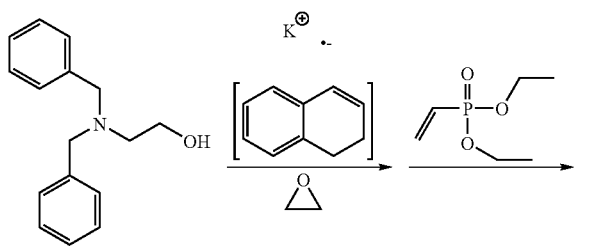

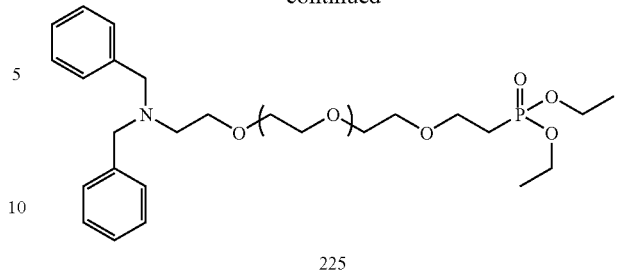

Dibenzylamino-poly(ethylene glycol)-diethylphosphonate was prepared according to Method A. After 24 h, vinyl-diethylphosphonate (0.82 g, 5 mmol) was added to the reaction using Schlenk techniques. The solution was stirred for and additional 12 h at 40° C., allowed to cool, and the solvent removed. The resulting viscous liquid was purified by solid phase extraction (The liquid was loaded onto 300 mL silica gel which was rinsed with 3% MeOH in CHCl₃ (1 L) followed by 10% MeOH in CHCl₃ (1 L) which contained the polymer product) then precipitation into cold diethyl ether to give a white powder (7.4 g, 73% yield). ¹H NMR (400 MHz, DMSO-d₆, δ) 7.3-7.2 (m, Ar—H), 4.01 (m, CH₃—CH₂—O), 3.7-3.3 (br-m, —O—CH₂—CH₂—) 2.55 (s, Ar—CH₂—N), 1.24 (m, CH₃—CH₂—O). GPC (THF, PEG standards) $M_n$=7, 700; PDI=1.05.

This compound is debenzylated according to Method D to form Compound 246.

Example 5

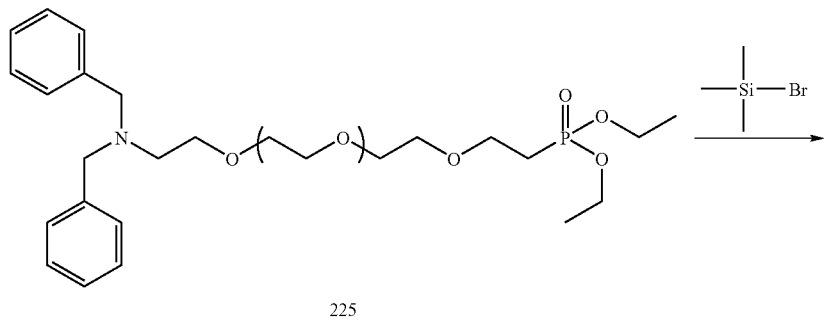

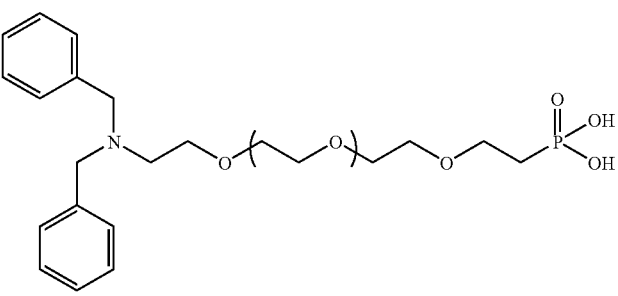

Dibenzylamino-poly(ethylene glycol)-diethylphosphonate (1 g, 0.33 mmol) was dissolved in anhydrous methylene chloride (10 mL). TMS-Br (0.17 mL, 1.3 mmol) was added via syringe and the resulting solution stirred at room temperature for 16 hours. The reaction was quenched with water (1 mL, 55 mmol) then the solution precipitated into cold diethyl ether. The product was obtained as a white powder following filtration (0.85 g, 85% yield). $^1$H NMR (400 MHz, DMSO-$d_6$, δ) 7.58, 7.47, 3.94, 3.7-3.3, 2.69.

This compound is debenzylated according to Method D to form Compound 248.

Example 6

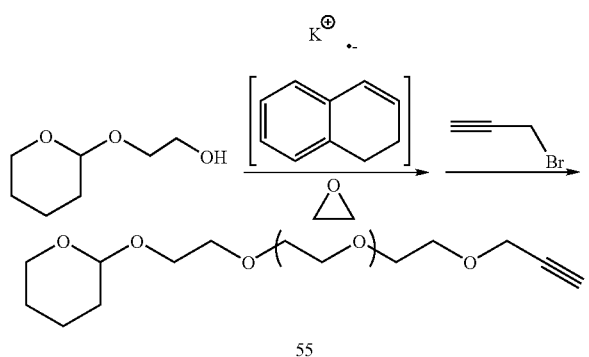

55

Tetrahydropyran-poly(ethylene glycol)-propyne was prepared according to Method A. After 24 h, propargyl bromide (3.9 g, 33 mmol) was added to the reaction using Schlenk techniques. The solution was stirred for and additional 12 h at 40° C., allowed to cool, and the solvent removed. The residue was purified according to Method B in 74% yield. $^1$H NMR (400 MHz, DMSO-$d_6$, δ) 4.55, 4.14, 3.7-3.3, 1.71, 1.61, 1.46. GPC (THF, PEG standards) $M_n$=2,400; PDI=1.04.

Example 7

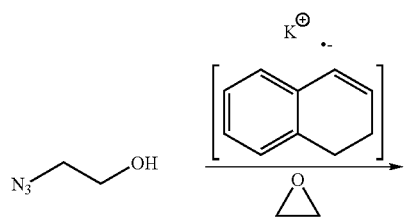

-continued

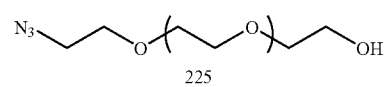

225

Azido-poly(ethylene glycol)-alcohol was prepared according to Method A followed by Method B in 80% yield. $^1$H NMR (400 MHz, DMSO-$d_6$, δ) 4.57 (t, CH$_2$OH), 3.7-3.3 (br-m, —O—CH$_2$—CH$_2$—). GPC (THF, PEG standards) $M_n$=9,500; PDI=1.05.

Example 8

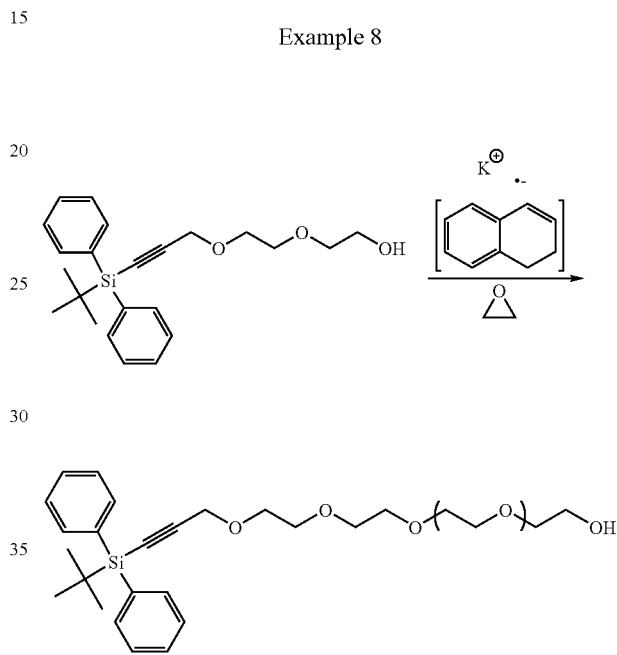

110 t-Butyldiphenylsilylpropargyl-poly(ethylene glycol) was prepared according to Method A followed by Method B in 59% yield. $^1$H NMR (400 MHz, DMSO-$d_6$, δ) 7.62 (m, Ar—H), 7.41 (m, Ar—H), 4.55 (t, CH$_2$OH), 3.7-3.3 (br-m, —O—CH$_2$—CH$_2$—O—), 0.91 (s, t-butyl). GPC (THF, PEG standards) $M_n$=2,700; PDI=1.17.

Example 9

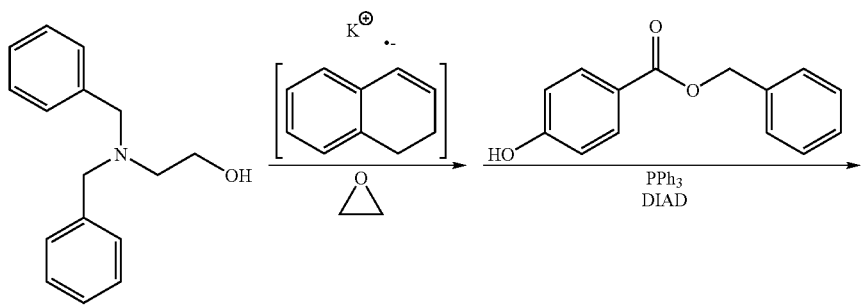

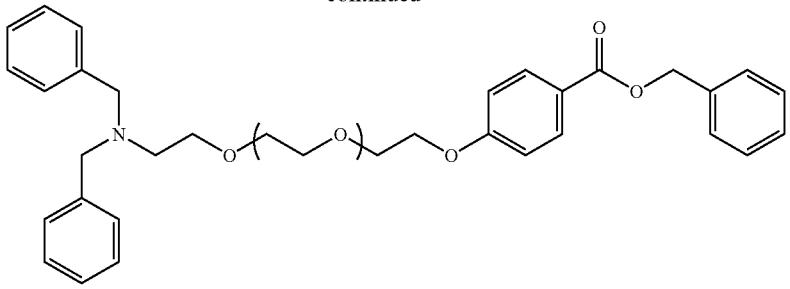
23
Dibenzylamino-poly(ethylene glycol)-benzoic acid benzyl ester was prepared according to Method A followed by Method F in 74% yield. $^1$H NMR (400 MHz, DMSO-d$_6$, δ) 7.95, 7.6-7.2, 7.05, 4.15, 3.75, 3.6-3.3, 2.55. GPC (THF, PEG standards) M$_n$=1,800; PDI=1.06.
Example 10
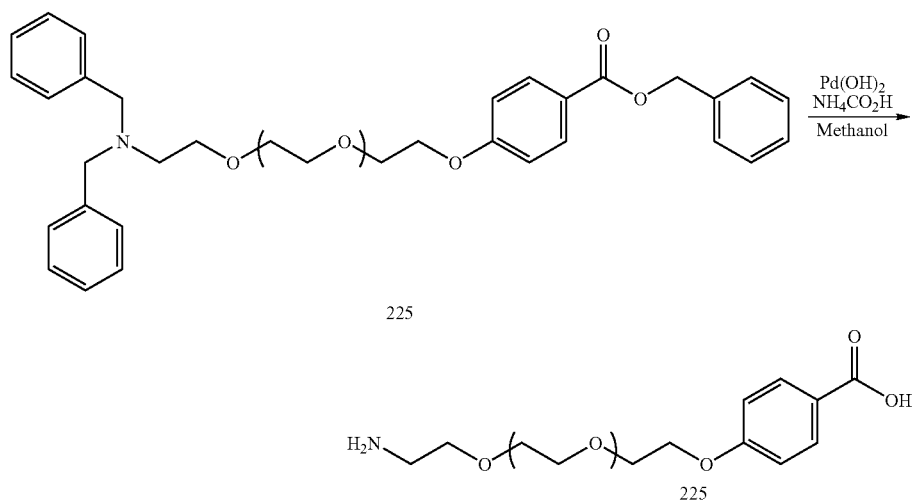
Amino-poly(ethylene glycol)-benzoic acid (Compound 228) was prepared according to Method D in 74% yield. $^1$H NMR (400 MHz, DMSO-d$_6$, δ) 7.9, 7.1, 3.7-3.3.
Example 11
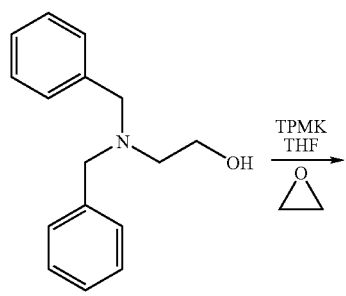
-continued
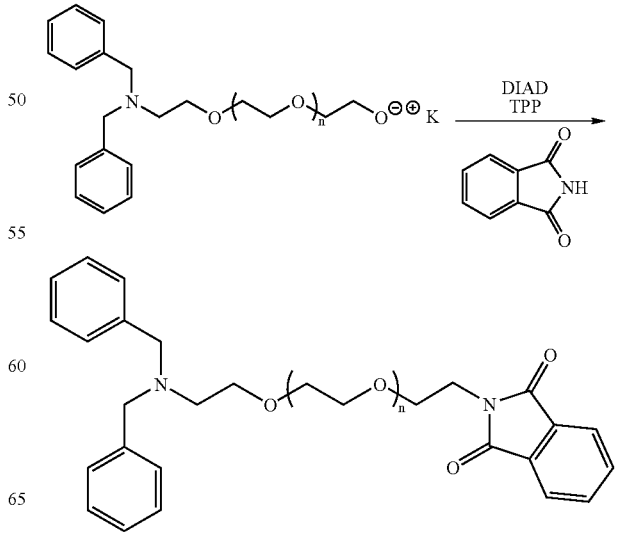

Dibenzylamino-polyethylene glycol-phthalimide was prepared according to Method A followed by Method F in 73% yield. $^1$H NMR (400 MHz, DMSO-d$_6$, δ) 7.85 (m, phthalimide Ar—H), 7.4-7.2 (m, Ar—H), 3.7-3.3 (br-m, —O—CH$_2$—CH$_2$—O—). GPC (DMF, PEG standards) M$_n$=10,900; PDI=1.11.

Example 12

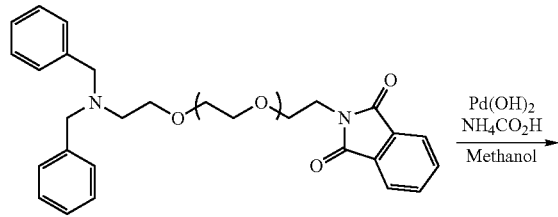

225

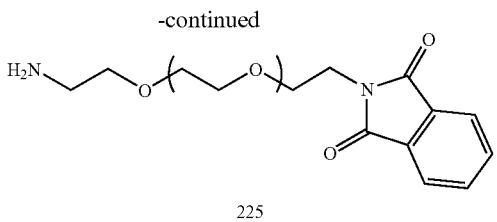

225

Amino-polyethylene glycol-phthalimide was prepared according to Method D in 63% yield. $^1$H NMR (400 MHz, DMSO-d$_6$, δ) 7.87, 7.32, 3.7-3.3, 2.66.

Example 13

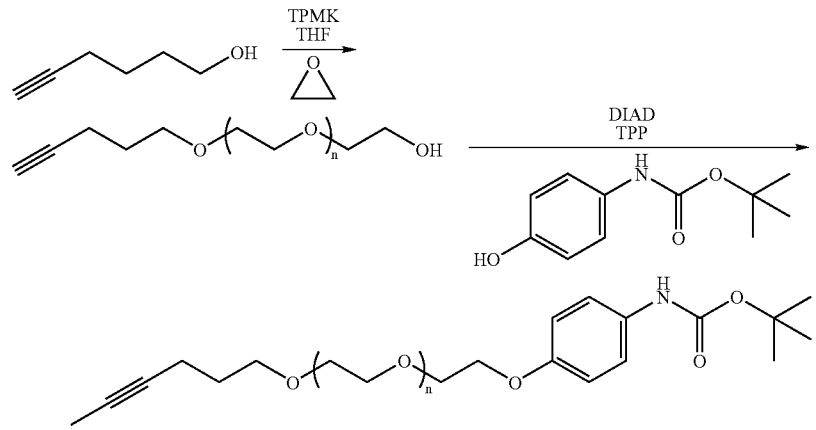

Hexyne-polyethylene glycol-BOC-aminophenoxy ether was prepared according to Method A followed by Method F in 70% yield. $^1$H NMR (400 MHz, DMSO-d$_6$, δ) 7.85 (m, phthalimide Ar—H), 7.35 (d, Ar—H), 6.85 (d, Ar—H), 3.7-3.3 (br-m, —O—CH$_2$—CH$_2$—O—), 2.14 (m, —CH$_2$), 1.73 (t, CH$_3$), 1.61 (q, —CH$_2$), 1.39 (s, —C—(CH$_3$)$_3$). GPC (DMF, PEG standards) M$_n$=10,800; PDI=1.10.

Example 14

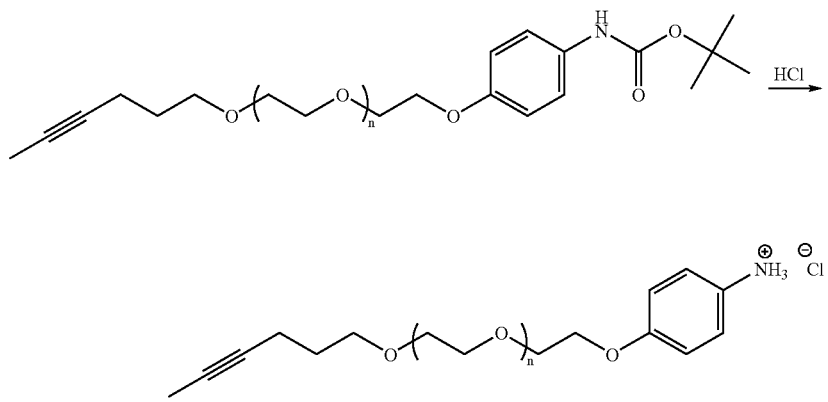

Hexyne-polyethylene glycol-amine hydrochloride phenoxy ether was prepared according to Method I in 87% yield. $^1$H NMR (400 MHz, DMSO-d$_6$, δ) 8.4 (br-s) 7.80 (m, phthalimide Ar—H), 7.37 (d, Ar—H), 6.85 (d, Ar-TH, 3.7-3.3 (br-m, —O—CH$_2$—CH$_2$—O—), 2.13 (m, —CH$_2$), 1.73 (t, CH$_3$), 1.61 (q, —CH$_2$).

Example 15

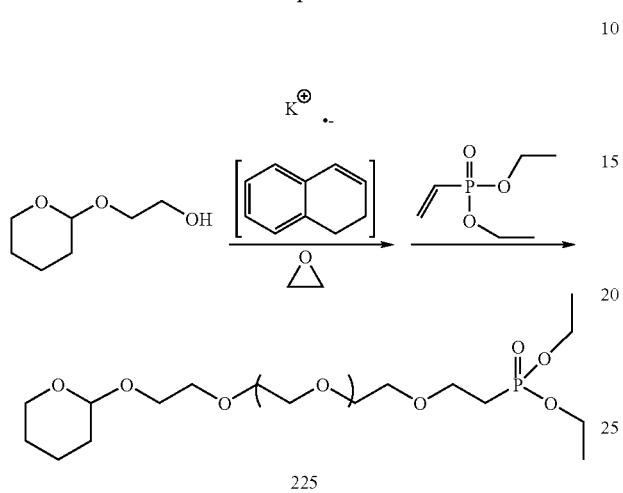

225

Tetrahydropyran-poly(ethylene glycol)-phosphonic ester was prepared according to Method A. After 24 h, vinyl diethyl phosphonate (3.2 g, 20 mmol) was added to the reaction using Schlenk techniques. The solution was stirred for and additional 12 h at 40° C., allowed to cool, and the solvent removed and purified by Method B in 70% yield. $^1$H NMR (400 MHz, DMSO-d$_6$, δ) 4.01, 3.3-3.7, 2.06, 1.71, 1.58, 1.45, 1.22, 1.09. GPC (DMF, PEG standards) M$_n$=6,700; PDI=1.05.

The THP group is removed according to Method A to form Compound 119.

The phosphonic ester is hydrolyzed according to Example 5 to form Compound 120.

Example 16

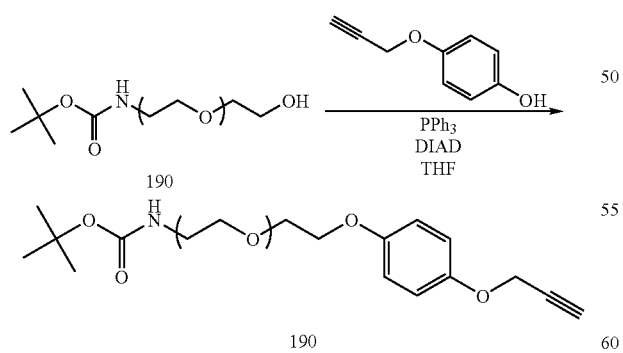

190

BOC-aminopolyethylene glycol-propargyl phenoxy ether was prepared according to Method F in 66% yield. $^1$H NMR (400 MHz, DMSO-d$_6$, δ) 7.62 m, 7.56 m, 6.89 t, 4.70 s, 4.03 t, 3.3-3.7 bm, 3.03 q, 1.37 s. GPC (DMF, PEG standards) M$_n$=7,000; PDI=1.02.

The BOC group is removed according to Method I to form the free amino compound.

Example 17

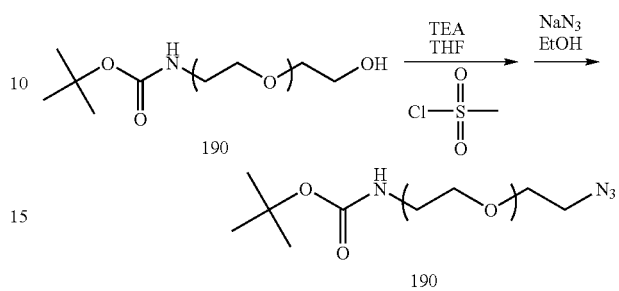

190

BOC-amino-polyethylene glycol-azide (Compound 257) was prepared according to Method G followed by Method H in 66% yield. $^1$H NMR (400 MHz, DMSO-d$_6$, δ) 6.84 t, 3.3-3.7 bm, 1.37 s. GPC (DMF, PEG standards) M$_n$=7,400; PDI=1.02.

Example 18

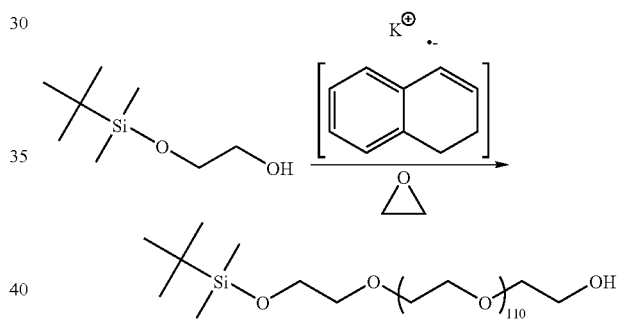

TBDMS-PEG-alcohol was prepared according to Method A in 78% yield. $^1$H NMR (400 MHz, DMSO-d$_6$, δ) 4.55 t, 3.3-3.7 bm, 0.83 s, 0.09 s. GPC (DMF, PEG standards) M$_n$=2,400; PDI=1.02.

Example 19

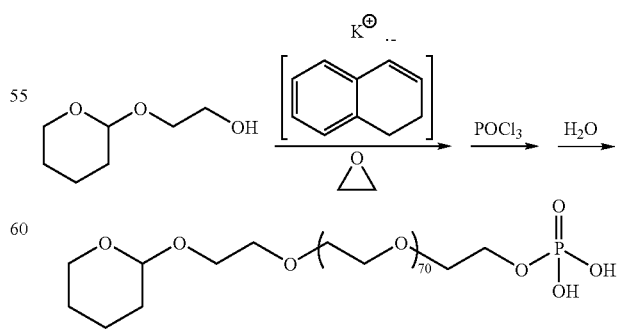

THP-PEG-phosphonic acid was prepared according to Method A. POCl$_3$ (5 equiv) was added and stirred for 6 h at room temperature. The solvent was removed and the residue purified according to Method C giving 62% yield. GPC (DMF, PEG standards) $M_n$=4,100; PDI=1.43.

Example 20

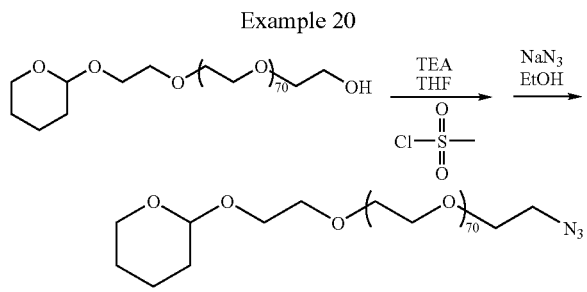

THP-PEG-azide was prepared according to Method G followed by Method H in 92% yield. GPC (DMF, PEG standards) $M_n$=2,400; PDI=1.01. $^1$H NMR (400 MHz, DMSO-d$_6$, δ) 3.3-3.7 bm, 1.71 m, 1.60 m, 1.44 m. 1.18 m.

Example 21

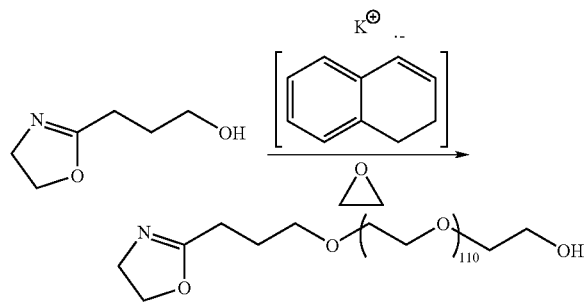

Oxazoline-PEG-OH was prepared according to Method A followed by Method B in 49% yield. $^1$H NMR (400 MHz, DMSO-d$_6$, δ) 4.14 t, 3.3-3.7 bm, 2.24 t, 1.75 quint. GPC (DMF, PEG standards) $M_n$=4,850; PDI=1.04.

Example 22

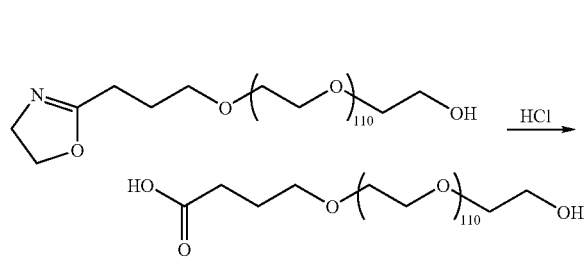

Carboxylic acid-PEG-OH was prepared according to Method J in 82% yield. $^1$H NMR (400 MHz, DMSO-d$_6$, δ) 4.55 t, 3.3-3.7 bm, 2.24 t, 2.13 t, 1.71 quint.

Example 23

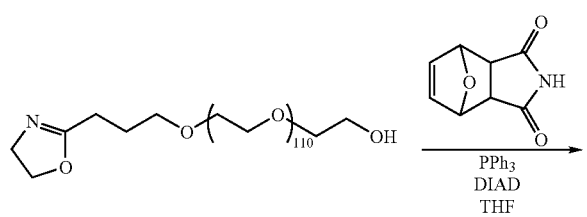

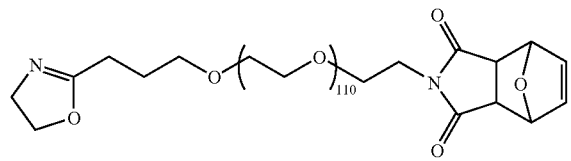

Oxazoline-PEG-Oxanorbornene was prepared by Method F in 76% yield. $^1$H NMR (400 MHz, DMSO-d$_6$, δ) 6.59 s, 5.12 s, 4.15 t, 3.3-3.7 bm, 2.94 s, 2.22 t, 1.75 quint. GPC (DMF, PEG standards) $M_n$=5,100; PDI=1.04.

Example 24

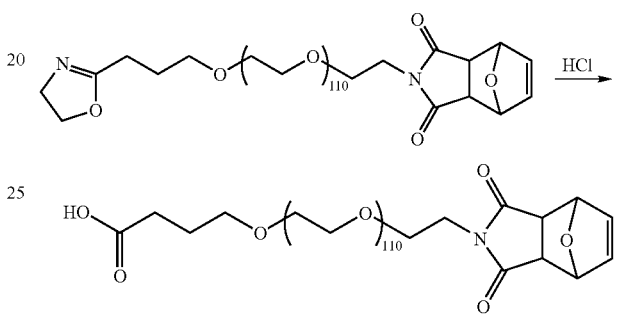

Carboxylic acid-PEG-oxanorbornene was prepared according to Method J in 90% yield. $^1$H NMR (400 MHz, DMSO-d$_6$, δ) 6.59 s, 5.12 s, 3.3-3.7 bm, 2.94 s, 2.24 t, 2.13 t, 1.71 quint. GPC (DMF, PEG standards) $M_n$=5,100; PDI=1.04.

Example 25

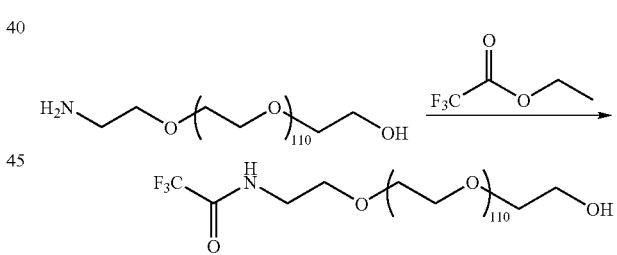

Trifluoroacetamide-PEG-alcohol was prepared according to Method K in 73% yield. $^1$H NMR (400 MHz, DMSO-d$_6$, δ) 4.55 t, 3.3-3.7 bm. GPC (DMF, PEG standards) $M_n$=5,000; PDI=1.07.

Example 26

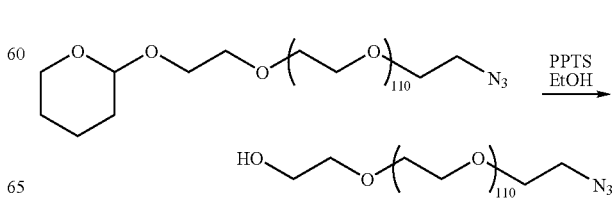

Azido-PEG-alcohol was prepared according to Method L in 84% yield. $^1$H NMR (400 MHz, DMSO-d$_6$, δ) 4.55 t, 3.3-3.7 bm. GPC (DMF, PEG standards) M$_n$=5,200; PDI=1.03.

Example 27

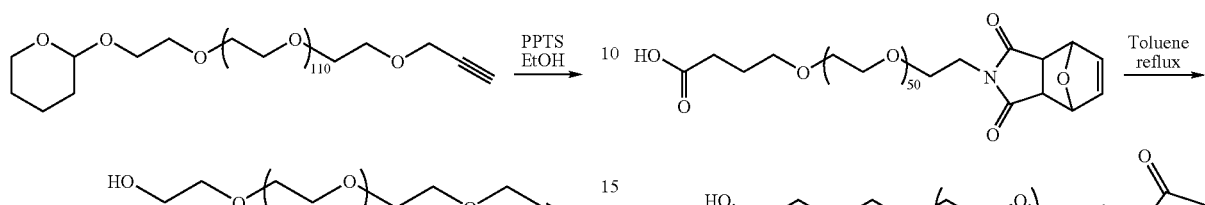

Propargyl-PEG-alcohol was prepared according to Method L in 87% yield. $^1$H NMR (400 MHz, DMSO-d$_6$, δ) 4.55 t, 4.14 d, 3.3-3.7 bm. GPC (DMF, PEG standards) M$_n$=5,400; PDI=1.03.

Example 28

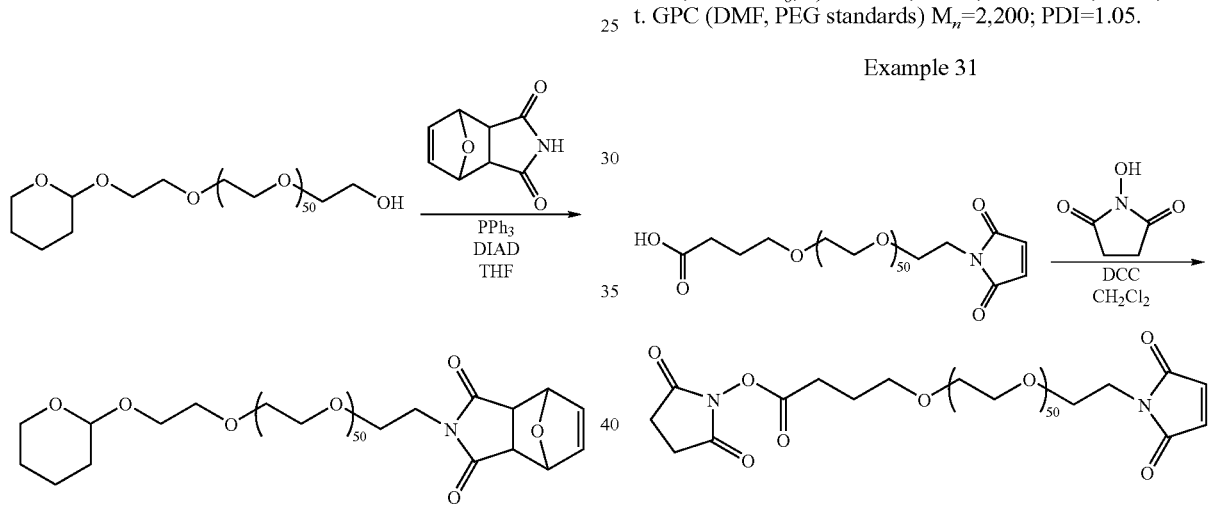

THP-PEG-oxanorbornene was prepared according to Method F in 97% yield. $^1$H NMR (400 MHz, DMSO-d$_6$, δ) 6.55 s, 5.12 s, 4.57 t, 3.3-3.7 bm, 2.92 s, 1.71 m, 1.60 m, 1.44 m, 1.18 m.

Example 29

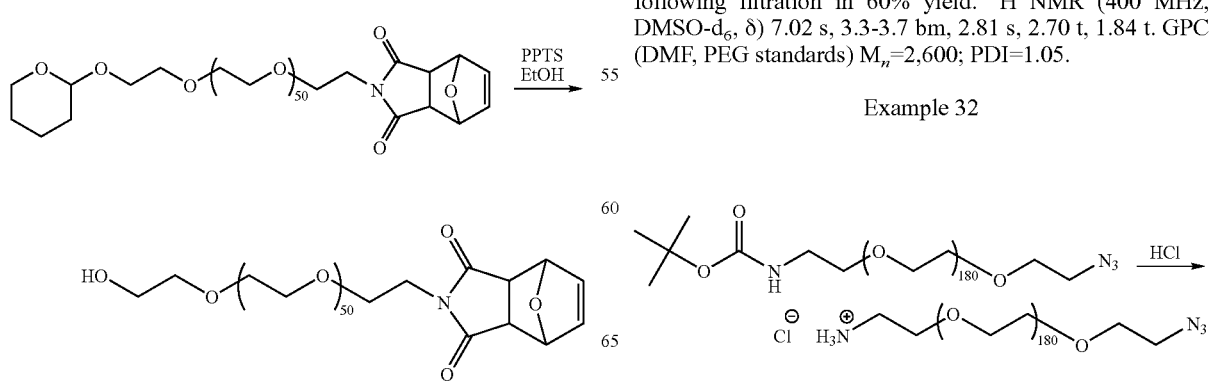

Alcohol-PEG-oxanorbornene was prepared according to Method L in 55% yield. $^1$H NMR (400 MHz, DMSO-d$_6$, δ) 6.55 s, 5.12 s, 4.55 t, 3.3-3.7 bm, 2.94 s.

Example 30

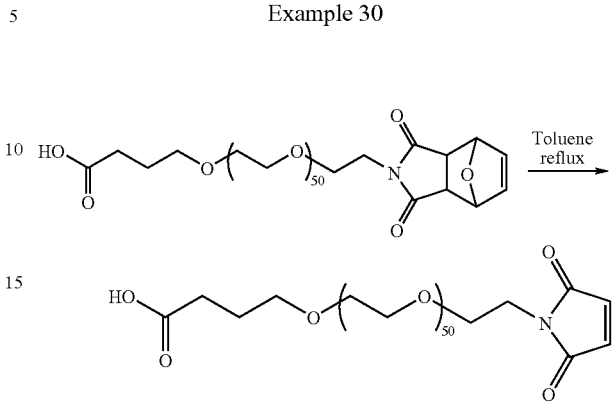

Carboxylic acid-PEG-maleimide (compound 18) was prepared according to Method L in 90% yield. $^1$H NMR (400 MHz, DMSO-d$_6$, δ) 11.94 bs, 7.02 s, 3.3-3.7 bm, 2.24 t, 1.70 t. GPC (DMF, PEG standards) M$_n$=2,200; PDI=1.05.

Example 31

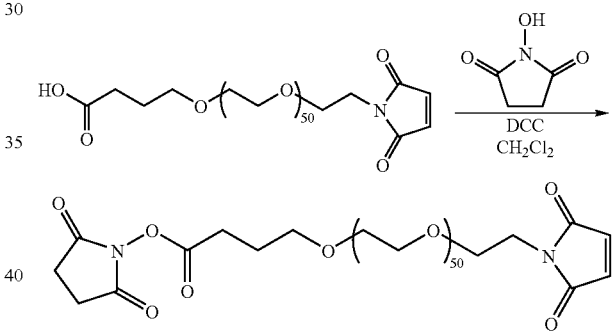

NHS-Ester-PEG-maleimide was prepared by dissolving PEG (1 equiv) and N-hydroxysuccinimide (5 equiv) in methylene chloride (~10 mL/g PEG). DCC (5 equiv) was then added and the solution stirred at room temperature for 12 hours. The solution was filtered and the solvent removed. The residue was dissolved in isopropanol and precipitated into diethyl ether, filtered, redissolved in isopropanol and precipitated again into diethyl ether. A white powder was isolated following filtration in 60% yield. $^1$H NMR (400 MHz, DMSO-d$_6$, δ) 7.02 s, 3.3-3.7 bm, 2.81 s, 2.70 t, 1.84 t. GPC (DMF, PEG standards) M$_n$=2,600; PDI=1.05.

Example 32

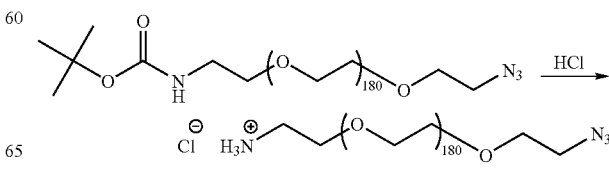

Azido-PEG-amine hydrochloride was prepared according to Method I in 88% yield. $^1$H NMR (400 MHz, DMSO-d$_6$, δ) 7.86, 3.3-3.7, 2.71.

Example 33

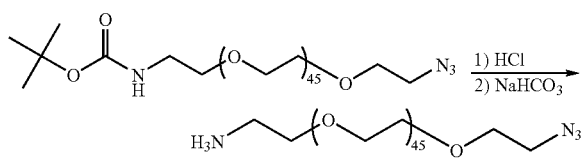

Azido-PEG-amine

Boc-PEG-azide (5 g) was dissolved in methanol (50 mL) and stirred at room temperature until homogeneous. Anhydrous HCl was bubbled through the reaction for 5 minutes and the reaction stirred for an additional 15 minutes. The solvent was evaporated, dissolved in saturated NaHCO$_3$ (30 mL, aqueous), then the product extracted with dichloromethane (3×60 mL). The combined organic layers were dried over MgSO$_4$, and filtered. The solvent was removed and the resulting liquid was diluted with a minimal amount of methanol and precipitated in to diethyl ether. A white powder (4.5 g, 90% yield) was isolated following filtration. $^1$H NMR (400 MHz, DMSO-d$_6$, δ) 3.3-3.7, 2.71. IR (cm$^{-1}$) 3383, 2781, 2102, 1466, 1341, 1279, 1241, 1145, 1101, 1060, 956, 841.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound selected from any of the following formulae:

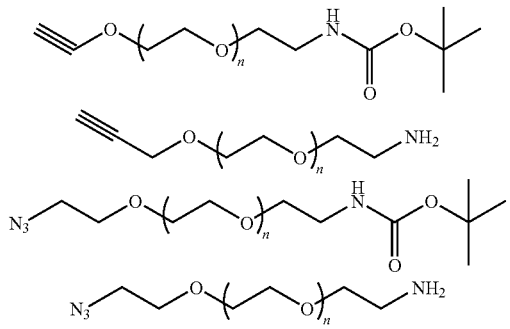

or salt thereof, wherein:
each n is independently 10-2500.

2. The compound of claim 1, wherein each n is independently about 10 to about 40.

3. The compound of claim 1, wherein each n is independently about 40 to about 60.

4. The compound of claim 1, wherein each n is independently about 60 to about 90.

5. The compound of claim 1, wherein each n is independently about 90 to about 150.

6. The compound of claim 1, wherein each n is independently about 150 to about 200.

7. The compound of claim 1, wherein each n is independently about 200 to about 250.

8. The compound of claim 1, wherein each n is independently about 300 to about 375.

9. The compound of claim 1, wherein each n is independently about 400 to about 500.

10. The compound of claim 1, wherein each n is independently about 650 to about 750.

11. The compound of claim 1, wherein each n is independently 50±10.

12. The compound of claim 1, wherein each n is independently 80±10.

13. The compound of claim 1, wherein each n is independently 115±10.

14. The compound of claim 1, wherein each n is independently 180±10.

15. The compound of claim 1, wherein each n is independently 225±10.

16. The compound of claim 1, wherein each n is independently 225.

17. The compound of claim 1, wherein each n is independently 270.

18. The compound of claim 1, wherein said compound is

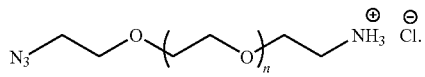

19. The compound of claim 1, wherein said compound is

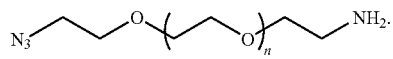

20. The compound of claim 1, wherein said compound is

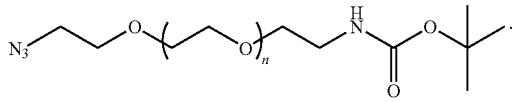

21. The compound of claim 1, wherein said compound is

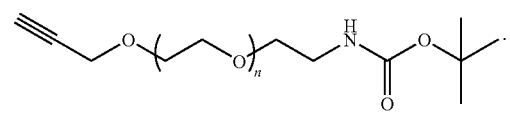

22. The compound of claim 1, wherein said compound is

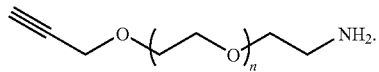

* * * * *